United States Patent
Hetz Flores et al.

(10) Patent No.: US 10,512,698 B2
(45) Date of Patent: Dec. 24, 2019

(54) METHOD FOR GENETIC TREATMENT USING THE AAV-XBP1S/GFP VIRUS AND USE THEREOF IN THE PREVENTION AND TREATMENT OF AMYOTROPHIC LATERAL SCLEROSIS

(71) Applicant: Universidad de Chile, Santiago (CL)

(72) Inventors: Claudio Andrés Hetz Flores, Santiago (CL); Vicente Spiro Valenzuela Paterakis, Santiago (CL)

(73) Assignee: UNIVERSIDAD DE CHILE, Santiago de Chile (CL)

(*) Notice: Subject to any disclaimer, the term of this patent is extended or adjusted under 35 U.S.C. 154(b) by 0 days.

(21) Appl. No.: 15/767,086

(22) PCT Filed: Sep. 30, 2016

(86) PCT No.: PCT/CL2016/000056
§ 371 (c)(1),
(2) Date: Oct. 11, 2018

(87) PCT Pub. No.: WO2017/059554
PCT Pub. Date: Apr. 13, 2017

(65) Prior Publication Data
US 2019/0030188 A1    Jan. 31, 2019

(30) Foreign Application Priority Data
Oct. 9, 2015    (CL) .................... 3024-2015

(51) Int. Cl.
| | |
|---|---|
| *A61P 25/00* | (2006.01) |
| *A61K 48/00* | (2006.01) |
| *C07H 21/04* | (2006.01) |
| *C12N 15/864* | (2006.01) |
| *A61K 9/00* | (2006.01) |
| *C12N 9/02* | (2006.01) |

(52) U.S. Cl.
CPC ........ *A61K 48/0066* (2013.01); *A61K 9/0019* (2013.01); *A61K 48/00* (2013.01); *A61K 48/0075* (2013.01); *A61P 25/00* (2018.01); *C07H 21/04* (2013.01); *C12N 9/0089* (2013.01); *C12N 15/864* (2013.01); *C12N 15/8645* (2013.01); *C12Y 115/01001* (2013.01)

(58) Field of Classification Search
CPC .. A61K 48/0066; A61K 9/0019; A61K 48/00; A61K 48/0075; A61K 31/704; A61K 35/76; A61K 48/0058; A61K 9/141; A61P 25/00; C12N 15/8645
See application file for complete search history.

(56) References Cited

FOREIGN PATENT DOCUMENTS

| | | |
|---|---|---|
| CL | 2014003590 | 7/2015 |
| EP | 2489733 | 8/2012 |
| EP | 2497500 | 9/2012 |
| EP | 3254702 | 12/2017 |

OTHER PUBLICATIONS

Acosta-Alvear et al., "XBP1 controls diverse cell type- and condition-specific transcriptional regulatory networks." Mal Cell, Jul. 6, 2007, 27(1):53-66.
Alami et al., "Axonal transport of TDP-43 mRNA granules is impaired by ALS-causing mutations." Neuron, Feb. 5, 2014, 81(3):536-543.
Atkin et al., "Endoplasmic reticulum stress and induction of the unfolded protein response in human sporadic amyotrophic lateral sclerosis." Neurobiol Dis, Jun. 1, 2008. 30(3):400-407.
Bartlett et al., "Selective and rapid uptake of adenoassociated virus type 2 in brain." Human gene therapy, May 20, 1998, 9(8):1181-6.
Bernard-Marissal et al., "Calreticulin levels determine onset of early muscle denervation by fast motoneurons of ALS model mice." Neurobiology of disease, Jan. 31, 2015, 73:130-6.
Boyce et al.,"A selective inhibitor of eIF2alpha dephosphorylation protects cells from ER stress." Science, Feb. 11, 2005, 307(5711):935-939.
Calfon et al., "IRE1 couples endoplasmic reticulum load to secretory capacity by processing the XBP-1 mRNA." Nature, Jan. 3, 2002. 415(6867):92-96.
Castillo et al., "Measurement of autophagy flux in the nervous system in vivo." Cell death & disease, Nov. 2013, 4:e917, 11 pages.
Castillo et al., "Trehalose delays the progression of amyotrophic lateral sclerosis by enhancing autophagy in motoneurons." Autophagy, Sep. 29, 2013, 9(9):1308-1320.
Ferraiuolo et al., "Molecular pathways of motor neuron injury in amyotrophic 5 lateral sclerosis." Nature reviews. Neurology, Nov. 2011, 7(11):616-30.
GenBank Accession No. NM001271730, "Mus musculus X-box binding protein 1 (Xbp1), transcript variant 2, mRNA," Feb. 15, 2015, 5 pages.
Glascock et al., "Delivery of therapeutic agents through intracerebroventricular (ICV) and intravenous (IV) injection in mice." J Vis Exp, Oct. 2011, 56:e2968, 4 pages.
Gray et al., "Production of Recombinant Adeno-Associated Viral Vectors and Use in In Vitro and In Vivo Administration," Curr Protoc Neurosci, Oct. 2011, Chapter Unit 4.17.
Harding et al., "An integrated stress response regulates amino acid metabolism and resistance to oxidative stress." Mal Cell, Mar. 1, 2003. 11(3):619-633.
Hareendran et al., "Adeno-associated virus (AAV) vectors in gene therapy: immune challenges and strategies to circumvent them." Rev Med Viral, Nov. 2013, 23(6)399-413.
Hetz et al., "Disturbance of endoplasmic reticulum proteostasis in neurodegenerative diseases." Nature reviews. Neuroscience, Apr. 2014, 15(4):233-249.

(Continued)

*Primary Examiner* — Bao Q Li
(74) *Attorney, Agent, or Firm* — Procopio, Cory, Hargreaves & Savitch LLP

(57) ABSTRACT

This invention presents the method and use of the AAV-XBP1s/GFP virus, in the prevention and treatment of amyotrophic lateral sclerosis, as presented in the in vivo studies in FIG. 6.

15 Claims, 9 Drawing Sheets

Specification includes a Sequence Listing.

(56) References Cited

OTHER PUBLICATIONS

Hetz et al., "Targeting the unfolded protein response in disease. Nature reviews." Drug discovery, Sep. 2013, 12(9):703-19.
Hetz et al., "The proapoptotic BCL-2 family member BIM mediates motoneuron loss in a model of amyotrophic lateral sclerosis." Cell death and differentiation, Jul. 2007, 14(7):1386-1389.
Hetz et al., "Unfolded protein response transcription factor XBP-1 does not influence prion replication or pathogenesis." Proc Natl Acad Sci U SA, Jan. 15, 2008, 105(2):757-762.
Hetz et al., "XBP-1 deficiency in the nervous systems protects against amyotrophic lateral sclerosis by increasing autophagy." Genes Dev. Oct. 23, 2009, 23(19):2294-306.
Hetz, "The unfolded protein response: controlling cell fate decisions under ER stress and beyond." Nature reviews. Molecular cell biology, Feb. 2012, 13(2):89-102.
Hu et al., Differential Effects of Unfolded Protein Response Pathways on Axon Injury-Induced Death of Retinal Ganglion Cells, Neuron, Feb. 9, 2012, 73(3):445-452.
International Preliminary Report on Patentability in International Application No. PCT/CL2016/000056, dated Apr. 10, 2018, 21 pages with English Translation.
International Search Report and Written Opinion in International Application No. PCT/CL2016/000056, dated Feb. 1, 2017, 32 pages with English Translation.
Ito et al., "Involvement of CHOP, an ER-stress apoptotic mediator, in both human sporadic ALS and ALS model mice." Neurobiol Dis, Dec. 31, 2009, 36(3):470-6.
Jiang et al., Guanabenz delays the onset of disease symptoms, extends lifespan, improves motor performance and attenuates motor neuron loss in the SOD1 G93A mouse model of amyotrophic lateral sclerosis. Neuroscience, Sep. 26, 2014, 277:132-8.
Kieran et al., "Deletion of the BH3-only protein puma protects motoneurons from ER stress-induced apoptosis and delays motoneuron loss in ALS mice." Proc Natl Acad Sci U SA, Dec. 18, 2007, 104(51):20606-11.
Kikuchi et al., "Spinal cord endoplasmic reticulum stress associated with a microsomal accumulation of mutant superoxide dismutase-1 in an ALS model." Proc Natl Acad Sci U SA, Apr. 11, 2006, 103(15):6025-30.
Kraskiewicz et al., "InterfERing with endoplasmic reticulum stress." Trends in pharmacological sciences, Feb. 1, 2012, 33(2):53-63.
Leblond et al., "Dissection of genetic factors associated with amyotrophic lateral sclerosis." Experimental neurology, Dec. 1, 2014, 262:91-101.
Lee et al., "XBP-1 regulates a subset of endoplasmic reticulum resident chaperone genes in the unfolded protein response." Mal Cell Biol, Nov. 1, 2003, 23(21):7448-59.
Llieva et al., "Oxidative and endoplasmic reticulum stress interplay in sporadic amyotrophic lateral sclerosis." Brain, Aug. 2007, 130(12):3111-23.
Matus et al., "A new method to measure autophagy flux in the nervous system." Autophagy. Apr. 14, 2014, 10(4):710-4.
Matus et al., "Common ground: stem cell approaches find shared pathways underlying ALS." Cell stem cell, Jun. 5, 2014, 14(6):697-9.
Matus et al., "ER Dysfunction and Protein Folding Stress in ALS." International Journal of Cell Biology, 2013, 12 pages.
Matus et al., "Functional contribution of the transcription factor ATF4 to the pathogenesis of amyotrophic lateral sclerosis." PLoS One, Jul. 18, 2013, 8(7):e66672, 12 pages.
Mori et al., "Derlin-1 overexpression ameliorates mutant SOD1-induced endoplasmic reticulum stress by reducing mutant SOD1 accumulation." Neurochem Int, Feb. 1, 2011, 58(3):344-53.
Nagata et al., "Increased ER stress during motor neuron degeneration in a transgenic mouse model of amyotrophic lateral sclerosis." Neural Res, Dec. 1, 2007, 29(8):767-71.
Pasinelli et al., "Molecular biology of amyotrophic lateral sclerosis: insights from genetics." Nature reviews. Neuroscience, Sep. 2006, 7(9):710-23.

Passini et al., "Widespread gene delivery and structure-specific patterns of expression in the brain after intraventricular injections of neonatal mice with an adeno-associated virus vector." J Viral, Dec. 15, 2001, 75(24):12382-92.
Prell et al., "The unfolded protein response in models of human mutant G93A amyotrohic lateral sclerosis." Eur J Neurosci, Mar. 2012, 35(5):652-60.
Sasaki "Endoplasmic reticulum stress in motor neurons of the spinal cord in sporadic amyotrophic lateral sclerosis." J Neuropathol Exp Neural, Apr. 1, 2010, 69(4):346-55.
Saxena et al., "A role for motoneuron subtype-selective ER stress in disease manifestations of FALS mice." Nature neuroscience, May 2009, 12(5):627-636.
Saxena et al., "Selective neuronal vulnerability in neurodegenerative diseases: from stressor thresholds to degeneration." Neuron, Jul. 2011, 71(1):35-48.
Shimazawa et al., "An Inducer of VGF Protects Cells against ER Stress-Induced Cell Death and Prolongs Survival in the Mutant SOD1 Animal Models of Familial ALS." PLoS One, Dec. 2010, 5(12):e15307.
Sommer et al., "Quantification of adeno-associated virus particles and empty capsids by optical density measurement." Molecular therapy: the journal of the American Society of Gene Therapy, Jan. 2003, 7(1):122-8.
Tabas et al., "Integrating the mechanisms of apoptosis induced by endoplasmic reticulum stress." Nature cell biology, Mar. 2011, 13(3):184-90.
Urushitani et al., "Chromogranin-mediated secretion of mutant superoxide dismutase proteins linked to amyotrophic lateral sclerosis." Nature neuroscience, Jan. 2006, 9(1):108-18.
Valdes et al., "Control of dopaminergic neuron survival by the unfolded protein response transcription factor XBP1." Proc Natl Acad Sci USA., May 6, 2014, 111(18):6804-9.
Valenzuela et al., "Activation of the unfolded protein response enhances motor recovery after spinal cord injury." Cell Death Dis., Feb. 16, 2012, 3:e272, 9 pages.
Vlug et al., "ATF3 expression precedes death of spinal motoneurons in amyotrophic lateral sclerosis-SOD1 transgenic mice and correlates with c-Jun phosphorylation, CHOP expression, somatodendritic ubiquitination and Golgi fragmentation." European Journal of Neuroscience, Oct. 2005, 22(8):1881-94.
Walker et al., "Protein disulphide isomerase protects against protein aggregation and is S-nitrosylated in amyotrophic lateral sclerosis." Brain, Nov. 10, 2009, 133(Pt 1):105-16.
Walker et al., "Stress signaling from the endoplasmic reticulum: A central player in the pathogenesis of amyotrophic lateral sclerosis." IUBMB life, Sep. 2011, 63(9):754-63.
Walter et al., "The unfolded protein response: from stress pathway to homeostatic regulation." Science, Nov. 25, 2011, 334(6059):1081-6.
Wang et al., "Guanabenz, which enhances the unfolded protein response, ameliorates mutant SOD1-induced amyotrophic lateral sclerosis." Neurobiology of disease, Nov. 30, 2014, 71:317-24.
Wang et al., "The unfolded protein response in familial amyotrophic lateral sclerosis." Hum Mal Genet, Dec. 15, 2010, 20(5):1008-15.
Witt et al., "An update on gene therapy in Parkinson's disease." Current neurology and neuroscience reports, Aug. 1, 2011, 11(4):362-70.
Woehlbier et al., "Modulating stress responses by the UPRosome: a matter of life and death." Trends Biochem Sci, Jun. 1, 2011, 36(6):329-37.
Wootz et al., "Caspase-12 cleavage and increased oxidative stress during motoneuron degeneration in transgenic mouse model of ALS." Biochem Biophys Res Commun, Sep. 10, 2004, 322(1):281-6.
Wootz et al., "XIAP decreases caspase-12 cleavage and calpain activity in spinal cord of ALS transgenic mice." Exp Cell Res, Jun. 10, 2006, 312(10):1890-8.
Zhang et al., "Aggregation-prone c9FTD/ALS poly(GA) RAN-translated proteins cause neurotoxicity by inducing ER stress." Acta neuropatologica, Oct. 1, 2014, 128(4):505-24.

(56) References Cited

OTHER PUBLICATIONS

Zincarelli et al., "Analysis of AAV serotypes 1-9 mediated gene expression and tropism in mice after systemic injection." Molecular therapy: the journal of the American Society of Gene Therapy, Jun. 2008, 16(6):1073-80.
Zuleta et al., "AAV-mediated delivery of the transcription factor XBP1s into the striatum reduces mutant Huntingtin aggregation in a mouse model of Huntington's Disease." Biochem Biophys Res Commun. Apr. 13, 2012, 420(3):558-63.

SEQUENCE LISTING

<160> NUMBER OF SEQ ID NOS: 5

<210> SEQ ID NO 1
<211> LENGTH: 7206
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1

```
ccggtgccta gagaaggtgg cgcggggtaa actgggaaag tgatgtcgtg tactggctcc      60 gccttttttcc cgagggtggg ggagaaccgt atataagtgc agtagtcgcc gtgaacgttc     120 ttttttcgcaa cgggtttgcc gccagaacac aggtaagtgc cgtgtgtggt tcccgcgggc    180
ctggcctctt tacgggttat ggcccttgcg tgccttgaat tacttccacc tggctgcagt    240
acgtgattct tgatcccgag cttcgggttg aagtgggtg ggagagttcg aggccttgcg     300
cttaaggagc cccttcgcct cgtgcttgag ttgaggcctg gcctgggcgc tggggccgcc    360
gcgtgcgaat ctggtggcac cttcgcgcct gtctcgctgc tttcgataag tctctagcca    420
tttaaaattt ttgatgacct gctgcgacgc ttttttttctg gcaagatagt cttgtaaatg    480
cgggccaaga tctgcacact ggtatttcgg tttttgggc gcgggcggc gacggggccc       540 gtgcgtccca gcgcacatgt tcggcgaggc ggggcctgcg agcgcggcca ccgaaatcg      600 gacgggggta gtctcaagct ggccggcctg ctctggtgcc tggcctcgcg ccgccgtgta    660
tcgccccgcc ctgggcggca aggctggccc ggtcggcacc agttgcgtga gcggaaagat     720
ggccgcttcc cggccctgct gcaggagct caaaatggag gacgcggcgc tcgggagagc      780
gggcgggtga gtcacccaca caaaggaaaa gggccttttcc gtcctcagcc gtcgcttcat    840
gtgactccac ggagtaccgg gcgccgtcca ggcacctcga ttagttctcg agcttttgga    900
gtacgtcgtc tttaggttgg ggagggggt tttatgcgat ggagttttccc cacactgagt    960 gggtggagac tgaagttagg ccagcttggc acttgatgta attctccttg gaattgccc     1020 tttttgagtt tggatcttgg ttcattctca agcctcagac agtggttcaa agttttttc     1080 ttccattttca ggtgtcgtga ggaattagct tggtactaga ggatccccgg tcgccaccat    1140
ggtgagcaag ggcgaggagc tgttcaccgg ggtggtgccc atcctggtcg agctggacgg    1200
cgacgtaaac ggccacaagt tcagcgtgtc cggcgagggc gagggcgatg ccacctacgg    1260
caagctgacc ctgaagttca tctgcaccac cggcaagctg cccgtgccct ggcccaccct    1320
cgtgaccacc ctgacctacg gcgtgcagtg cttcagccgc taccccgacc acatgaagca    1380
gcacgacttc ttcaagtccg ccatgcccga aggctacgtc caggagcgca ccatcttctt    1440
```

```
caaggacgac ggcaactaca agacccgcgc cgaggtgaag ttcgagggcg acaccctggt   1500
gaaccgcatc gagctgaagg gcatcgactt caaggaggac ggcaacatcc tggggcacaa   1560
gctggagtac aactacaaca gccacaacgt ctatatcatg gccgacaagc agaagaacgg   1620
catcaaggtg aacttcaaga tccgccacaa catcgaggac ggcagcgtgc agctcgccga   1680
ccactaccag cagaacaccc ccatcggcga cggccccgtg ctgctgcccg acaaccacta   1740
cctgagcacc cagtccgccc tgagcaaaga ccccaacgag aagcgcgatc acatggtcct   1800
gctggagttc gtgaccgccg ccgggatcac tctcggcatg gacgagctgt acaagtaaag   1860
cggccaaatc gtacgcctag gtgatcaaga tctgctagct taattaaccc gggactagtg   1920
cggccgccac cgcggggatc cagacatgat aagatacatt gatgagtttg gacaaaccac   1980
aactagaatg cagtgaaaaa aatgctttat ttgtgaaatt tgtgatgcta ttgctttatt   2040
tgtaaccatt ataagctgca ataaacaagt taacaacaac aattgcattc attttatgtt   2100
tcaggttcag ggggaggtgt gggaggtttt ttcggatcct ctagagtcga ccggaccgct   2160
gcaggcatgc ctgctattgt cttcccaatc ctcccccttg ctgtcctgcc ccaccccacc   2220
ccccagaata gaatgacacc tactcagaca atgcgatgca atttcctcat tttattagga   2280
aaggacagtg ggagtggcac cttccagggt caaggaaggc acggggagg ggcaaacaac   2340 agatggctgg caactagaag gcacagtcga ggtgatcagc gggtttaaac gggccctcta   2400
gtaacggccg ccagtgtgct ggaattcgcc cttcaggcct atgctatcct ctaggcaatg   2460
tgatggtcag ggaaaggggc ccagtgttat gtggctcttt agacactaat cagctggggg   2520
aaaagttcat tggcaaaagt atcctcccag gagtggtctg taccaagtgg agaagacatg   2580
tcactgaagg gagaagggga gccctcatat ccacagtcac tgtgagcgtc cagcaggcaa   2640
gaaggtggtc tcagacaatg gctggatgaa agcaggtttg agatgccag ctctgggatg   2700 aagtcatctt ccaaaggctc tttcttcact gagacaatga attcagggtg atcctcttct   2760
gaagagctta gaggtgcttc ctcaattttc actaccacgt tagtttgact ctctgtctca   2820
gaggggatct ctaaaactag aggcttggtg tatacatggt caaaacgaat gagttcatta   2880
atggcttcca gcttggctga tgaggtcccc actgacagag aaagggaggc tggtaaggaa   2940
ctaggtcctt ctgggtagac ctctgggagt tcctccagac tagcagactc tggggaagga   3000
catttgaaaa acatgacagg gtccaacttg tccagaatgc ccaaaaggat atcagactca   3060
gaatctgaag aggcaacagt gtcagagtcc atgggaagat gttctgggga ggtgacaact   3120
gggcctgcac ctgctgcgga ctcagcagac ccggccacca gccttactcc actcccttg    3180 gcctccacct ctggaaccct gtcaggatcc agcgtgtcca ttcccaagcg tgttcttaac   3240
tcctggttct caaccacaag gccgtgagtt ttctcccgta aaagctgatt ttctagctgg   3300
agtttgtggt tctcttcttc caaatccacc acttgctgct ccagctcgct catccgggct   3360
ttctttctat ctcgagcagt ctgcgctgct actctgtttt tcagtttcct ccgcagcgct   3420
ttctcctccg ggctcaggtg cgtgagccgc tgccgcttgc gagcctgcgg tgtcccgctc   3480
gcctccgacc ctgctgcccg cggacccggt accatgagcg gcagcgcccg gccgccggag   3540
gcgggctggc cagataagag tagcactttg ggggccgccg tggccgcgct cggcgccgct   3600
gccaccacca ccatagccag gaagcttaag tttaaacgct agccagcttg ggtctcccta   3660
tagtgagtcg tattaatttc gataagccag taagcagtgg gttctctagt tagccagaga   3720
gctctgctta tatagacctc ccaccgtaca cgcctaccgc ccatttgcgt caatggggcg   3780
```

-continued

```
gagttgttac gacattttgg aaagtcccgt tgattttggt gccaaaacaa actcccattg    3840
acgtcaatgg ggtggagact tggaaatccc cgtgagtcaa accgctatcc acgcccattg    3900
atgtactgcc aaaaccgcat caccatggta atagcgatga ctaatacgta gatgtactgc    3960
caagtaggaa agtcccataa ggtcatgtac tgggcataat gccaggcggg ccatttaccg    4020
tcattgacgt caataggggg cgtacttggc atatgataca cttgatgtac tgccaagtgg    4080
gcagtttacc gtaaatactc cacccattga cgtcaatgga aagtccctat tggcgttact    4140
atgggaacat acgtcattat tgacgtcaat gggcggggt cgttgggcgg tcagccaggc     4200
gggccattta ccgtaagtta tgtaacgcgg aactccatat atgggctatg aactaatgac    4260
cccgtaattg attactatta ataactagtc aataatcaat gtcaacgcgt atatctggcc    4320
cgtacatcgc gaagcagcgc aaaacgccta accctaagca gattcttcat gcaattgcct    4380
agttcgaagc cacgcgtccg aagggcgaat tgtagataag tagcatggcg ggttaatcat    4440
taactacaag gaacccctag tgatggagtt ggccactccc tctctgcgcg ctcgctcgct    4500
cactgaggcc gggcgaccaa aggtcgcccg acgcccgggc tttgcccggg cggcctcagt    4560
gagcgagcga gcgcgcagag agggacagat ctgccggtct ccctatagtg agtcgtatta    4620
atttcgataa gccaggttaa cctgcattaa tgaatcggcc aacgcgcggg gagaggcggt    4680
ttgcgtattg ggcgctcttc cgcttcctcg ctcactgact cgctgcgctc ggtcgttcgg    4740
ctgcggcgag cggtatcagc tcactcaaag gcggtaatac ggttatccac agaatcaggg    4800
gataacgcag gaaagaacat gtgagcaaaa ggccagcaaa aggccaggaa ccgtaaaaag    4860
gccgcgttgc tggcgttttt ccataggctc cgcccccctg acgagcatca caaaaatcga    4920
cgctcaagtc agaggtggcg aaacccgaca ggactataaa gataccaggc gtttccccct    4980
ggaagctccc tcgtgcgctc tcctgttccg accctgccgc ttaccggata cctgtccgcc    5040
tttctccctt cgggaagcgt ggcgctttct caatgctcac gctgtaggta tctcagttcg    5100
gtgtaggtcg ttcgctccaa gctgggctgt gtgcacgaac cccccgttca gcccgaccgc    5160
tgcgccttat ccggtaacta tcgtcttgag tccaacccgg taagacacga cttatcgcca    5220
ctggcagcag ccactggtaa caggattagc agagcgaggt atgtaggcgg tgctacagag    5280
ttcttgaagt ggtggcctaa ctacggctac actagaagga cagtatttgg tatctgcgct    5340
ctgctgaagc cagttacctt cggaaaaaga gttggtagct cttgatccgg caaacaaacc    5400
accgctggta gcggtggttt ttttgtttgc aagcagcaga ttacgcgcag aaaaaaagga    5460
tctcaagaag atcctttgat cttttctacg ggtctgacg ctcagtggaa cgaaaactca     5520
cgttaaggga ttttggtcat gagattatca aaaaggatct tcacctagat ccttttaaat    5580
taaaaatgaa gttttaaatc aatctaaagt atatatgagt aaacttggtc tgacagttac    5640
caatgcttaa tcagtgaggc acctatctca gcgatctgtc tatttcgttc atccatagtt    5700
gcctgactcc ccgtcgtgta gataactacg atacgggagg gcttaccatc tggccccagt    5760
gctgcaatga taccgcgaga cccacgctca ccggctccag atttatcagc aataaaccag    5820
ccagccggaa gggccgagcg cagaagtggt cctgcaactt tatccgcctc catccagtct    5880
attaattgtt gccgggaagc tagagtaagt agttcgccag ttaatagttt gcgcaacgtt    5940
gttgccattg ctacaggcat cgtggtgtca cgctcgtcgt ttggtatggc ttcattcagc    6000
tccggttccc aacgatcaag gcgagttaca tgatccccca tgttgtgcaa aaaagcggtt    6060
agctccttcg gtcctccgat cgttgtcaga agtaagttgg ccgcagtgtt atcactcatg    6120
gttatggcag cactgcataa ttctcttact gtcatgccat ccgtaagatg cttttctgtg    6180
```

| | | | | |
|---|---|---|---|---|
| actggtgagt | actcaaccaa | gtcattctga | gaatagtgta | tgcggcgacc gagttgctct | 6240 |
| tgcccggcgt | caatacggga | taataccgcg | ccacatagca | gaactttaaa agtgctcatc | 6300 |
| attggaaaac | gttcttcggg | gcgaaaactc | tcaaggatct | taccgctgtt gagatccagt | 6360 |
| tcgatgtaac | ccactcgtgc | acccaactga | tcttcagcat | cttttacttt caccagcgtt | 6420 |
| tctgggtgag | caaaaacagg | aaggcaaaat | gccgcaaaaa | agggaataag gcgacacgg | 6480 |
| aaatgttgaa | tactcatact | cttccttttt | caatattatt | gaagcattta tcagggttat | 6540 |
| tgtctcatga | gcggatacat | atttgaatgt | atttagaaaa | ataaacaaat aggggttccg | 6600 |
| cgcacatttc | cccgaaaagt | gccacctgac | gtctaagaaa | ccattattat catgacatta | 6660 |
| acctataaaa | ataggcgtat | cacgaggccc | tttcgtctcg | cgcgtttcgg tgatgacggt | 6720 |
| gaaaacctct | gacacatgca | gctcccggag | acggtcacag | cttgtctgta agcggatgcc | 6780 |
| gggagcagac | aagcccgtca | gggcgcgtca | gcgggtgttg | gcgggtgtcg ggctggctt | 6840 |
| aactatgcgg | catcagagca | gattgtactg | agagtgcacc | atatggacat attgtcgtta | 6900 |
| gaacgcggct | acaattaata | cataacctta | tgtatcatac | atacgatt taggtgacac | 6960 |
| tatagaactc | gagcagctga | agcttgaatt | catcgatgat | atcagatctg gccactccc | 7020 |
| tctctgcgcg | ctcgctcgct | cactgaggcc | gggcgaccaa | aggtcgcccg acgcccgggc | 7080 |
| tttgcccggg | cggcctcagt | gagcgagcga | gcgcgcagag | agggagtggc caactccatc | 7140 |
| actaggggtt | cctggagggg | tggagtcgtg | acaattcgcc | cttgggccta ggcaattgga | 7200 |
| tccgcc | | | | | 7206 |

<210> SEQ ID NO 2
<211> LENGTH: 1810
<212> TYPE: DNA
<213> ORGANISM: Homo sapiens

<400> SEQUENCE: 2

| | | | | |
|---|---|---|---|---|
| ggcgctgggc | ggctgcggcg | cgcggtgcgc | ggtgcgtagt | ctggagctat ggtggtggtg | 60 |
| gcagccgcgc | cgaacccggc | cgacgggacc | cctaaagttc | tgcttctgtc ggggcagccc | 120 |
| gcctccgccg | ccggagcccc | ggccggccag | gccctgccgc | tcatggtgcc agcccagaga | 180 |
| ggggccagcc | cggaggcagc | gagcgggggg | ctgccccagg | cgcgcaagcg acagcgcctc | 240 |
| acgcacctga | gccccgagga | gaaggcgctg | aggaggaaac | tgaaaaacag agtagcagct | 300 |
| cagactgcca | gagatcgaaa | gaaggctcga | atgagtgagc | tggaacagca agtggtagat | 360 |
| ttagaagaag | agaaccaaaa | acttttgcta | gaaaatcagc | ttttacgaga gaaaactcat | 420 |
| ggccttgtag | ttgagaacca | ggagttaaga | cagcgcttgg | ggatggatgc cctggttgct | 480 |
| gaagaggagg | cggaagccaa | ggggaatgaa | gtgaggccag | tggccgggtc tgctgagtcc | 540 |
| gcagcaggtg | caggcccagt | tgtcacccct | ccagaacatc | tccccatgga ttctggcgt | 600 |
| attgactctt | cagattcaga | gtctgatatc | ctgttgggca | ttctggacaa cttgaccca | 660 |
| gtcatgttct | tcaaatgccc | ttccccagag | cctgccagcc | tggaggagct cccagaggtc | 720 |
| tacccagaag | gacccagttc | cttaccagcc | tccctttctc | tgtcagtggg gacgtcatca | 780 |
| gccaagctgg | aagccattaa | tgaactaatt | cgttttgacc | acatatatac caagccccta | 840 |
| gtcttagaga | taccctctga | gacagagagc | caagctaatg | tggtagtgaa aatcgaggaa | 900 |
| gcacctctca | gcccctcaga | gaatgatcac | cctgaattca | ttgtctcagt gaaggaagaa | 960 |
| cctgtagaag | atgacctcgt | tccggagctg | ggtatctcaa | atctgctttc atccagccac | 1020 |

| | |
|---|---|
| tgcccaaagc catcttcctg cctactggat gcttacagtg actgtggata cgggggttcc | 1080 |
| ctttccccat tcagtgacat gtcctctctg cttggtgtaa accattcttg ggaggacact | 1140 |
| tttgccaatg aactctttcc ccagctgatt agtgtctaag gaatgatcca atactgttgc | 1200 |
| ccttttcctt gactattaca ctgcctgagg atagcagaga agcctgtct gtacttcatt | 1260 |
| caaaaagcca aaatagagag tatacagtcc tagagaattc ctctatttgt tcagatctca | 1320 |
| tagatgaccc ccaggtattg tcttttgaca tccagcagtc caaggtattg agacatatta | 1380 |
| ctggaagtaa gaaatattac tataattgag aactacagct tttaagattg tacttttatc | 1440 |
| ttaaagggt ggtagttttc cctaaaatac ttattatgta agggtcatta gacaaatgtc | 1500 |
| ttgaagtaga catggaattt atgaatggtt ctttatcatt tctcttcccc cttttttggca | 1560 |
| tcctggcttg cctccagttt taggtccttt agtttgcttc tgtaagcaac gggaacacct | 1620 |
| gctgaggggg ctctttccct catgtatact tcaagtaaga tcaagaatct tttgtgaaat | 1680 |
| tatagaaatt tactatgtaa atgcttgatg gaatttttttc ctgctagtgt agcttctgaa | 1740 |
| aggtgctttc tccattttatt taaaactacc catgcaatta aaaggtacaa tgcaaaaaaa | 1800 |
| aaaaaaaaaa | 1810 |

<210> SEQ ID NO 3
<211> LENGTH: 4679
<212> TYPE: DNA
<213> ORGANISM: Adeno-associated virus 2

<400> SEQUENCE: 3

| | |
|---|---|
| ttggccactc cctctctgcg cgctcgctcg ctcactgagg ccgggcgacc aaaggtcgcc | 60 |
| cgacgcccgg gctttgcccg ggcggcctca gtgagcgagc gagcgcgcag agagggagtg | 120 |
| gccaactcca tcactagggg ttcctggagg ggtggagtcg tgacgtgaat tacgtcatag | 180 |
| ggttagggag gtcctgtatt agaggtcacg tgagtgtttt gcgacatttt gcgacaccat | 240 |
| gtggtcacgt tgggtattta agcccgagtg agcacgcagg gtctccattt tgaagcggga | 300 |
| ggtttgaacg cgcagccgcc atgccggggt tttacgagat tgtgattaag gtccccagcg | 360 |
| accttgacga gcatctgccc ggcatttctg acagctttgt gaactgggtg gccgagaagg | 420 |
| aatgggagtt gccgccagat tctgacatgg atctgaatct gattgagcag gcaccctga | 480 |
| ccgtggccga aagctgcag cgcgactttc tgacggaatg cgccgtgtg agtaaggccc | 540 |
| cggaggccct tttctttgtg caatttgaga agggagagag ctacttccac atgcacgtgc | 600 |
| tcgtggaaac caccgggtg aaatccatgg ttttgggacg tttcctgagt cagattcgcg | 660 |
| aaaaactgat tcagagaatt taccgcggga tcgagccgac tttgccaaac tggttcgcgg | 720 |
| tcacaaagac cagaaatggc gccggaggcg ggaacaaggt ggtggatgag tgctacatcc | 780 |
| ccaattactt gctccccaaa acccagcctg agctccagtg ggcgtggact aatatggaac | 840 |
| agtatttaag cgcctgtttg aatctcacgg agcgtaaacg gttggtggcg cagcatctga | 900 |
| cgcacgtgtc gcagacgcag gagcagaaca aagagaatca gaatcccaat tctgatgcgc | 960 |
| cggtgatcag atcaaaaact tcagccaggt acatggagct ggtcgggtgg ctcgtggaca | 1020 |
| agggattac ctcggagaag cagtggatcc aggaggacca ggcctcatac atctccttca | 1080 |
| atgcggcctc caactcgcgg tcccaaatca aggctgcctt ggacaatgcg ggaaagatta | 1140 |
| tgagcctgac taaaaccgcc cccgactacc tggtgggcca gcagcccgtg gaggacattt | 1200 |
| ccagcaatcg gatttataaa attttggaac taaacgggta cgatccccaa tatgcggctt | 1260 |
| ccgtctttct gggatgggcc acgaaaaagt tcggcaagag gaacaccatc tggctgtttg | 1320 |

```
ggcctgcaac taccgggaag accaacatcg cggaggccat agcccacact gtgcccttct   1380
acgggtgcgt aaactggacc aatgagaact ttcccttcaa cgactgtgtc gacaagatgg   1440
tgatctggtg ggaggagggg aagatgaccg ccaaggtcgt ggagtcggcc aaagccattc   1500
tcggaggaag caaggtgcgc gtggaccaga aatgcaagtc ctcggcccag atagacccga   1560
ctcccgtgat cgtcacctcc aacaccaaca tgtgcgccgt gattgacggg aactcaacga   1620
ccttcgaaca ccagcagccg ttgcaagacc ggatgttcaa atttgaactc acccgccgtc   1680
tggatcatga ctttgggaag gtcaccaagc aggaagtcaa agacttttc cggtgggcaa    1740
aggatcacgt ggttgaggtg gagcatgaat tctacgtcaa aaagggtgga gccaagaaaa   1800
gacccgcccc cagtgacgca gatataagtg agcccaaacg ggtgcgcgag tcagttgcgc   1860
agccatcgac gtcagacgcg gaagcttcga tcaactacgc agacaggtac caaaacaaat   1920
gttctcgtca cgtgggcatg aatctgatgc tgtttccctg cagacaatgc gagagaatga   1980
atcagaattc aaatatctgc ttcactcacg gacagaaaga ctgtttagag tgctttcccg   2040
tgtcagaatc tcaacccgtt tctgtcgtca aaaaggcgta tcagaaactg tgctacattc   2100
atcatatcat gggaaaggtg ccagacgctt gcactgcctg cgatctggtc aatgtggatt   2160
tggatgactg catctttgaa caataaatga tttaaatcag gtatggctgc cgatggttat   2220
cttccagatt ggctcgagga cactctctct gaaggaataa gacagtggtg gaagctcaaa   2280
cctggcccac caccaccaaa gcccgcagag cggcataagg acgacagcag gggtcttgtg   2340
cttcctgggt acaagtacct cggacccttc aacggactcg acaagggaga gccggtcaac   2400
gaggcagacg ccgcggccct cgagcacgac aaagcctacg accggcagct cgacagcgga   2460
gacaacccgt acctcaagta caaccacgcc gacgcggagt tcaggagcg ccttaaagaa    2520
gatacgtctt ttgggggcaa cctcggacga gcagtcttcc aggcgaaaaa gagggttctt   2580
gaacctctgg gcctggttga ggaacctgtt aagacggctc cgggaaaaaa gaggccggta   2640
gagcactctc ctgtggagcc agactcctcc tcgggaaccg gaaaggcggg ccagcagcct   2700
gcaagaaaaa gattgaattt tggtcagact ggagacgcag actcagtacc tgaccccag    2760
cctctcggac agccaccagc agcccctct ggtctgggaa ctaatacgat ggctacaggc    2820
agtggcgcac caatggcaga caataacgag ggcgccgacg gagtgggtaa ttcctcggga   2880
aattggcatt gcgattccac atggatgggc gacagagtca tcaccaccag cacccgaacc   2940
tgggccctgc ccacctacaa caaccacctc tacaaacaaa tttccagcca atcaggagcc   3000
tcgaacgaca atcactactt tggctacagc accccttggg ggtattttga cttcaacaga   3060
ttccactgcc acttttcacc acgtgactgg caaagactca tcaacaacaa ctggggattc   3120
cgacccaaga gactcaactt caagctcttt aacattcaag tcaaagaggt cacgcagaat   3180
gacggtacga cgacgattgc caataacctt accagcacgg ttcaggtgtt tactgactcg   3240
gagtaccagc tcccgtacgt cctcggctcg gcgcatcaag gatgcctccc gccgttccca   3300
gcagacgtct tcatggtgcc acagtatgga tacctcaccc tgaacaacgg gagtcaggca   3360
gtaggacgct cttcatttta ctgcctggag tactttcctt ctcagatgct gcgtaccgga   3420
aacaacttta ccttcagcta cacttttgag gacgttcctt tccacagcag ctacgctcac   3480
agccagagtc tggaccgtct catgaatcct ctcatcgacc agtacctgta ttacttgagc   3540
agaacaaaca ctccaagtgg aaccaccacg cagtcaaggc ttcagttttc tcaggccgga   3600
gcgagtgaca ttcgggacca gtctaggaac tggcttcctg gaccctgtta ccgccagcag   3660
```

```
cgagtatcaa agacatctgc ggataacaac aacagtgaat actcgtggac tggagctacc    3720
aagtaccacc tcaatggcag agactctctg gtgaatccgg gcccggccat ggcaagccac    3780
aaggacgatg aagaaaagtt ttttcctcag agcggggttc tcatctttgg gaagcaaggc    3840
tcagagaaaa caaatgtgga cattgaaaag gtcatgatta cagacgaaga ggaaatcagg    3900
acaaccaatc ccgtggctac ggagcagtat ggttctgtat ctaccaacct ccagagaggc    3960
aacagacaag cagctaccgc agatgtcaac acacaaggcg ttcttccagg catggtctgg    4020
caggacagag atgtgtacct tcaggggccc atctgggcaa agattccaca cacggacgga    4080
cattttcacc cctctcccct catgggtgga ttcggactta acaccctcc tccacagatt    4140
ctcatcaaga acacccggt acctgcgaat ccttcgacca ccttcagtgc ggcaaagttt    4200
gcttccttca tcacacagta ctccacggga caggtcagcg tggagatcga gtgggagctg    4260
cagaaggaaa acagcaaacg ctggaatccc gaaattcagt acacttccaa ctacaacaag    4320
tctgttaatg tggactttac tgtggacact aatggcgtgt attcagagcc tcgccccatt    4380
ggcaccagat acctgactcg taatctgtaa ttgcttgtta atcaataaac cgtttaattc    4440
gtttcagttg aactttggtc tctgcgtatt tctttcttat ctagttttcca tggctacgta    4500
gataagtagc atggcgggtt aatcattaac tacaaggaac ccctagtgat ggagttggcc    4560
actccctctc tgcgcgctcg ctcgctcact gaggccgggc gaccaaaggt cgcccgacgc    4620
ccgggctttg cccgggcggc ctcagtgagc gagcgagcgc gcagagaggg agtggccaa    4679

<210> SEQ ID NO 4
<211> LENGTH: 2238
<212> TYPE: DNA
<213> ORGANISM: Mus musculus

<400> SEQUENCE: 4
ctagggtaaa accgtgagac tcggtctgga aatctggcct gagaggacag cctggcaatc      60
ctcagccggg gtggggacgt ctgccgaaga tccttggact ccagcaacca gtggtcgcca     120
ccgtccatcc accctaaggc ccagtttgca cggcggagaa cagctgtgca gccacgctgg     180
acactcaccc cgcccgagtt gagcccgccc ccgggactac aggaccaata agtgatgaat     240
atacccgcgc gtcacggagc accggccaat cgcggacggc cacgacccta gaaaggctgg     300
gcgcggcagg aggccacggg gcggtggcgg cgctggcgta cgtttcct ggctatggtg      360
gtggtggcag cggcgccgag cgcggccacg gcggccccca aagtgctact cttatctggc     420
cagcccgcct ccggcggccg ggcgctgccg ctcatggtac ccggtccgcg ggcagcaggg     480
tcggaggcga gcgggacacc gcaggctcgc aagcggcagc ggctcacgca cctgagcccg     540
gaggagaaag cgctgcggag gaaactgaaa aacagagtag cagcgcagac tgctcgagat     600
agaaagaaag cccggatgag cgagctggag cagcaagtgg tggatttgga agaagagaac     660
cacaaactcc agctagaaaa tcagctttta cgggagaaaa ctcacggcct tgtggttgag     720
aaccaggagt taagaacacg cttgggaatg gacacgctgg atcctgacga ggttccagag     780
gtggaggcca aggggagtgg agtaaggctg gtggccgggt ctgctgagtc cgcagcaggt     840
gcaggcccag ttgtcacctc cccagaacat cttcccatgg actctgacac tgttgcctct     900
tcagattctg agtctgatat ccttttgggc attctggaca agttggaccc tgtcatgttt     960
ttcaaatgtc cttccccaga gtctgctagt ctggaggaac tcccagaggt ctacccagaa    1020
ggacctagtt cctaccagc ctcccttcct ctgtcagtgg ggacctcatc agccaagctg    1080
gaagccatta tgaactcat tcgttttgac catgtataca ccaagcctct agttttagag    1140
```

```
atccoctctg agacagagag tcaaactaac gtggtagtga aaattgagga agcacctcta   1200
agctcttcag aagaggatca ccctgaattc attgtctcag tgaagaaaga gcctttggaa   1260
gatgacttca tcccagagct gggcatctca aacctgcttt catccagcca ttgtctgaga   1320
ccaccttctt gcctgctgga cgctcacagt gactgtggat atgagggctc cccttctccc   1380
ttcagtgaca tgtcttctcc acttggtaca gaccactcct gggaggatac ttttgccaat   1440 gaactttttcc cccagctgat tagtgtctaa agagccacat aacactgggc cccttttccct  1500 gaccatcaca ttgcctagag gatagcatag gcctgtctct ttcgttaaaa gccaaagtag   1560
aggctgtctg gccttagaag aattcctcta agtatttca atctcatag atgacttcca    1620 agtattgtcg tttgacactc agctgtctaa ggtattcaaa ggtattccag tactacagct   1680
tttgagattc tagtttatct taaaggtggt agtatactct aaatcgcagg agggtcatt    1740 tgacagtttt tcccagcct ggcttcaaac tatgtagccg aggctaggca gaaacttctg    1800
accctcttga ccccacctcc caagtgctgg gcttcaccag gtgtgcacct ccacacctgc   1860 cccccgaca tgtcaggtgg acatgggatt catgaatggc ccttagcatt tctttctcca    1920
ctctctgctt cccaggtttc gtaacctgag ggggcttgtt ttcccttatg tgcattttaa   1980
atgaagatca agaatctttg taaaatgatg aaaatttact atgtaaatgc ttgatggatc   2040
ttcttgctag tgtagcttct agaaggtgct ttctccattt attaaaact acccttgcaa    2100 ttaaaaaaaa agcaacacag cgtcctgttc tgtgatttct agggctgttg taatttctct   2160
ttattgttgg ctaaaggagt aatttatcca actaaagtga gcataccact tttaaagtc   2220 aaaaaaaaaa aaaaaaaa                                                  2238

<210> SEQ ID NO 5
<211> LENGTH: 6671
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5
ttggccactc cctctctgcg cgctcgctcg ctcactgagg ccgggcgacc aaaggtcgcc    60
cgacgcccgg gctttgcccg ggcggcctca gtgagcgagc gagcgcgcag agagggagtg   120
gccaactcca tcactagggg ttcctggagg ggtggagtcg tgacaattcg cccttgggcc   180
taggcaattg gatcccggac cgtcgacatt gattattgac tagttattaa tagtaatcaa   240
ttacggggtc attagttcat agcccatata tggagttccg cgttacataa cttacggtaa   300
atggcccgcc tggctgaccg cccaacgacc cccgcccatt gacgtcaata atgacgtatg   360
ttcccatagt aacgccaata gggactttcc attgacgtca atgggtggag tatttacggt   420
aaactgccca cttggcagta catcaagtgt atcatatgcc aagtacgccc cctattgacg   480
tcaatgacgg taaatggccc gcctggcatt atgcccagta catgacctta tgggactttc   540
ctacttggca gtacatctac gtattagtca tcgctattac catggtcgag gtgagcccca   600
cgttctgctt cactctcccc atctcccccc cctccccacc cccaattttg tatttattta   660
ttttttaatt attttgtgca gcgatggggg cgggggggggg ggggggcgc gcgccaggcg   720 ggcggggcg gggcgagggg cggggcgggg cgaggcggag aggtgcggcg gcagccaatc   780
agagcggcgc gctccgaaag tttcctttta tggcgaggcg gcggcggcgg cggccctata   840
aaaagcgaag cgcgcggcgg gcggggagtc gctgcgacgc tgccttcgcc ccgtgccccg   900
```

```
ctccgccgcc gcctcgcgcc gcccgccccg gctctgactg accgcgttac tcccacaggt    960
gagcgggcgg gacggcccct tctcctccgg gctgtaattag cgcttggttt aatgacggct   1020
tgtttctttt ctgtggctgc gtgaaagcct tgaggggctc cgggagggcc ctttgtgcgg   1080
ggggagcggc tcggggggtg cgtgcgtgtg tgtgtgcgtg gggagcgccg cgtgcggctc   1140
cgcgctgccc ggcggctgtg agcgctgcgg gcgcggcgcg gggctttgtg cgctccgcag   1200
tgtgcgcgag gggagcgcgg ccgggggcgg tgccccgcgg tgcgggggg gctgcgaggg    1260 gaacaaaggc tgcgtgcggg gtgtgtgcgt gggggggtga gcaggggtg tgggcgcgtc    1320 ggtcgggctg caaccccccc tgcacccccc tccccgagtt gctgagcacg gcccggcttc   1380
gggtgcgggg ctccgtacgg ggcgtggcgc ggggctcgcc gtgccgggcg ggggtggcg    1440 gcaggtgggg gtgccgggcg gggcggggcc gcctcgggcc ggggagggct cggggaggg    1500 gcgcggcggc ccccggagcg ccggcggctg tcgaggcgcg gcgagccgca gccattgcct   1560
tttatggtaa tcgtgcgaga gggcgcaggg acttcctttg tcccaaatct gtgcggagcc   1620
gaaatctggg aggcgccgcc gcacccctc tagcgggcgc ggggcgaagc ggtgcggcgc    1680
cggcaggaag gaaatgggcg gggagggcct tcgtgcgtcg ccgcgccgcc gtcccttct    1740 ccctctccag cctcggggct gtccgcgggg ggacggctgc cttcgggggg gacggggcag   1800 ggcgggttc ggcttctggc gtgtgaccgg cggctctaga gcctctgcta accatgttca    1860
tgccttcttc ttttcctac agctcctggg caacgtgctg gttattgtgc tgtctcatca    1920
ttttggcaaa gaattcttcg aaagatctgc tagcttaatt aacccggtcg ccaccatggt   1980
gagcaagggc gaggagctgt tcaccggggt ggtgcccatc ctggtcgagc tggacggcga   2040
cgtaaacggc cacaagttca gcgtgtccgg cgagggcgag ggcgatgcca cctacggcaa   2100
gctgaccctg aagttcatct gcaccaccgg caagctgccc gtgccctggc ccaccctcgt   2160
gaccaccctg acctacggcg tgcagtgctt cagccgctac cccgaccaca tgaagcagca   2220
cgacttcttc aagtccgcca tgcccgaagg ctacgtccag gagcgcacca tcttcttcaa   2280
ggacgacggc aactacaaga cccgcgccga ggtgaagttc gagggcgaca ccctggtgaa   2340
ccgcatcgag ctgaagggca tcgacttcaa ggaggacggc aacatcctgg ggcacaagct   2400
ggagtacaac tacaacagcc acaacgtcta tatcatggcc gacaagcaga gaacggcat   2460 caaggtgaac ttcaagatcc gccacaacat cgaggacggc agcgtgcagc tcgccgacca   2520
ctaccagcag aacaccccca tcggcgacgg ccccgtgctg ctgcccgaca accactacct   2580
gagcacccag tccgccctga gcaaagaccc caacgagaag cgcgatcaca tggtcctgct   2640
ggagttcgtg accgccgccg ggatcactct cggcatggac gagctgtaca agtaaagcgg   2700
ccaaatcgta cgcctaggtg atcaagatct gctagcttaa ttaacccggg actagtggcg   2760
gccgctcgag catgcatcta gagggcccta ttctatagtg tcacctaaat gctagagctc   2820
gctgatcagc ctcgactgtg ccttctagtt gccagccatc tgttgtttgc cctcccccg    2880 tgccttcctt gaccctggaa ggtgccactc ccactgtcct ttcctaataa atgaggaaa    2940 ttgcatcgca ttgtctgagt aggtgtcatt ctattctggg gggtggggtg ggcaggaca   3000 gcaaggggga ggattgggaa gacaaatagca ggcatgctgg ggagctagag tcgaccggac   3060
cggtggaagt cctcttcctc ggtgtccttg acttcaaagg gtctctccca tttgcctgga   3120
gagaggggaa ggtgggcatc accaggggtg agtgaaggtt tggaagagtg tagcagaata   3180
agaaaccatg agtcccctcc ctgagaagcc ctgagccccc ttgacgacac acatccctcg   3240
```

```
aggctcagct tcatcatctg taaaaggtgc tgaaactgac catccaagct gccgaaaaag    3300
attgtgtggg gataattcaa aactagagga agatgcagaa tttctacatc gtggcgatgt    3360
caggctaaga gatgccatcg tggctgtgca ttttattgg aatcatatgt ttatttgagg     3420
gtgtcttgga tattacaaat aaaatgttgg agcatcaggc atatttggta ccttctgtct    3480
aaggctccct gccccttgtt aattggcagc tcagttattc atccagggca acattctgc     3540 ttactattcc tgagagcttt cctcatcctc tagattggca ggggaaatgc agatgcctga    3600
gcagcctccc ctctgccata ccaacagagc ttcaccatcg aggcatgcag agtggacagg    3660
ggcctcaggg acccctgatc ccagctttct cattggacag aaggaggaga ctggggctgg    3720
agagggacct gggcccccac taaggccaca gcagagccag actttagct gtgctgactg     3780 cagcctggct tgcctccact gccctccttt gcctcaagag caaggagcc tcagagtgga     3840 ggaagcagcc cctggccttg cctcccacct cccctcccct atgctgtttt cctgggacag    3900
tgggagctgg cttagaatgc cctggggccc ccaggaccct ggcattttaa cccctcaggg    3960
gcaggaaggc agcctgagat acagaagagt ccatcacctg ctgtatgcca cacaccatcc    4020
ccacagttac gtactagttc gaagccacgc gtccgaaggg cgaattgtag ataagtagca    4080
tggcgggtta atcattaact acaaggaacc cctagtgatg gagttggcca ctccctctct    4140
gcgcgctcgc tcgctcactg aggccgggcg accaaaggtc gcccgacgcc cgggctttgc    4200
ccgggcggcc tcagtgagcg agcgagcgcg cagagaggga gtggccaaag atctgccggt    4260
ctccctatag tgagtcgtat taatttcgat aagccaggtt aacctgcatt aatgaatcgg    4320
ccaacgcgcg gggagaggcg gtttgcgtat tgggcgctct ccgcttcct cgctcactga     4380 ctcgctgcgc tcggtcgttc ggctgcggcg agcggtatca gctcactcaa aggcggtaat    4440
acggttatcc acagaatcag gggataacgc aggaaagaac atgtgagcaa aaggccagca    4500
aaaggccagg aaccgtaaaa aggccgcgtt gctggcgttt ttccataggc tccgcccccc    4560
tgacgagcat cacaaaaatc gacgctcaag tcagaggtgg cgaaacccga caggactata    4620
aagataccag gcgtttcccc ctggaagctc cctcgtgcgc tctcctgttc cgaccctgcc    4680
gcttaccgga tacctgtccg cctttctccc ttcgggaagc gtggcgcttt ctcaatgctc    4740
acgctgtagg tatctcagtt cggtgtaggt cgttcgctcc aagctgggct gtgtgcacga    4800
accccccgtt cagcccgacc gctgcgcctt atccggtaac tatcgtcttg agtccaaccc    4860
ggtaagacac gacttatcgc cactggcagc agccactggt aacaggatta gcagagcgag    4920
gtatgtaggc ggtgctacag agttcttgaa gtggtggcct aactacggct acactagaag    4980
gacagtattt ggtatctgcg ctctgctgaa gccagttacc ttcggaaaaa gagttggtag    5040
ctcttgatcc ggcaaacaaa ccaccgctgg tagcggtggt ttttttgttt gcaagcagca    5100
gattacgcgc agaaaaaaag gatctcaaga agatcctttg atcttttcta cggggtctga    5160
cgctcagtgg aacgaaaact cacgttaagg gattttggtc atgagattat caaaaaggat    5220
cttcacctag atccttttaa attaaaaatg aagttttaaa tcaatctaaa gtatatatga    5280
gtaaacttgg tctgacagtt accaatgctt aatcagtgag gcacctatct cagcgatctg    5340
tctatttcgt tcatccatag ttgcctgact ccccgtcgtg tagataacta cgatacggga    5400
gggcttacca tctggcccca gtgctgcaat gataccgcga acccacgct caccggctcc      5460 agatttatca gcaataaacc agccagccgg aagggccgag cgcagaagtg gtcctgcaac    5520
tttatccgcc tccatccagt ctattaattg ttgccgggaa gctagagtaa gtagttcgcc    5580
agttaatagt ttgcgcaacg ttgttgccat tgctacaggc atcgtggtgt cacgctcgtc    5640
```

```
gtttggtatg gcttcattca gctccggttc ccaacgatca aggcgagtta catgatcccc    5700
catgttgtgc aaaaaagcgg ttagctcctt cggtcctccg atcgttgtca gaagtaagtt    5760
ggccgcagtg ttatcactca tggttatggc agcactgcat aattctctta ctgtcatgcc    5820
atccgtaaga tgcttttctg tgactggtga gtactcaacc aagtcattct gagaatagtg    5880
tatgcggcga ccgagttgct cttgcccggc gtcaatacgg gataataccg cgccacatag    5940
cagaacttta aaagtgctca tcattggaaa acgttcttcg gggcgaaaac tctcaaggat    6000
cttaccgctg ttgagatcca gttcgatgta acccactcgt gcacccaact gatcttcagc    6060
atcttttact ttcaccagcg tttctgggtg agcaaaaaca ggaaggcaaa atgccgcaaa    6120
aaagggaata agggcgacac ggaaatgttg aatactcata ctcttccttt ttcaatatta    6180
ttgaagcatt tatcagggtt attgtctcat gagcggatac atatttgaat gtatttagaa    6240
aaataaacaa atagggggttc cgcgcacatt tccccgaaaa gtgccacctg acgtctaaga    6300
aaccattatt atcatgacat taacctataa aaataggcgt atcacgaggc cctttcgtct    6360
cgcgcgtttc ggtgatgacg gtgaaaacct ctgacacatg cagctcccgg agacggtcac    6420
agcttgtctg taagcggatg ccgggagcag acaagcccgt cagggcgcgt cagcgggtgt    6480
tggcgggtgt cggggctggc ttaactatgc ggcatcagag cagattgtac tgagagtgca    6540
ccatatggac atattgtcgt tagaacgcgg ctacaattaa tacataacct tatgtatcat    6600
acacatacga tttaggtgac actatagaac tcgagcagct gaagcttgaa ttcatcgatg    6660
atatcagatc t                                                         6671
```

METHOD FOR GENETIC TREATMENT USING THE AAV-XBP1S/GFP VIRUS AND USE THEREOF IN THE PREVENTION AND TREATMENT OF AMYOTROPHIC LATERAL SCLEROSIS

SEQUENCE LISTING

The instant application contains a Sequence Listing which has been submitted electronically in ASCII format and is hereby incorporated by reference in its entirety. Said ASCII copy, created on Sep. 10, 2018, is named 46788-0002US1_SL.txt and is 30,574 bytes in size.

TECHNICAL FIELD OF THIS INVENTION

This invention is applied in the field of medicine, specifically in the prevention and treatment of neurodegenerative diseases, preferably amyotrophic lateral sclerosis (ALS), through the use of adeno-associated viruses (AAV) that over-express the transcription factor XBP1s in neurons of the central nervous system (CNS), preferably in motor neurons and the spinal cord, improving the adaptation capacity of the neurons and preventing the development of ALS.

BACKGROUND INFORMATION AND DESCRIPTION OF THE STATE OF THE ART

Scientific research on the diseases of the central nervous system has been of great interest in recent years, especially the diseases related to motor alterations. At present, the treatment of diseases related to motricity does not have genetic therapeutic approaches to diminish the symptoms. One of the most characteristic motor neurodegenerative diseases is amyotrophic lateral sclerosis (ALS). This progressive disease affects the motor nerve cells in the brain and the spinal cord which leads to paralysis and death. The misfolding and aggregation of the protein superoxide dismutase 1 (SOD1) is associated with the appearance of sporadic and familiar forms of ALS. Although the principal mechanism responsible for the progressive loss of the motor nerve cells in ALS continues being unknown, the latest evidence highlights the contribution of the alterations of the proteostasis or the protein equilibrium at the level of quantity and quality in the process of the disease. One of the events detected at an early pre-symptomatic stage of ALS in mouse models is the presence of stress response proteins in the endoplasmic reticulum (ER) of the secondary motor neurons.

The stress in the endoplasmic reticulum (ER) is buffered by the activation of the unfolded protein response (UPR), a homeostatic signaling network that orchestrates the recovery of the function of the organelle. On the other hand, the lack of adaptation to stress of the ER results in neuronal disfunction and apoptosis. UPR signaling relies upon regulation/activation of three principal transcription factors known as X-box binding protein 1 (XBP1), a factor that activates transcription 6 (ATF6) and transcription factor 4 (ATF4). Together, XBP1s, ATF6 and ATF4 allow the adaptation to stress, or in the case of ATF4 towards the elimination of cells that have been irreversibly damaged by apoptosis.

The pharmacological and genetic therapies that exist today are aimed mainly at the capacity of cellular adaptation, to reestablish the proteostasis of the endoplasmic reticule (ER) through gene expression of UPR. These studies have been carried out in preclinical models of neurodegenerative diseases with successful results.

Gene therapy using recombinant viruses is being used in our laboratory as an attractive strategy to deliver the components of the active UPR for specific areas of the brain. This method can also avoid the possible pleiotropic effects of the systemic and chronic administration of compounds with the objective of controlling ER stress. The adeno-associated viruses (AAV) are one of the options for the administration of therapeutic genes in the brain and the spinal cord due to their safety profile, as has been shown in clinical tests.

The research and development pipeline for treatment and/or prevention of ALS is broad ranging from small molecule compounds (e.g. derivation of 1,3-benzoathyazol, such as Riluzol) that can aid in delaying time to assisted ventilation by blocking of sodium channels sensitive to tetrodotoxin (Rilutek™) to genetic approaches like IGF-1 (Insulin growth factor-1) through the virus AAV4 (associated adenovirus serotype 4) made known in the document EP 2489733 A2; or the construct HIF11-alfa (inducible factor of hypoxia 1, subunit alfa) and a general adeno-associated virus made known in the document EP 2497500 A1, among others.

Part of this patent is the information contained, in its most varied range, in patent application CL 3590-2014. The previously mentioned patent application disclosed a XBP1s-containing AAV for the improvement of the memory, specifically in neuronal cells of the hippocampus, without being restrictive to only this specific sequence of XBP1. There are biological deposits of the plasmid pAAV-XBP1s-HA dated 5 Nov. 2014 in the international agency of biological deposits, American Type Culture Collection (ATCC), under deposit number PTA-121708.

SUMMARY OF THE INVENTION

Amyotrophic lateral sclerosis (ALS) occurs as a result of motoneurons loss in the central nervous system and consequently the loss of locomotive capacity. The invention relates to the expression of a new gene in different regions of the brain, but mostly in the frontal cortex of the brain and spinal cord, where the misfolding and aggregation of SOD1 and other proteins occur. ER stress resulting from the above appears as an early event in the asymptomatic stage of the disease. Endogenous ER stress-mediated activation of the UPR is insufficient to grant cellular protection, therefore these motoneurons die. This mechanism has been indicated as one of the main ones in correcting the protein folding function of the ER among many other factors involved. In the search for different regulators of the expression of UPR, XBP1s was one of three functional activators identified as a key response component against misfolded proteins.

Surprisingly, overexpression of XBP1s in the CNS in transgenic mice (as ALS animal model) through direct viral-mediated delivery (intracerebroventricular) achieves an increase in the survival of these ALS mouse models (increasing the pre-symptomatic stage), without attenuation of the symptomatic stage of the disease.

A relevant fact in this invention is the degree of homology in the XBP1 sequences in mice and humans that is over 75%, preferably 83%. The XBP1s sequences of mice and XBP1s of human can be seen in table numbers IV and II, respectively.

A first aspect of the present invention relates to a method for delaying ALS. The invention is characterized in that it is not to be limited to symptomatic stage ALS in mammals, preferably in humans, using a virus that induces the neuronal overexpression of XBP1s in the brain, preferably in the frontal cortex of the brain and spinal cord.

A second aspect of this invention provides a therapeutic treatment method to delay the symptomatic stage of ALS in mammals, preferably in humans. The method comprises the intravenous and/or intraperitoneal and/or intracranial and/or intramedullary and/or intranasal and/or intraneural and/or intracerebroventricular administration and/or any means that will introduce the virus into the brain passing the blood-brain barrier of a patient or subject.

The virus induces the neuronal overexpression of XBP1s in a dose range of $1^6$ to $1^{30}$ viral units per individual.

A third aspect of this invention is related to a method to reduce SOD1 protein aggregation in mammals, preferably in humans, utilizing a virus that induces the overexpression of XBP1s in the CNS, preferably in the front cortex of the brain and spinal cord.

A fourth aspect of this invention is the use of an AAV virus that permits stable transduction and therefore sustained overexpression of XBP1s, which becomes an effective medicine and that avoids repetitive administrations, with the purpose of delaying the symptomatic stage of ALS in mammals, preferably in humans.

This patent also presents the sequence of the plasmid with the fragment of nucleic acid of the virus and an insert with a nucleotide sequence described in Table I or any variant of this fragment that encodes and overexpresses the neuronal transcription factor XBP1, preferably human XBP1s, just like the sequence described in table II.

DETAILED DESCRIPTION OF THE INVENTION

It must be understood that this invention is not limited to the particular methodology, compounds, materials, manufacturing techniques, uses and applications described herein, because these can vary. It must also be understood that the terminology employed herein is used with the only purpose of describing a particular representation and does not attempt to limit the perspective and potential of this invention.

It must be noted that the use and method, herein, in the list of claims and in the entire text that the singular does not exclude the plural, unless the context clearly implies it. Then, for example, the reference to a "use or method", is a reference to one or more uses or methods and includes equivalents known to those who know the subject (the art). Similarly, as another example, the reference to "a step", "a stage" or "a method" is a reference to one or more steps, stages or methods and can include sub steps, stages or methods, implied and/or supervening.

All the conjunctions used must be understood in their least restrictive and most inclusive sense possible. Thus, for example, the conjunction "or" must be understood in its orthodox logical sense and not as an "exclusionary or", unless the text specifically needs or indicates it. The structures, materials and/or elements described must be understood to refer also to those equivalents functionally and thus avoid interminable restrictive enumerations.

The expressions used to indicate approximations or conceptualizations must be understood thus, except if the context demands a different interpretation.

All the names and technical and/or scientific terms employed herein have the common meaning that a common person, qualified in these matters, gives them, unless otherwise indicated.

The methods, techniques, elements, compounds and compositions are described although methods, techniques, compounds and compositions, similar and/or equivalent to those described can be used or preferred in practice and/or tests of this invention.

All the patents and other publications are incorporated herein as references, with the purpose of describing and/or informing, for example, the methodologies described in those publications that might be useful in relation to this invention.

These publications are included only for their information prior to the registration date of this patent application.

In this respect, nothing must be considered as an admission or acceptance, rejection or exclusion, that the authors and/or inventors are not entitled to do so, or that those publications are pre-dated pursuant to other prior ones, or for any other reason.

This invention describes adeno-associated virus based on the serotypes AAV1, AAV2, AAV3, AAV4, AAV5, AAV6, AAV7, AAV8, AAV9, AAV10, AAV11, including pseudo-typed AAVs capable of mediating, in an efficient manner, the transference of genes to the brain, preferably to motor nerve cells when locally administered.

The systemic administration of these vectors also leads to efficient gene delivery to both the brain and the motor neurons. Although the delivery of genes mediated by the AAV2 vector is more efficient, delivery in the case of systemic administration is not restricted to only the brain or the motor neurons. This invention features an AAV2 flanking the transcription factor promoter and XBP1s for generation of response in a cluster of factors in non-specific form of interest in the brain and specifically in the motor nerve cells. Particularly, the local administration of the AAV2 vector that includes an expression cassette in which the encoded expression of XBP1s can be under the control of one or several promoters within the group cmv, Pgk 1, CamKII and Thy 1, ChAT, cva, among others, preferably the promoter of cytomegalovirus cmv, as observed with the addition of the reporter green fluorescent protein (GFP), which can be found regulated by the promoter regions such as EF-1α, Pgk 1, cmv, cba, CamKII and Thy 1, preferably EF-1α, achieves a delay in the symptomatic appearance of ALS through the improvement in motor nerve cells of the nervous system in healthy individuals in vivo. This region encoding the GFP protein can exist, just as another non-coding random nucleotide region or a sequence of DNA Scramble (DNA of negative control) might exist.

On the other hand, the AAV vector of serotype 2 (AAV2) is the genetic material mechanism that allows for white tissue specificity, such as the motoneurons associated with failure in ALS.

I. Definition of Terms and General Expressions

The words "adeno-associated virus", "AAV virus", "AAV virion", AAV viral particle" and "AAV particle" as used in this document are interchangeable, they refer to a viral vector consisting of at least one protein of the AAV capsid (preferably through all the proteins of the capsid of an AAV serotype in particular) and a polynucleotide of the encapsidated genome of AAV. If the particle consists of a heterologous polynucleotide (that is, a polynucleotide other than a native type AAV genome such as a transgene to be delivered to a mammal's cell) flanked by the inverted terminal repetitions of the AAV, that is typically referred to as a "vector of AAV particles" or "AAV vector". AAV refers to a virus that belongs to the Dependovirus genre of the Parvoviridae family. The AAV genome is of approximately 4.7 kilobases in length and is made up of single-stranded deoxyribonucleic acid (ssDNA) that can be positive or negative sense. The genome consists of inverted terminal repetitions (ITR) at both ends of the DNA strand, and two open reading frames (ORFs): REP and CAP (Replicase and Capsid). The REP framework is formed by four superimposed genes that encode REP proteins (REP 78, REP 68, REP 52 and REP 40) required for the life cycle of the AAV. The CAP framework contains overlapping nucleotides of 20 sequences encoding proteins of the capsid: VP1, VP2 and VP3, that interact with each other to form a capsid with an icosahedral symmetry.

At present about 11 serotypes of AAVs of humans have been described and about 100 AAVs of primates that can be used as vectors. Each serotype represents advantages and disadvantages regarding stability, productivity, immunogenicity, bioavailability, tropism, etc. Nevertheless, many laboratories have developed pseudo-typed vectors, that is, modified AAVs that contain surface proteins of different serotypes, to thus obtain the advantages of different serotypes and avoid the disadvantages of some surface proteins of some serotypes.

The term "adeno-associated virus ITR" or "AAV ITR", as it is used herein, refers to the inverted terminal that is repeated and is present at both ends of the DNA strand of the genome of an adeno-associated virus. The ITR sequences are required for the efficient expression of the AAV genome. Another characteristic of these sequences is their capacity to form a complementary strand. This characteristic contributes to their auto-copy that permits the independent primary synthesis of the second strand of DNA. The ITRs also showed to be necessary for both the integration of the native type AAV of the DNA in the genome of the host cell and of its rescue, and for the efficient encapsidation of the DNA of the AAV combined with the generation of its complete assembly.

The term "AAV2", as used in this invention, refers to the serotype 2 of the adeno-associated virus with a genome sequence as defined in the GenBank access number: AF043303.1

The term "AAV vector", as used in this invention, also refers to a vector that consists of one or more polynucleotides of interest (or transgenes) that are flanked by terminal repetition sequences of AAV (ITRs). These AAV vectors can be replicated and packaged in infectious viral particles when they are present in a host cell that has been transfected with a vector that encodes and expresses the REP and CAP genes (that is, the AAV REP and CAP proteins), and where the host cell has been transfected with a vector that encodes and expresses a protein of the adenovirus reading frame E4orf6. When an AAV vector is incorporated into a larger polynucleotide (for example, in a chromosome or in another vector such as a plasmid utilized for cloning or transfection), then the AAV vector is named typically as a "pro-vector". The pro-vector can be "rescued" by replication and encapsidation in the presence of the packaging functions of the AAV and the necessary auxiliary functions provided by E4orf6.

The words "specific binding site for the transcription regulating region of XBP1" as used in this invention, refers to a sequence of nucleic acids that serve as a promoter (that is, regulates the expression of a selected nucleic acid sequence, operationally bound to the promoter) and that affects the expression of a selected nucleic acid sequence in cells of specific tissues, such as the nerve cells. The specific binding site for the regulating region of the transcription of neuronal tissue can be constitutive or inducible.

The words "CAP gene" or "CAP of AAV gene", as used in this invention, refer to a gene that encodes a CAP protein. The words "CAP protein", as used herein, refers to a polypeptide that has activity of at least one functional activity of the CAP protein of a native AAV (VP1, VP2, VP3). Examples of functional activities of the VP1, VP2 and VP3 proteins include the capacity to induce the formation of a capsid, facilitate the accumulation of single-stranded DNA, facilitate the packaging of the DNA of AAV in the capsid (that is, the encapsidation), join cell receptors and facilitate the entry of the virion into a host.

The term, "capsid", as used in this invention, refers to the structure in which the viral genome is packaged. A capsid consists of an oligomeric structure with structural subunits of CAP proteins. For example, the AAV has an icosahedral capsid formed by the interaction of three proteins of the capsid: VP1, VP2 and VP3.

The words "composition of cells", as used in this document, refer to a compound type material that consists of the cells of the invention and at least another component. The composition may be formulated as a single formulation or can be presented as separate formulations of each one of the components, which can be combined for joint use as a combined preparation. The composition can be a kit of parts, where each one of the components is formulated and packaged individually.

The words "constitutive promoter", as used in this invention, refer to a promoter whose activity is maintained at a relatively constant level throughout an entire organism, or during most of the experimental stages, with little or no impact by the environmental and external conditions of the cell.

The word "enhancer", as used herein, refers to an element of the DNA sequence to which the transcription factors are bound, to increase the transcription of the genes.

The words "expression cassette", as used herein, refer to a construction of nucleic acids generated by recombination or synthetically, with a series of specific elements of the nucleic acids, that permit the transcription of a particular nucleic acid, in a target cell.

The words "genes that provide help functions", as used herein, refer to genes that encode polypeptides, that execute functions on which the AAV is dependent for replication (that is, "help functions"). The auxiliary functions include those functions that are necessary for AAV replication, including those fragments involved in the activation of AAV gene transcription, the specific stages of the splicing of mRNA of AAV, the replication of the DNA of AAV, the synthesis of the products of CAP and the assembly of the AAV capsid. Accessory viral functions can be derived from any of the known auxiliary viruses such as adenovirus, herpes virus, lentivirus and the vaccinia virus. The auxiliary functions include, without limitation, lentivirus WHV.

The words "operationally united" as described in this document, refer to the functional relationship and localization of a promoter sequence regarding a polynucleotide of interest (for example, a promoter or enhancer operationally linked to a coding sequence that affects the transcription of this sequence). Generally, an operationally linked promoter is contiguous to the sequence of interest. Nevertheless, an enhancer does not have to be contiguous to the sequence of interest to control its expression.

The words "administrated locally", as used herein, means that the polynucleotides, vectors, polypeptides and/or pharmaceutical compositions of the invention are administrated to the subject on or close to a specific site.

The words "pharmaceutically acceptable carriers", "pharmaceutically acceptable diluents", "pharmaceutically acceptable excipients" or "pharmaceutically acceptable vehicle", are interchangeable in this document, they refer to a non-toxic solid, semisolid, or filling fluid, diluent or encapsulation material or an auxiliary formulation for any conventional type. A pharmaceutically acceptable carrier is essentially nontoxic for the containers used in the doses and concentrations and is compatible with other ingredients of the formulation. The number and nature of the pharmaceutically acceptable vehicles depends on the form of administration desired. The pharmaceutically acceptable vehicles are known and can be prepared by methods well known in the art.

The word "promoter", as used herein, refers to a region of nucleic acid that functions to control the transcription of one or more polynucleotides, situated upstream from the sequence of the polynucleotide(s), and that is identified structurally by the presence of a DNA binding site dependent on the RNA Polymerase, the transcription initiation sites, and any other DNA sequence, including, but not limited to the binding sites of transcription factors, repressor, and activating protein binding sites and any other sequences of nucleotides known in the art to act directly or indirectly to regulate the amount of transcription as of the promoter. A "specific tissue" promoter is only activated in specific types of cells or differentiated tissues.

The word "polynucleotide", as used herein, refers to a molecule of nucleic acid, either DNA or RNA, that contains deoxyribonucleotides or ribonucleotides respectively. The nucleic acid can be double stranded, single stranded, or contain both double stranded or single stranded sequences. The word "polynucleotide" includes, but is not limited to, sequences of nucleic acids with the capacity to encode a polypeptide and sequences of nucleic acids partially or totally complementary to an endogenous polynucleotide of the cell or the subject treated with the same so that, after its transcription, it generates a molecule of RNA (for example, microRNA, shRNA, siRNA) able to hybridize and inhibit the expression of the endogenous polynucleotide.

In this document the word "strand" refers to a sequence of continuous nucleotides (including or not including modified natural nucleotides or non-natural). The two or more strands can be, or each one forms a part of separate molecules, or they can be covalently interconnected, for example, by means of a coupler, for example a linker like polyethylene glycol, to form a molecule. At least one of the strands can include a region that is sufficiently complementary to a target RNA.

A second strand of the agent of dsRNA that comprises a region complementary to the antisense strand, is named the "sense strand". Nevertheless, a siRNA agent can also be formed based on a single molecule of RNA that is at least partially self-complementary, forming, for example, a fork or eyelet structure that includes a duplex region. The latter are named RNA short fork or shRNAs. In this case, the word "strand" refers to one of the regions of the RNA molecule that is complementary to another region of the same molecule of RNA.

The term "post-transcriptional regulating region", as used herein, refers to any polynucleotide that facilitates the expression, stabilization or localization of the sequences contained in the resulting cassette or gene product.

The words "recombinant viral genome", as used here, refer to an AAV genome in which at least one cassette of polynucleotide is inserted in the viral genome, wherein the at least one cassette of polynucleotide is unrelated to the expression of the native AAV genome.

The words "rep gene" or "rep gene of AAV", as used herein, refer to a gene that encodes a Rep protein. The words "Rep protein", as used here, refer to a polypeptide that has at least one functional activity of a native Rep protein of AAV (for example, Rep 40, 52, 68, 78). A "functional activity" of a Rep protein (for example Rep 40, 52, 68, 78) is any activity associated to the physiological function of the protein, including the facilitation of the replication of the DNA through the recognition, binding and cutting of the origin of the replication of the DNA of AAV, as well as the helicase activity of DNA. The additional functions include modulation of the transcription of AAV (or other heterologous) promoters and the site-specific integration of the DNA of AAV in a chromosome of the host.

The term "subject", as used herein, refers to an individual, plant, mammal or animal, such as a human, a non-human primate (for example, chimpanzee or other ape and species of monkey), an animal (for example, birds, fish, livestock, sheep, pigs, goats and horses), a mammal (for example, dogs and cats) or a laboratory animal (for example rodents, such as rats, mice, mice with silenced genes (knockout mice), mice that overexpress a gene (transgenic mice) and Guinea pigs). The word does not denote a particular age or sex. The word "subject" includes an embryo and a fetus.

The words "administrated systemically" and "Systemic administration", as used in this document, mean that the polynucleotides, vectors, polypeptides or pharmaceutical compositions of this invention are administrated to a subject in a non-localized manner. The systemic administration of the polynucleotides, vectors, polypeptides or pharmaceutical compositions of the invention can reach various organs or tissues of the subject's entire body or can reach new specific organs or tissues of the subject. For example, the intravenous administration of a pharmaceutical composition of the invention may result in the transduction in more than one tissue or organ in a subject.

The words "transcriptional regulatory region", as used herein, refer to a fragment of nucleic acid able to regulate the expression of one or more genes. The regulating regions of the polynucleotides of the invention include a promoter and optionally an enhancer.

The word "transduction", as used herein, refers to the process whereby a sequence of foreign nucleotides is introduced within the cell in a viral vector.

The word "transfection", as used in this document, refers to the introduction of DNA in the recipient eukaryotic cells.

The word "vector" as used herein, refers to a construct able to deliver, and optionally express, one or more polynucleotides of interest in a host cell. The examples of vectors include, but are not limited to, viral vectors, DNA or naked RNA expression vectors, plasmid, cosmid or phage vectors, expression vectors or RNA or DNA associated with agents of cationic condensation, expression vectors of DNA or RNA encapsulated in liposomes, and certain eukaryote cells, such as production cells. The vectors may be stable and may be self-replicating. There are no limitations regarding the type of vector that may be used. The vector may be a cloning vector, adapted for the propagation and obtaining of polynucleotides, genic constructions or expression vectors incorporated into various heterologous organisms. The adapted vectors include prokaryote expression vectors, phages and shuttle vectors and eukaryote expression vectors based on viral vectors (for example, adenovirus, adeno-associated virus as well as retrovirus and lentivirus) as well as non-viral vectors such as pSilencer 4.1-CMV.

The methods and compositions of the invention, for example the methods and compositions of the AAV virus with the XBP1s-GFP insert, can be used with any dosage and/or formulation described in this invention, as well as with any means of administration described in this invention.

The "siRNA agents" or "siRNA" are words used to describe duplex fragments of RNA from between 15 and 25 base pairs, preferably from 19 to 21 base pairs in length.

The word "cDNA" or "complementary DNA" refers to a sequence of DNA totally complementary to a RNA, from which it is synthetized by RT-PCR.

As used in this document, the word "complementary" is used to indicate a sufficient degree of complementarity such that a stable and specific union takes place between a compound and a molecule of target RNA; the specific union requires a sufficient degree of complementarity to avoid the non-specific binding of the oligomeric compound to non-objective sequences in conditions in which the specific union is desired, that is, in physiological conditions in the case of tests in vivo or therapeutic treatment, or in the case of in vitro tests, under conditions in which the tests have been carried out.

Ligands

The characteristics of a virus, including its pharmacological characteristics, can be influenced and made to measure, for example, by the introduction of ligands. Additionally, the pharmacological characteristics of a viral agent can be improved by the incorporation of a ligand in a formulation of the agent and a virus.

The ligands can be joined to a broad variety of entities, for example, ligands that are joined to a viral agent, or they can be used as a conjugate or additive of formulation, for example, with the vehicle of a monomeric subunit conjugated with the ligand. The examples are described below in the context of a monomeric subunit conjugated with ligand, but that is only the preferred embodiment, and the entities can be coupled with a virus at other points.

A ligand alters the distribution, direction or life cycle of a viral agent in which it is incorporated. In the preferred embodiments, a ligand provides a better affinity for a selected target, for example, a molecule, cell or type of cell, a compartment, for example a cellular compartment or organ, a tissue or region of the body, for example, by how it compares with a species in which this ligand is absent.

The ligands can improve the characteristics of transport, hybridization and specificity of the target molecule, for this invention, of the virus.

In general, ligands can include therapeutic modifiers, for example, to improve the absorption of the molecule in the individual; diagnostic compounds or reporter groups, for example, to monitor the distribution; crosslinking agents; fractions that confer resistance to immune reactions; and natural or unusual nucleobases.

The general examples include lipophilic molecules, lipids, lectins (for example, hecogenin, diosgenin), terpenes (for example, triterpenes, for example sarsasapogenin, friedelin, lithocholic acid derived from epifriedelanol), vitamins, carbohydrates (for example, a dextran, pullulan, chitin, chitosan, synthetic polymers (for example oligo-lactate 15-mer) and natural polymers (for example, of low and medium molecular weight, inulin, cyclodextrin or hyaluronic acid), proteins, protein binding agents, integrin targeting molecules, polycations, peptides, polyamines and peptide mimetics. Other examples include the receptor ligands of epithelial cells or of folic acid, such as transferrin.

The ligand can be a molecule that is present naturally or recombinant or synthetic, such as a synthetic polymer, for example, a synthetic polyaminoacid. The examples of the polyaminoacids include polylysine (PLL), poly L-aspartic acid, poly L-glutamic acid, copolymer of styrene-anhydride of maleic acid, copolymer of poly-(lactic-co-glycolic), copolymer of divinyl ether-maleic anhydride, copolymer of N-(2-hydroxi-propyl)-methacryl-amide (HMPA), polyethylene glycol (PEG), polyvinyl-vinylic alcohol (PVA), polyurethane, poly-(2-ethyl-acrylic acid), polymers of N-isopropyl-acryl-amide or polyphosphazine. The examples of the polyamines include: polyethylene amine, poly lysin (PLL), spermine, spermidine, polyamine, pseudo-peptide polyamine, peptidomimetic polyamine, polyamine of dendrimer, arginine, amidine, protamine, cationic fractions, for example cationic lipid, cationic porphyrin, quaternary salt of a polyamine or an alpha-helicoidal peptide.

The ligands can also include steering groups, for example, a steering agent to a cell or tissue, for example a thyrotropin, melanotropin, surfactant protein A, carbohydrate of mucin, a glycosylated polyamine acid, bisphosphonate, polyglutamate, poly aspartate, or a peptide of Arg-Gly-Asp (RGD), or a mimetic of peptide of RGD.

The ligands can be proteins, for example, glycoproteins, lipoproteins, for example, low density lipoprotein (LDL), or albumins, for example, serum albumin or peptides, for example, molecules that have a specific affinity for a co-ligand or antibodies, for example, an antibody that binds with a specified type of cell. The ligands can also include hormones and hormone receptors. They can also include non-peptide species, such as cofactors, multivalent lactose, multivalent galactose, N-acetyl-galactosamine, N-acetyl-glucosamine, multivalent mannose or multivalent fucose.

The ligand can be a substance, for example, a drug that can increase the absorption of the viral agent within the cell, for example, through the alteration of the cytoskeleton of the cell, for example, through the alteration of microtubules, microfilaments and/or intermediate filaments of the cell.

In one aspect, the ligand is a lipid, or a lipid-based molecule. This lipid or preferably this lipid-based molecule is linked with a serum protein, for example, albumin serum.

In an alternative modality the virus will be packaged.

For the preparation of the injectable solutions of the virus, the solutions are prepared by diluting the concentration of the necessary virus in PBS (phosphate buffered saline) whose formulation is the following:

PBS 1×

1. Dissolve the viral dose in 800 ml of distilled water with:
   8 g of NaCl
   0.2 g of KCl
   1.44 g of $Na_2HPO_4$
   0.24 g of $KH_2PO_4$
2. Adjust the pH to 7.4 with HCl.
3. Adjust the volume to 1 L with distilled water additional $H_2O$.
4. Sterilize and autoclave.

Design and Selection

The control of the protein synthesis and the induction of the gene expression is the key for the treatment of ALS.

The word "ALS", as used herein, is a disease that affects motor neurons in a fatal manner generating a progressive damage in the brain and in the spinal cord (1). Mostly, this disease is presented sporadically (sALS); only 10% of the cases have a family genetic etiology (fALS) caused by multiple variants in the genes (2). Genetically, the more common causes of the fALS are the expansion by repetition of a hexanucleotide in the intronic region of C9orf72 and mutations in the genes such as the superoxide dismutase (SOD1) (3). ALS disease appears mostly in adults, where the symptomatic period is brief. Apparently, the appearance of disorders of the ER and their proteostasis are the basis for the generation of the disease (4).

The words "endoplasmatic reticule (ER)" are considered as a compartment implicated in the folding of proteins and of their quality control (5). A series of stress markers that occur in the ER have been reported and this has been related with the incidence of ALS in humans and transgenic animal models (6) and is one of the first events that are detected before ALS is symptomatic (7). The unfolded protein response (UPR) has been manipulated pharmacologically and genetically with the purpose of facing the stress of the ER and favorable and functional consequences have been proven in the control of ALS. (8-10)

The unfolded protein response (UPR) is triggered mainly by three stress sensors IRE 1, PERK and ATF6.

IRE 1 is a protein with kinase and endoribonuclease activity, which, after its activation catalyzes the cut and splicing of mRNA that encodes a X-Box transcriptional protein binding factor (XBP1) converting it into a powerful activator of numerous UPR-sensitive genes known as XBP1s (11). For its part, XBP1s is involved in the control of the expression of genes that control the folding, secretion, protein quality control and degradation by the ER (ERAD) (12, 13).

On the other hand, the activation of PERK also triggers the inhibition of the translation of the proteins in the ER and thus a reduction of the load on the ER of poorly folded proteins. On its part, PERK triggers the expression of ATF4 which, in situations of prolonged stress in the ER generates a pro-apoptotic effect. (14. 15)

Finally, after the stress episodes of the ER, ATF6 is transported to the Golgi, where an ATF6f cytosolic fragment that operates as a transcription factor regulating the ERAD genes is split and liberated (5, 6). In other words, the control of these three transcription factors has unique responses on UPR where they affect cellular life or death. (17)

The relationship of the stress of the ER and the ALS disease (fALS and sALS) has been seen in post-mortem studies in humans where the activation of UPR has been identified (18 to 22). Transcription factors XBP1 and ATF4 in the spinal cord of patients with ALS have also been described (23). On the other hand, in animal models with fALS the presence of ER stress has been observed (9, 24 to 33). The therapeutic potential of UPR as a target for the treatment of ALS is not clear yet. An analysis of laser dissection to a group of dead neurons early in the course of the disease and to another group of neurons resistant to neurodegeneration (7), showed that only the motoneurons of fALS were affected in mouse models that were selectively prone to chronic stress of the ER, converting ER stress as one of the molecular markers detected earlier, including prior to the denervation in pre-symptomatic animals. On the other hand, it has been proven that cultures of human motor neurons generated from iPS cells derived from patients with fALS carriers of a SOD1 mutation generate stress spontaneously in the ER as a response to an altered physiological activity (34). Alterations in the proteostasis are also seen in motor neurons derived from iPSC from patients that express the C9orf72 mutation (the most common of the fALS) (34). Finally, these studies suggest that a misfolding of proteins is an outstanding characteristic in neurons of patients with ALS (35).

During the present invention, a knockout mouse model was developed to investigate and test the role of XBP-1 in the motor nervous system related to ALS. Here, the suppression of UPR transcription factor would be expected to increase the severity of ALS; however, surprisingly the opposite was observed in experimental ALS due to the alteration to the stress adaptation given the folding of proteins. It was observed that these mice were more resistant to developing the disease, which suggested that this effect was given as a compensatory effect on the proteostasis network that enhanced autophagy levels improving survival and attenuating signs of disease in the mouse model (37). On the other hand, it was demonstrated that ATF4 deficient mice are more resistant to developing ALS, possibly by the reduced expression of the pro-apoptotic ER stress factors, such as CHOP and BIM (38). In turn, a deficiency of BIM delays the onset of ALS (39). In general, various studies postulated that ER stress contributes to motorneuron dysfunction in ALS, the pharmacological and genetic approaches on UPR alter the progression of the disease in ALS mouse models in vivo (7, 30, 40 and 41). Furthermore, treatment of mutant transgenic mice for SOD1 with ER stress attenuators such as guanabenz or salubrinal (42 y 43), reduces protein translation in the ER by improving the phosphorylation of eIF2α (44), delaying the disease.

All these studies present the complexity of the UPR, where the consequence of the modification of its specific components can have contrasting and different effects in the evolution of the disease (8 and 45), as can be seen in FIG. 1/9.

For this invention, the UPR was manipulated during the development using knockout mouse models with the purpose of developing responses in the protein homeostasis network in order to generate phenotypes that do not reflect the direct participation of ER stress in ALS. AAV mediated gene therapy is becoming an attractive therapeutic platform, for example for delivering active components of UPR to specific tissues. This approach avoids the pleiotropic effects of systemic and topical administration of compounds whose target is ER stress (8), thus avoiding therapeutic physiological barriers such as the blood-brain barrier. Genetic options in the delivery of these factors are the adeno-associated viruses (AAV), as they have shown safe therapeutic profiles (46).

To explore the participation of XBP1, specifically XBP1s, in the motor functions of the CNS, we tested the cellular capacity to reestablish proteostasis via activation of the UPR. In the presence of an induced spinal cord motor lesion, a motor improvement and a greater survival of oligodendrocytes has been achieved by injecting AAV in the spinal cord forcing the expression of XBP1s (47). On the other hand, a decrease of the aggregation of mutant huntignin in the striatum in vivo it was proven that by stereotaxic injection of AAV-XBP1s/GFP (Huntington's Korea) (48). Development of the Vectors (AAVs) to Actively Express XBP1s.

To analyze the function of XBP1 in vivo, constructs were generated to produce adeno-associated viruses that expressed the cassette of xbp1. The cassette of xbp1 was split from a pcDNA3-XBP-1s as the fragment MfeI/SphI and inserted in the previral plasmid pAAVsp70 that contains the AAV serotype 2 (AAV-2) with inverted ITR terminals. The vector has an expression cassette for EGFP that serves as a fluorescent marker to identify the infected cells. This vector is referred to as AAV-XBP1s/GFP as can be seen in FIG. 2.

The recombinant vector AAV-XBP1s/GFP was produced by a triple transfection of T239 cells using a rep/cap plasmid and pHelper, to subsequently be purified by a column of chromatographic affinity (50). To purify and concentrate the particles of AAV, the T239 cells (infected previously) were lysed with trypsin and nuclease followed by ion exchange chromatography using ceramic hydroxyapatite and DEAE-Sefarosa, in combination with the affinity chromatography with cellulose sulfate. As a control for this vector, the vector AAV-Mock/GFP was used, as can be seen in FIG. 2.

The viral titers were determined in real time through the TaqMan PCR test with specific splitters for the BGH poliA sequence. The methodology selected used the two constructs described in FIG. 2 and their concentrations were confirmed by direct measurement of the content of DNA (51). These concentrations are presented in Table V:

Table V

|  | Genzyme Viral Title (DRP*/ml) | Hetz lab Viral Title (VG/mL) | Hetz/Genzyme (Times) |
|---|---|---|---|
| AAV-Mock/GFP | $1.22 \times 10^{12}$ | $3.5 \times 10^{12}$ | 2.9 |
| AAV-XBP1s/GFP | $2.90 \times 10^{12}$ | $4.5 \times 10^{12}$ | 1.6 |

Two systems were tried to make the qualifications, the first through Genzyme and the second in the laboratory of the inventors (Hetz).

EGFP is co-expressed in the identification of transformed cells, a control for these cells is infecting cells that promote the overexpression of EGFP with AAV-Mock/GFP, without the target gene. This control is important to eliminate unspecific viral effects that are produced in this type of procedure. In this way, the specific biological effects can be measured reliably by applying AAV-XBP1s/GFP and its transcriptional activity.

To verify the infectivity and the levels of expression, a measurement was made of the levels of mRNA of gfp/actin and Xbp1s/actin by qPCR where different dilutions were executed between 1:2500 to 1:80000, for AAV-Mock/GFP (control), as well as for AAV-XBP1s/GFP. This confirmed the efficiency of the infection with AAV-XBP1s/GFP in HEK 293 cells. These results are presented in FIG. 3, confirming the high transduction of the construct AAV-XBP1s/GFP.

Seeing the excellent results in vitro in HFK 293 cells, an in vivo study was carried out to test the transduction efficiency after intracerebroventricular (ICV) injection of a titration equivalent to both AAVs in newborn mice. See FIG. 4. This injection leads to the diffusion of the viral particles through the cerebrospinal fluid (CSF), generating a significant global transduction of nerve cells in the central nervous system that can be detected in a pattern preserved in the hippocampus, cerebral cortex, ependymal cells, cerebellum, corticospinal tracts in the spinal cord (52 and 53). The efficiency of the transduction in the central nervous system was similar for both constructs of AAVs. The specificity of the expression was obtained using a specific serotype of the AAV virus, the AAV 2 serotype, which showed a high tropism with nerve cells (54). Using this strategy, the transduction of large regions of the brain and spinal cord (50) was verified. The studies presented in this patent confirmed the high tropism for motor nerve cells with the AAV serotype 2 virus.

Most of the transduced cells of the mice are the Purkinje cells of the cerebellum; therefore, this tissue was used to demonstrate the success of each treatment. This point was further proven by the high levels of mRNA of Xbp1 and gfp. The positive transduction in mice was of about 95% and no significant changes of perinatal death were shown in the mice after the injection with the AAVs.

The following step in the development of this invention was to see the levels in the central nervous system (SNC) of mRNA of Xbp1s and gfp in mice treated perinatally with AAV-XBP1s/GFP. To do this, the levels of mRNA of Xbp1s and gfp were quantified in the frontal cortex of the brain, spinal cord and cerebellum in 90-day old wild mice or P90, injected perinatally with AAV-XBP1s/GFP. The RNA extraction processes, synthesis of cDNA and PCR were the conventional ones to produce XBP1s and its digestion from the cDNA plus PstI, revealed only a tendency to increase the levels of mRNA of Xbp1s in the frontal cortex of mice treated with AAV-XBP1s/Gfp in comparison with the control, as can be seen in FIG. 5 top left.

On the other hand, the evaluation of the levels of mRNA of Xbp1s by qPCR is presented where the tendency was confirmed, FIG. 5 upper right. Nevertheless, when the RNA of the cerebellum (FIG. 5 bottom left) was evaluated, the increase of mRNA in Xbp1s was evident and significant (about two-fold). Surprisingly, the mRNA levels of Xbp1s, in the spinal cord (FIG. 5/9 bottom right) were more evident than in the frontal cortex (about 2.3 times). All these results confirmed the breadth of Xbp1s mRNA overexpression in mice treated with AAV-XBP1s/Gfp.

Development of the Adeno-Associated Virus (AAV)

With respect to the development of the adeno-associated virus (AAV), the AAV comprises the viral genome that consists of an expression cassette that includes a constitutive transcriptional regulatory region linked operationally to the polynucleotide of interest.

According to this invention, the adeno-associated virus (AAV) includes any known serotype of the 42 types and is derived from the parvovirus. In general, the different serotypes of AAV are genomic sequences with a significant homology at the level of amino acids and nucleic acids, which provide identical genetic functions, provide virions that are essentially identical in functional and physical terms, and their replication, assembly use practically the same mechanisms.

Particularly in this invention, the serotype 2 AAV was used (for example, like those mentioned in GenBank access number AF043303.1 (AAV 2), as presented in table III.

According to this invention, the genome of the AAV normally consist of a promoter in cis 5' and an inverted terminal repetition sequence in 3' and an expression cassette. The ITR or LTR sequences have 141 pairs of bases in length. Preferably, the complete sequence of the LTRs is used in the molecule and only slight modifications are allowed in the sequences. In a preferred form of this invention, the recombinant genome of the AAV comprises the 5' and 3' AAV LTRs. In another preferred form of this invention the 5' and 3' AAV LTRs derive from the serotype 2 AAV. In another more preferred form of this invention, the recombinant genome of the AAV lacks the open reading frame Rep and Cap.

On the other hand, the ITRs can come from other serotypes of AAV.

The AAV of this invention comprises a capsid from any serotype. For this particular invention, the capsid derived from serotypes 1, 2, 3, 4, 5, 6, 7, 8 and 9 is preferred. Although preferably the capsid of the AAV of serotype 2 is desired.

In some embodiments, a cap of the AAV for use in the method of the invention can be generated by mutagenesis (that is, insertions, deletions or substitutions) of one of the AAV caps or of its encoding nucleic acids. In some embodiments, the cap of AAV is of at least 70%, 75%, 80%, 85%, 90%, 95%, 98% or 99% or more similar to one or more of the mentioned caps of AAV.

In some embodiments, the cap of AAV is chimeric, comprising the domains of two, three, four or more of the mentioned AAV caps. In some embodiments, the cap of the AAV is a mosaic of the monomers VP1, VP2, VP3 and proceeding from two or three different AAV or a recombinant AAV (rAAV). In some embodiments, a composition of rAAV includes more than one of the mentioned CAPS.

In some embodiments, a CAP AAV for its use in a composition of rAAV is designed to contain a heterologous sequence or other modification. For example, a sequence of peptide or protein that confers selective focalization or immune evasion can be generated by genetic engineering in a Cap protein. Alternatively, or additionally, the Cap can be modified chemically so that the surface of the rAAV presents specific chemical modifications, as an example, glycol polyethylene, which can facilitate immune evasion. The Cap protein can also be generated by mutagenesis (for example, to eliminate its natural binding receptor, or to mask an immunogenic epitope).

In an embodiment, the AAV vector contains a promoter with the addition of at least one target sequence of at least one sequence of XBP1 that can be selected from the following table: Table IV (Xbp1s) (NCBI reference sequence NM_001271730.1). The reference of sequences were obtained from http://www.ncbi.nlm.nih.gov/nucleotide/411147450?report=genbank&log$=nucltop&blast_rank=1&RID=7TM54X2201R (Xbp1s)

In an embodiment, the AAV vector contains a promoter with the addition of at least one target sequence of Xbp1s that can be selected from table IV, remaining as presented in table I.

In an embodiment, the AAV vector contains a promoter with the addition of at least one target sequence that has a homology of 85% with a target sequence selected from the list mentioned previously, table IV.

In an embodiment, the AAV vector contains a promoter with the addition of at least one target sequence of Xbp1s, that can be selected from table II.

In an embodiment, the AAV vector contains a promoter with the addition of at least one target sequence that has a homology of 85% with a target sequence selected from the sequence mentioned previously, table II.

In an embodiment, the AAV vector contains a promoter with the addition of at least one target sequence that is a functional equivalent with a target sequence selected from the sequences mentioned.

The regulatory region of the transcription can include a promoter and, optionally, an enhancing region. Preferably, the promoter is selected from this list: CMV, EF-1α, PGK1, CAMKII, THY1, ChAT among others. The enhancer does not need to be specific for the neuronal tissue.

In an embodiment, the promoter is specific for Xbp1s, for example, that of cytomegalovirus, also known as CMV.

In an embodiment, the promoter is specific, for example, that of Calcium calmodulin kinase 2, also known as CAMKII.

In an embodiment, the promoter is specific, for example, also known as Thy1.

In another embodiment, the expression cassette that forms part of the AAV of the invention also includes a post-transcriptional regulation region.

The expression cassette that forms part of the AAV according to the invention includes a "polynucleotide of interest". In a preferred embodiment, the polynucleotide of interest encodes a protein that acts systemically. In another embodiment, the polynucleotide of interest encodes a protein that acts within a nerve cell. In a preferred embodiment, the protein that acts within the nerve cell is XBP1s.

The size limit of the AAV vector particles is limited to the size of the genome of the wild type AAV, which varies in size according to the serotype of AAV (that is, between 4087 to 4767). For example, native AAV2 has a genome size of 4680 pairs of bases. In some embodiments, the cloning capacity of the recombinant RNA of the vector can be limited and a desired coding sequence can imply the complete substitution of 4.8 kilobases of the genome of the virus. Therefore, large-size genes may not be adequate for use in a standard recombinant vector of AAV, in some cases. The average expert will appreciate that the options are available in the art for overcoming a limited coding capacity. For example, the AAV ITR of two genomes can hybridize to form end to end concatemers, nearly duplicating the capacity of the vector. The insertion of the splice sites permits the removal of the ITR after the transcription. Other options for overcoming a limited cloning capacity will be evident to the expert in the subject.

Ways of Administration

The ways of administrating the virus are contingent upon the virus passing the blood-brain barrier to infect the target nerve cells or that it be injected directly.

To achieve this purpose in this invention, two ways of administration have been defined.

The first of these ways is nasal (18), generally the medicines administered through the nose can enter the blood through the general circulation, can penetrate the brain directly, or in some cases, can follow both routes. Nevertheless, many of the factors that control the flow of the drug through each one of these routes are not defined completely. In general, there are three routes through which a drug administered in the nasal cavity can travel. These routes include entry directly in the systemic circulation of the nasal mucous, entry in the olfactory bulb by axonal transport through the nerve cells, and direct entry in the brain. The evidence that supports the role of each one of these routes for a variety of model substrata is summarized below for different types of viruses.

| Transport routes followed by various viral solutes through administration via the nose | | | |
|---|---|---|---|
| Solute | Model animal | Administration route | Route followed |
| Virus | | | |
| Hepatitis virus | Mouse | Nasal Inoculation | Olfatory nerve |
| Simplex herpes virus | Mouse | Nasal drops | Direct, Systemic, Olfatory Nerve |
| Encephalitis virus | Mouse | Nasal Inoculation | Olfatory nerve |
| *Pneumococcus* | Mouse | Nasal drops | Direct |

This table does not aspire to be complete in its nature, but rather it highlights some of the solutes of different classes that have demonstrated that they follow one or more routes.

The second way is direct into the central nervous system. The direct injection in fluid spaces, as intracerebroventricular (ICV); the vitreous humor in the eye; or in the cerebral fluid of the spinal cord through different routes, intraventricular or intrathecal (**) for its delivery to the choroid plexus, the ependymal/meningeal layers and from there into the adjacent brain through processes that extend within these layers; and their passage through the blood-brain barrier or blood-tumor barriers by intraarterial injection combined with an osmotic or pharmacological temporary interruption.

The ICV injection required will be defined below in the description of Materials and Methods.

Calculation of Dosage

According to Ulusoy et al (20), the titration of the vector requires a range between $10^9$ to $10^{13}$ copies of genome (CG) per ml with a tested dose between $2.9 \times 10^{12}$-$4.5 \times 10^{12}$ cg/ml. On the other hand, any dilution rate of the vectors to titrate must have a low-medium range of $10^{11}$ cg/ml, which results in the disappearance of the toxicity.

Dosage in Humans:

The dosage range in humans lies in the range between $10^9$ to $10^{30}$ viral genomes/Kg of weight, without restricting this range to the application in different age groups or with distribution volumes modified by age or pathology.

The maximum concentration or level of a substance, found experimentally or by observation, that does not cause adverse alterations detectable in the morphology, functional capacity, growth, development or duration of the life of the target organisms, distinguishable from those observed in normal organisms (control) of the same species and strain, under defined conditions of exposure.

Figure 1:
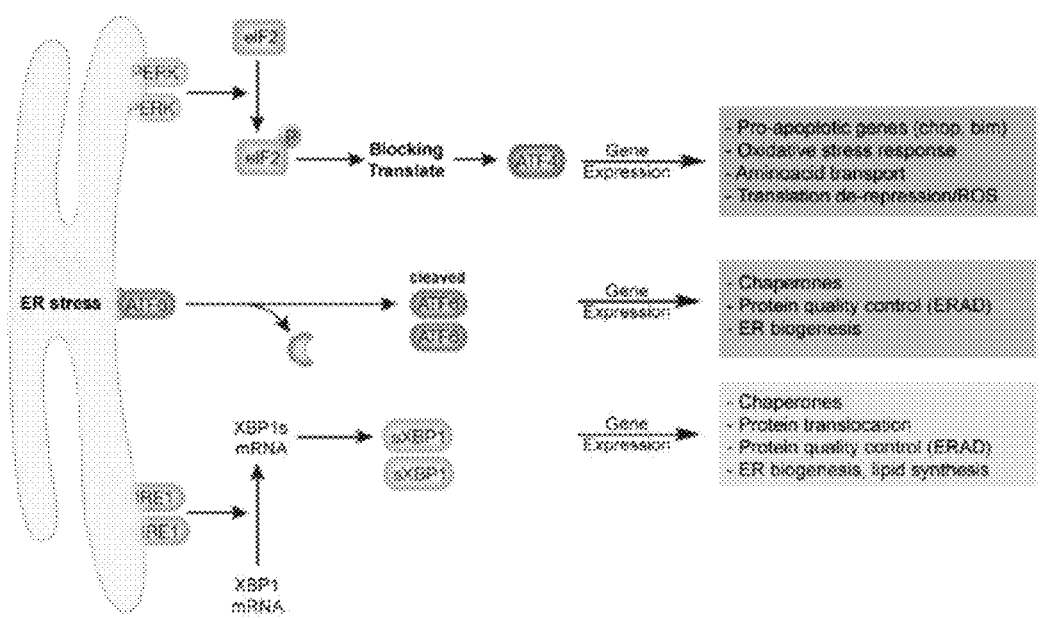
FIG. 1
Figure 2:
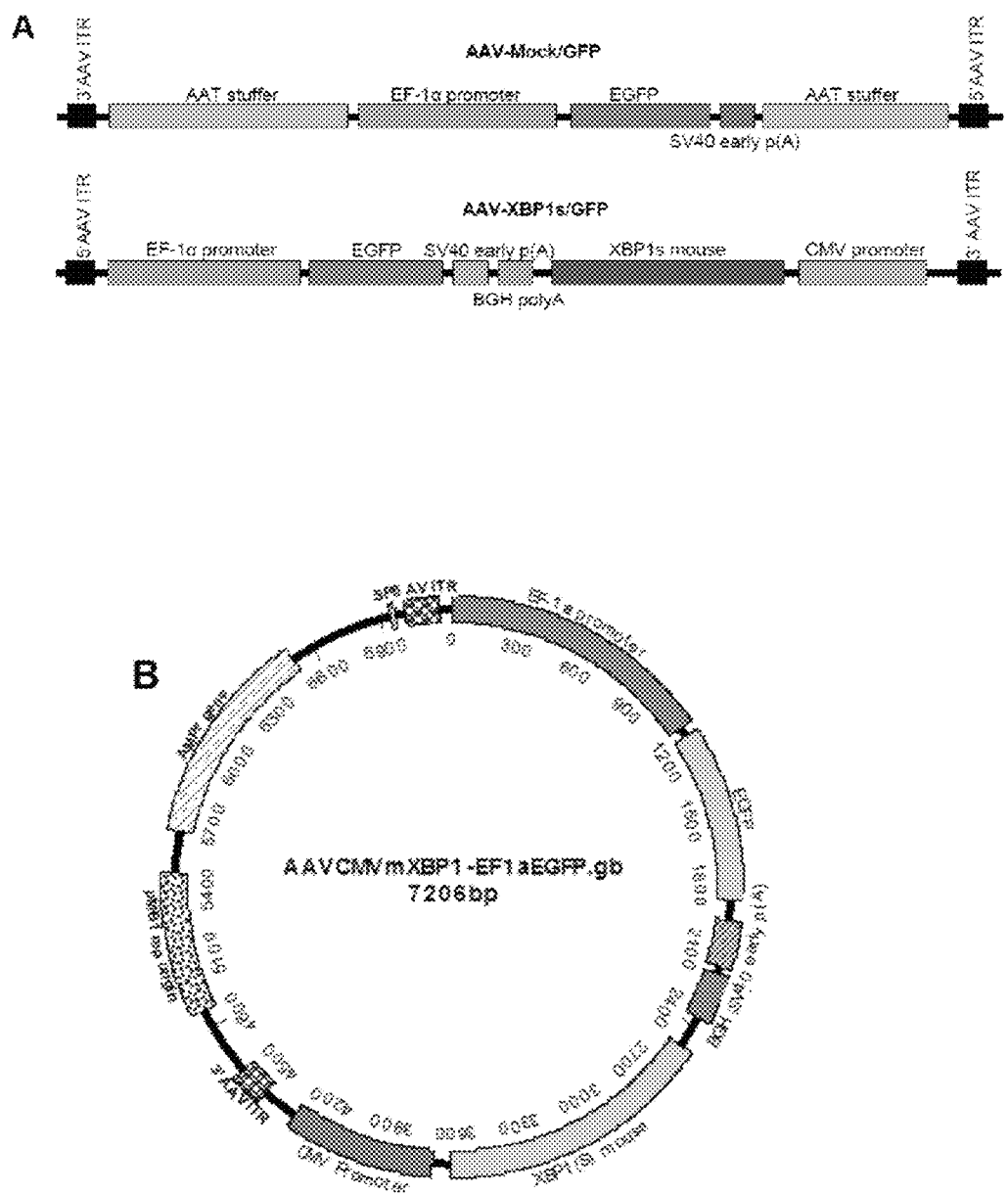
Figure 3:
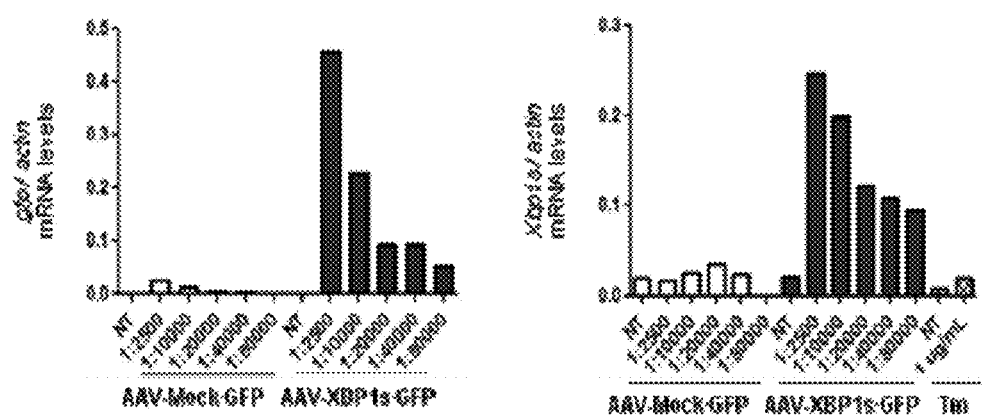
Figure 4:
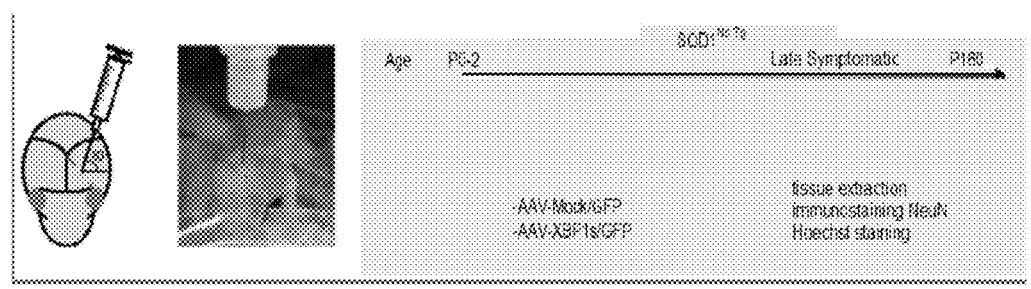
Figure 5:
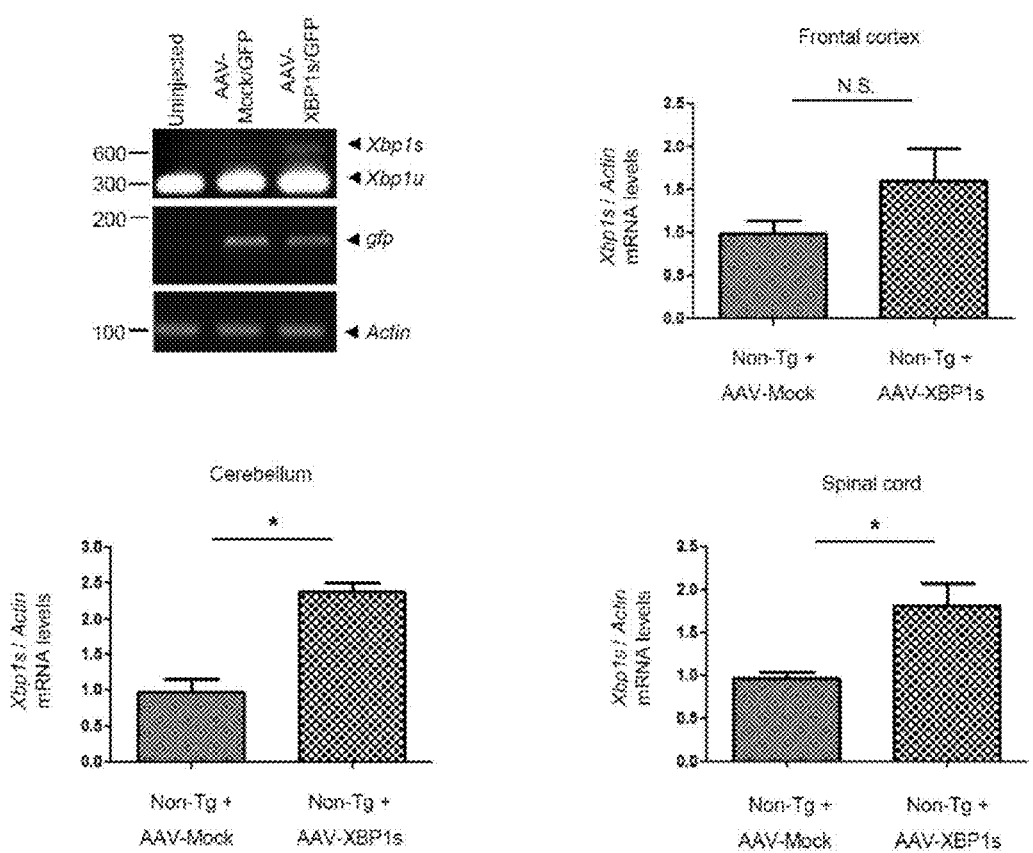

This figure is an outline of the unfolded protein response (UPR) and the genetic and pharmacological approaches in models of mice with ELA (ALS).

The figure also shows a schematic representation of the signage events of the UPR.

FIG. 2

Part A of this figure presents the diagrams of the vectors used: AAV-Mock/GFP and AAV-XBP1s/GFP.

On the other hand, part B presents the complete sequence AAV CMVmXBP1-EF1Aegfp of 7206 pairs of basis in a diagram of the plasmid.

Where the positions of the different components of the sequence are detailed below:

5'ITR: 7010-7153
Promoter EF1alfa: 1-1100
eGFP: 1139-1858
signal polyA SV40: 1937-2134
Complementary strain
signal polyA BGH: 2165-2369
mXBP1s: 2499-3614
Promoter CMV: 3686-4302
3' ITR: 4449-4585

FIG. 3

In this figure, on the left, the efficiency of the infection is presented as a measure of the levels of Xbp1s mRNA normalized to the levels of actin mRNA, as determined by qPCR, after the infection of HEK 293 cells with AAV-Mock/GFP and AAV-XBP1s/GFP. In the figure on the right, the efficiency of the infection is presented as a measure of the levels of Xbp1s mRNA normalized to the levels of actin mRNA, as determined by qPCR, after the infection of HEK 293 cells with AAV-Mock/GFP and AAV-XBP1s/GFP. HEK 293 cells are also treated with 1.0 μg of the stressor of RE Tunicamycin™ for 8 hours as control of the qPCR.

FIG. 4

In this figure, on the left-hand side, a diagram and photo are presented of the manual injection of a concentrated solution of AAVs in the cerebral ventricles of new-born mice. This diagram shows the angle at which the needle must enter for a representative and correct injection. The photo presents the place of injection. The diagram on the right presents a summary of the methodology.

FIG. 5

This figure, in its upper left-hand side, shows the relative mRNA levels of Xbp1sm Xbp1u, gfp and actin from cerebellum of mice treated with AAV-XBP1s by conventional PCR.

In the upper right-hand part of the figure, the results of the relative levels of mRNA of Xbp1s in the front cortex are presented.

In the lower left-hand part of the figure, the results of the relative levels of mRNA of Xbp1s in the cerebellum are presented.

In the lower right-hand part of the figure, the results of the relative levels of mRNA of Xbp1s in the spinal cord are presented.

These results were obtained by the treatment with AAV-XBP1s in mice through qPCR.

The levels of mRNA of Xbp1s were normalized with levels of mRNA of Actin.

N.S., not significant.

*, $p<0.05$. N=3 per group.

FIG. 6

In general, these figures represent the treatment through ICV injections of the gene therapy with AAV-XBP1s, where the survival of SOD1$^{G86R}$ is increased and where the onset of the disease is delayed.

The upper central diagram shows a Kaplan-Meyer curve where the survival obtained by both groups of SOD1$^{G86R}$ in transgenic mice treated with AAV-Mock/GFP or AAV-XBP1s/GFP is shown. Both treatments of Non-Tg mice did not present deaths at that time and were excluded from the group for a better visualization.

The Kaplan-Meyer curve in the middle left diagram was defined by the appearance of the loss of body weight calculated by the reduction of 5% of the total weight.

The Kaplan-Meyer curve in the middle right diagram, measured the duration of the symptomatic phase according to start of the body weight and the survival curve based on the data of each one of the individual animals.

The Kaplan-Meyer curve in the lower left diagram is defined by the Rotarod test performance.

The Kaplan-Meyer curve in the lower right diagram, shows the calculation of the duration of the diseased based on the determination of the appearance of the disease by loss of body weight.

Some mice did not pass the criteria of the training period and were excluded from the analysis.

Statistics: Mantel Cox test for the survival curves.

Student's T for the column test in groups.

d: day
N=7-11 per group
Bar chart: standard deviation
N.S.=not significant

FIG. 7

This upper figure shows the quantification of motor nerve cells by immunofluorescence with NeuN staining and segregation by size in nerve cells of the ventral horn of the spinal cord.

The inferior figure represents the quantification of the intensity of GFP in the ventral horn of a cross-section of the spinal cord from a final state of a mouse treated with AAV-XBP1s/GFP and the control vector.

N=3-4 per group
Bar graph: standard deviation
Student's T *=$p<0.05$
N.S., not significant
Scale of the bar: 200 microns

FIG. 8

This figure shows, in its upper left-hand part, the result of a Western Blot test of the oligomers of SOD1 from an extract of proteins from the front cortex under non-reducing conditions. An anti-actin antibody was used as protein load control.

The diagram of the upper right part shows the quantification of the aggregation of SOD1 normalized with the actin protein.

The photograph of the middle on the left presents the result of a Western Blot test of the oligomers of SOD1 from an extract of proteins from the spinal cord under non-reducing conditions. An anti-actin antibody was used as load control.

The diagram of the center on the left corresponds to the quantification of the aggregation of SOD1 normalized with the levels of the actin protein.

The lower left photograph corresponds to an experiment with the same samples of the results presented in the photograph of the center to the left with a filter trap. The Western Blot of the monomers was executed from the same samples also used as load control.

The lower right diagram presents the quantification of the oligomers of SOD1 retained by filter trap tests.

HWM: High molecular weight
Student's T *=p<0.05
N=3 per group
N.S., not significant

FIG. 9

This figure presents the mRNA levels of XBP1s for the target genes Edem and Erdj4 in the SNC in pre-symptomatic (P90) and the symptomatic late phase in the treatment with AAV-XBP1s/GFP of SOD1$^{G86R}$ mice.

The upper diagrams of the right and left present the relative levels of Edem and Erdje4 mRNA in the front cortex and spinal cord of SOD1$^{G86R}$ mice treated with symptomatic XBP1s, obtained through qPCR. The levels of mRNA were quantified and were normalized with the levels of actin.

The lower right and left diagrams present the mRNA levels of Edem and Erdj4 in the front cortex and spinal cord of SOD1$^{G86R}$ mice treated with symptomatic XBP1s, obtained through qPCR. The levels of mRNA were quantified and were normalized with the levels of actin.

Student's T *=p<0.05
N.S., not significant
N=3 per group

EXAMPLE OF APPLICATION

Experimental Test 1

Figure 6:
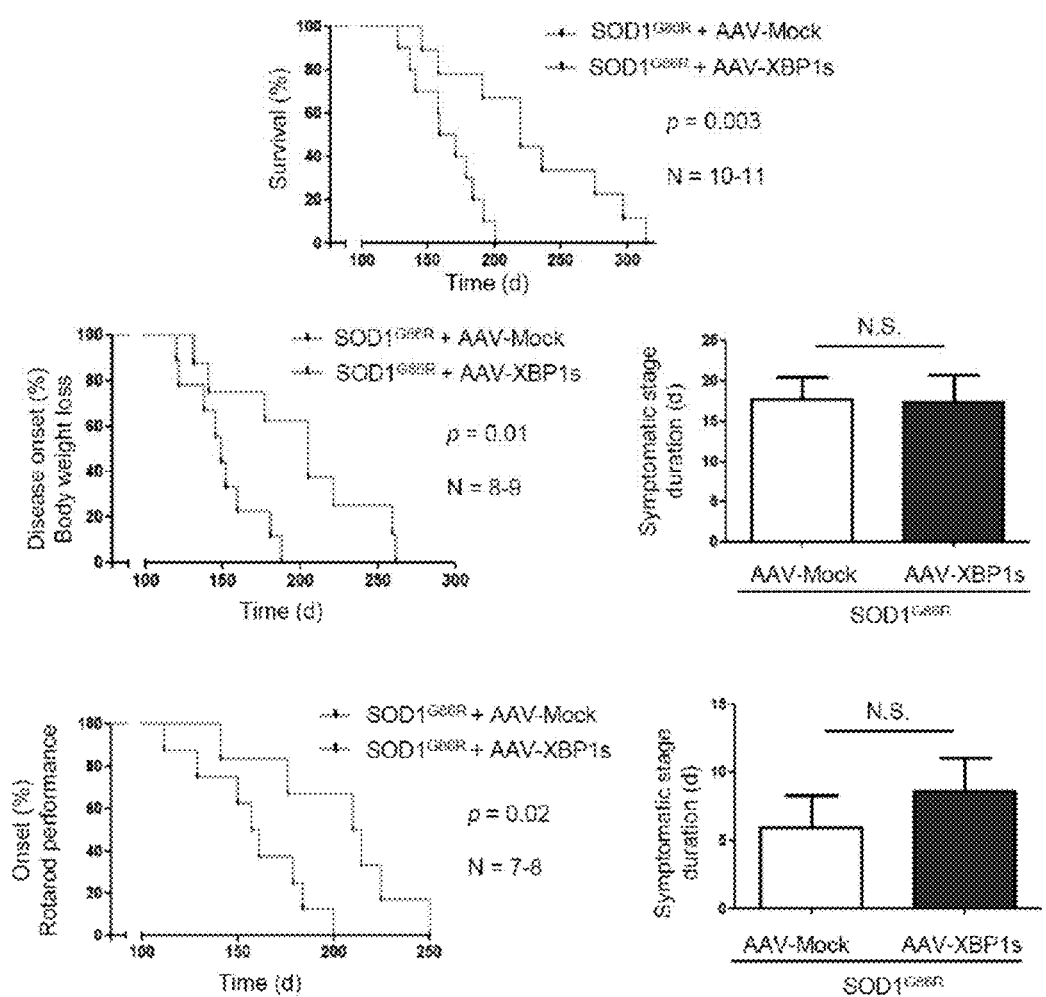

To determine the therapeutic effects of XBP1s expression in the treatment of ALS and/or the repairing of defects in the proteostasis of ER, XBP1s was delivered to the CNS of mice littermates: SOD1$^{G86R}$ mutant transgenic mice and a non-transgenic (Non-TG) mouse. The effect of the treatment with AAV-XBP1s/GFP and AAV-Mock GFP in the progression of ALS was monitored using independent litters of animals. Extraordinarily, treatment of transgenic mutants of SOD1$^{G86R}$ mice with AAV-XBP1s/GFP resulted in a substantial increase of survival. (FIG. 6, upper center).

The increase in life expectancy of mice treated with XBP1s was dramatic and increased in approximately 60 days when compared with the control group that was injected with AAV-Mock/GFP, which represents a strong protection effect in comparison with other studies of the state of the art (7, 23 and 38).

The progression of the disease was monitored by recording weight loss, decline in motor activity using the Rotarod test and by recording other signs of the disease (paralysis, tremors, curvature of the spinal cord, etc.) which together helped us know when the symptomatic state of the disease began. The beginning of the symptomatic stage of the disease was defined as a 5% loss of body weight from a maximum weight measured outside the time of the test. The middle panel of FIG. 6 shows that animals treated with AAV-XBP1s/GFP experienced a significant delay in disease onset when compared to the SOD1 mutant littermate treated with the control AAV-Mock/GFP virus.

The beginning of the disease using accelerated Rotarod tests was defined by the 50% decrease in the rate of the measurement, for the average time employed in the task before failing. This analysis confirmed a significant delay in the appearance of motor alterations in mice with ALS when compared against the mice treated with AAV-Mock/GFP, as presented in FIG. 6 below.

By using survival and the diseases offset we calculated the duration of the symptomatic phase. In these experiments, symptomatic phase was not significantly different between the groups inoculated with AAV-XBP1s/GFP and AAV-Mock/GFP (FIG. 6, middle right and lower right).

The same results were obtained when the marker of the disease was defined through visual observation. On the other hand, the injection of Non-Tg animals with the vehicle (PBS) or with the AAV control did not trigger any phenotypical novelty in all the tests.

Experimental Test 2

An analysis of protein aggregation number in motor nerve cells and the astrocytosis in SOD1$^{G86R}$ mice treated with XBP1s was made during, the symptomatic phase.

The analysis revealed that the delay in disease onset is associated with changes in the characteristics of ALS such as astrogliosis, loss of motor nerve cells and/or aggregation of proteins in mutant SOD1 mice. To be able to quantify this problem, an analysis was made of tissue from the front cortex of the brain and spinal cord of the same mice evaluated in survival curves seeing its performance through histological and biochemical analyses of the characteristics of ALS.

Figure 7:
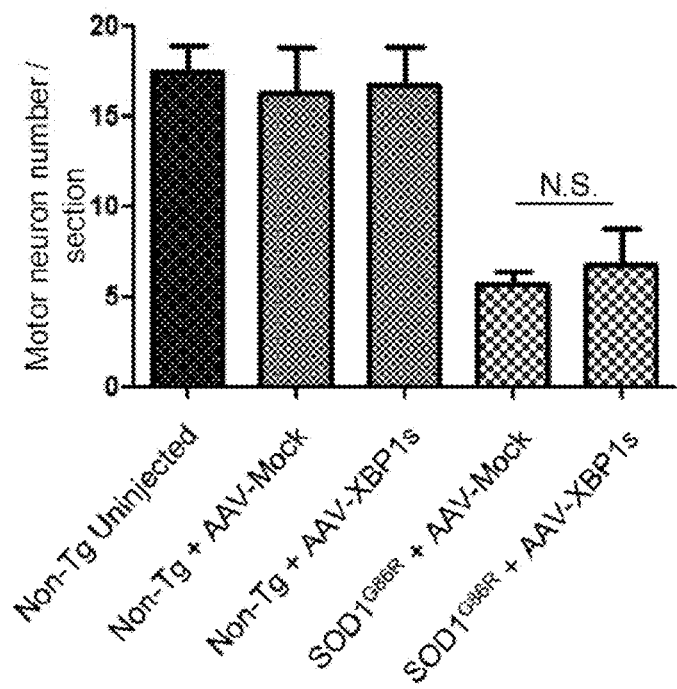
Figure 7:
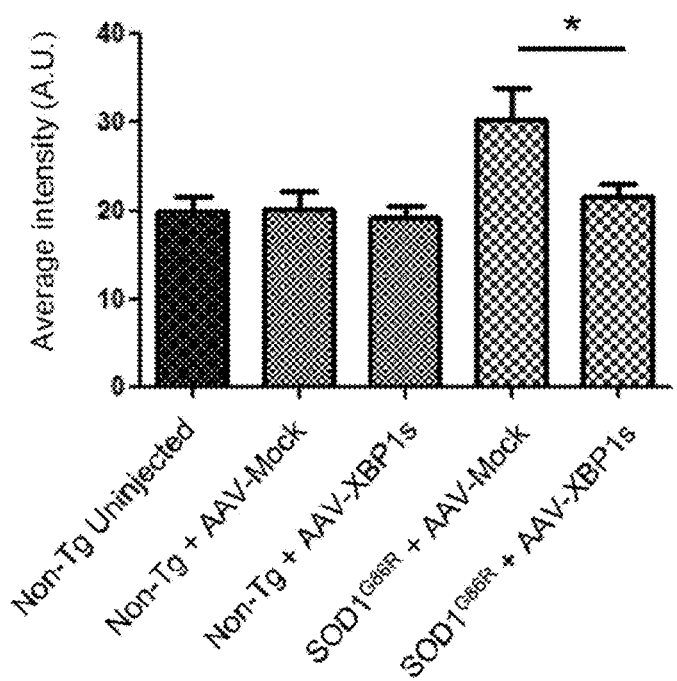

A drop in the loss of motor nerve cells was quantified via immunofluorescence (by detecting nerve cells using the antibody anti-NeuN) and via size exclusion (using an ImageJ software, to thus analyze the motoneurons specifically, which present a larger size of the soma than interneurons). The treatment of SOD1$^{G86R}$ mice with AAV-XBP1s/GFP showed a decrease in large nerve cells located in the ventral horn, which was also observed in the same mice treated with AAV-Mock/GFP. In fact, there are no significant differences between the experimental groups of SOD1$^{G86R}$ mice, as shown in the upper part of FIG. 7. Surprisingly, the overexpression of the protein XBP1s in transgenic SOD1$^{G86R}$ mice lead to a nearly complete reduction in the astrogliosis in the central horn of the symptomatic mice, as presented in the lower part of FIG. 7. These results confirm the beneficial effects of the therapy with XBP1s in the astrocytes of the spinal cord in SOD1$^{G86R}$ mice.

Figure 8:
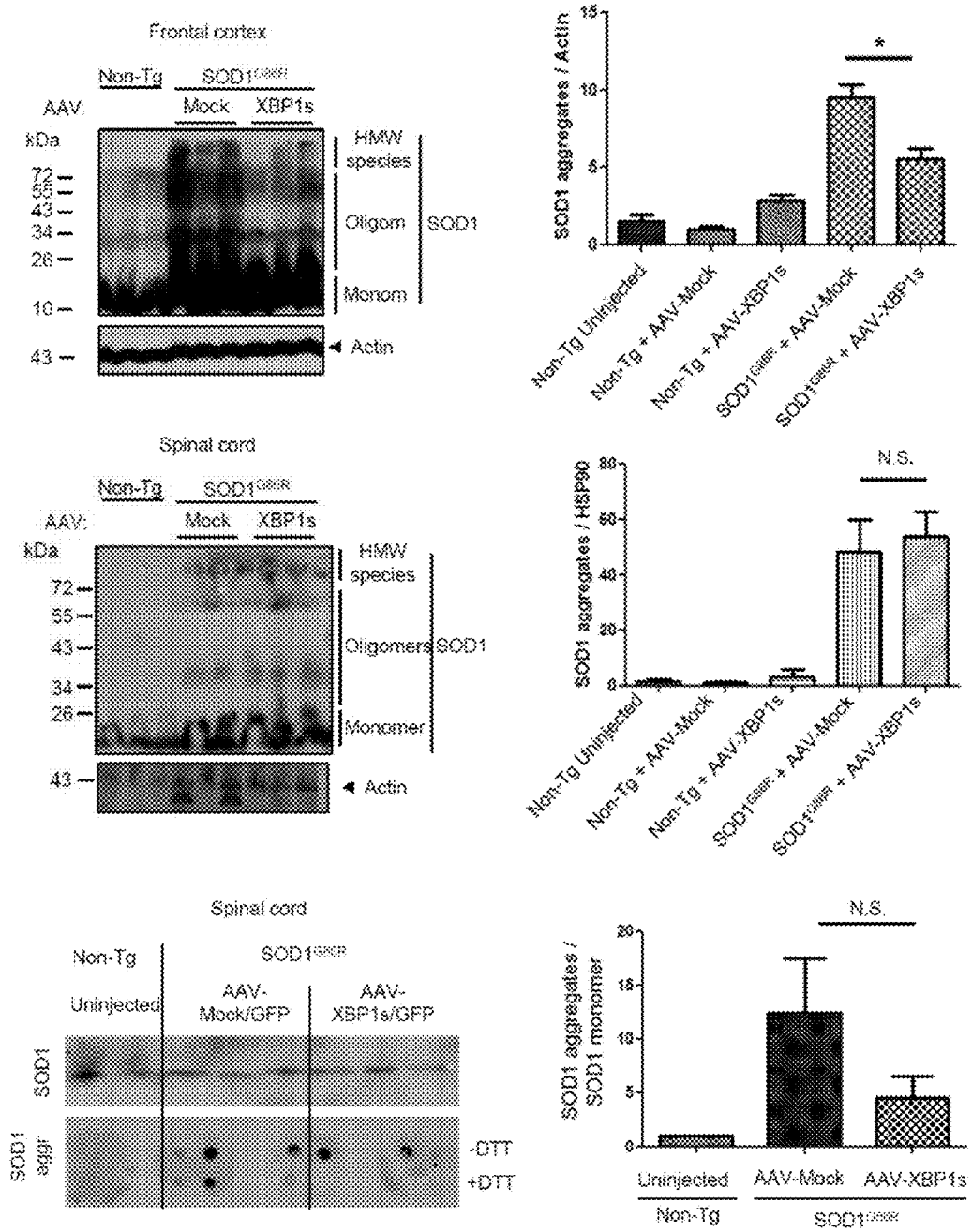

Another characteristic of the ALS mouse model used is the presence of aggregates of SOD1 in the front cortex of the brain and in the spinal cord, observed in the Western Blot analysis. The analysis of these mice revealed a significant decrease in the oligomers and aggregates in the mutants of SOD1 in the front cortex, in the animals treated with AAV-XBP1s/GFP in comparison with its controls of AAV-Mock/GFP, as can be seen on the upper left and right-hand side in FIG. 8. Surprisingly, the spinal cord protein samples from the same mouse did not show a significant reduction of the aggregates of SOD1 in the mice treated with XBP1s. This can be seen in the middle right and left hand of FIG. 8. Delving into this result, it was decided to change the approach and quantify the protein aggregates using the filter trap test. The filter trap test was executed followed by a blot for SOD1, revealing the tendency to decrease of the SOD1 species of high molecular weight in SOD1$^{G86R}$ mice treated with AAV-XBP1s/GFP. (These results can be seen in the photograph and diagram lower left and right-hand respectively).

Therefore, the increase in the expression of XBP1s in the SNC has two fundamental impacts related to ALS and associated to a longer life expectancy and an improvement in motor performance, such as:
  (i) The reduction of the aggregates of SOD1
  (ii) The reduction of the adverse astrocytic reactions.

Another study made to confirm the results obtained in the previous tests was the transcriptional analysis in the pre-symptomatic stage and in the symptomatic stage in perinatal mice injected with the AAV-XBP1s.

An early and sustained overexpression of XBP1s in the CNS and a delay in the onset of the disease suggest transcriptional changes associated to the activation downstream of the targets of UPR. A possible target of XBP1s' associated reduction in SOD1 protein aggregation is an increase in protein degradation machinery in the ER. A classic marker of this event is the protein EDEM. Analysis by qPCR of the levels of mRNA of EDEM in the total front cortex or in the spinal cord of SOD1$^{G86R}$ mice with 90 days of perinatal age treated with AAV-XBP1s/GFP revealed a significant increase only in spinal cord samples, as presented in FIG. 9 upper left and right.

Another possible effect of XBP1 is the activation of the proteins that correct poorly folded proteins, such as chaperones and companion proteins of chaperones. Erdj4 is a co-chaperone that is directly activated by XBP1. Surprisingly, a significant increase of the levels of mRNA of Erdj4 was observed in samples of front cortex and of spinal cord in SOD1$^{G86R}$ mice treated with XBP1 upon comparing the rest of the experimental groups analyzed, as can be seen in FIG. 9 upper left and right.

Figure 9:
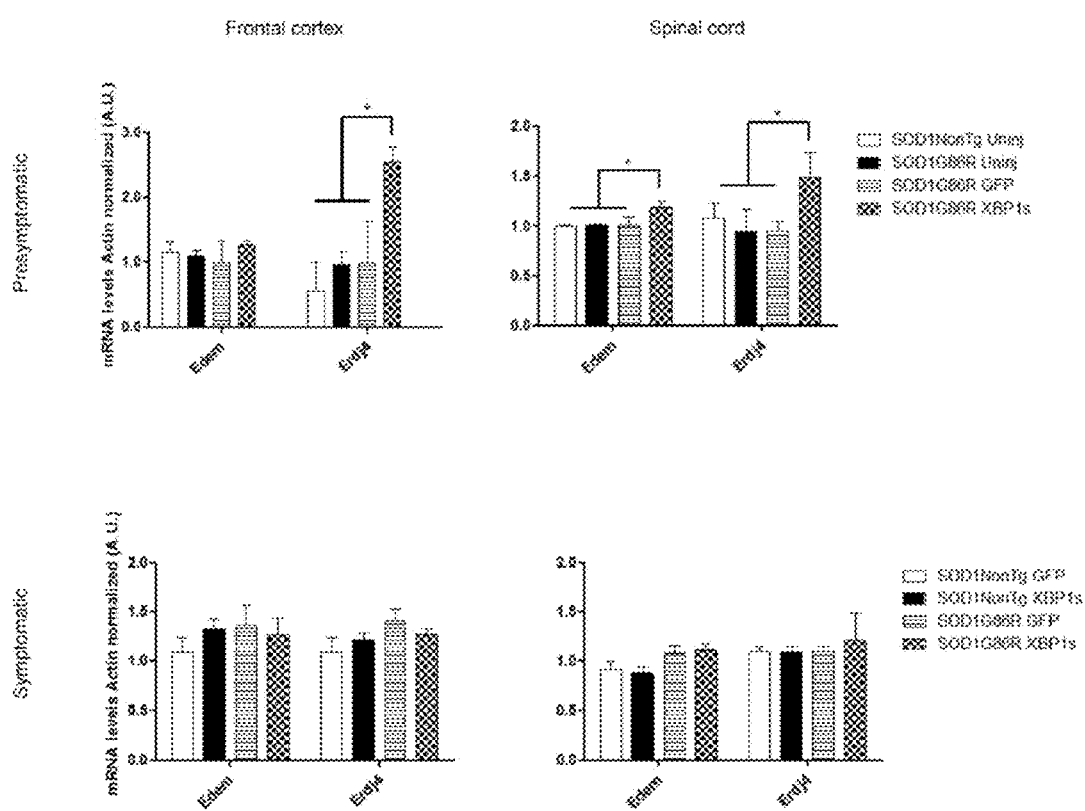

For the symptomatic phase, the treatment with XBP1s did not show significant differences between AAV-Mock/GFP or AAV-XBP1s/GFP in injected SOD1$^{G86R}$ mice, as can be seen in FIG. 9 lower left and right.

Experimentally, the treatment used consisted of the intracerebroventricular (ICV) [2] administration of 2 µL of AAV that contain the coding sequence of XBP1s of mice, whose expression is regulated under the constitutive promoter ef1 (elongation factor 1), in five different neonatal litters of SOD1$^{G86R}$×SOD1$^{WT}$ parents, that is, between the days P0 to P2.

Additionally, this vector contains the coding sequence of the protein GFP that is expressed under the constitutive promoter cmv. This corresponds to AAV-XBP1s (concentration 2.9*10e12 DRP/mL). The mice used as control will be mice ICV injected with 2 µL of AAV that contains the coding sequence of the protein GFP regulated under the control of the promoter cba to five different litters of parents SOD1$^{G86R}$×SOD1$^{WT}$. This corresponds to AAV-GFP (concentration 1.22*10e12 DRP/mL). Also monitored are SOD' and SOD1$^{G86R}$ mice, not injected. AAVs of serotype 2 were used as it was proven that this serotype possesses high tropism by motor nerve cells.

Materials and Methods
Animals and Inoculation Procedures:

To study the effect on the locomotive capacity, on the body weight and in the survival of the overexpression of XBP1s in the central nervous system using AAVs in mutant SOD1$^{G86R}$ mice, mice were used of the transgenic C57BL/6j line for SOD1, in this case they have a mutation that changes the glycine residue 86 for one of arginine (SOD1$^{G86R}$). This mutation is equivalent to the SOD$^{G85R}$ mutation found in humans.

The SOD1$^{G86R}$ mice present the classic markers of ELA or ALS, such as the presence of high molecular weight protein aggregates of the protein SOD1, as well as astrogliosis, both in a late symptomatic state.

The treatment consists in the ICV administration of 2 µL of AAVs that contains the coding sequence of XBP1s of mice, whose expression is regulated under the constitutive promoter ef1 (elongation factor 1) in five different litters of SOD$^{G86R}$×SOD1$^{WT}$ parents, between the days P0 to P2. This vector also contains the coding sequence of the protein GFP that is expressed under the constitutive promoter cmv. This corresponds to AAV-XBP1s (concentration 2.9*10e$^{12}$ DRP/mL).

The control mice also was ICV injected with 2 µL of AAV that contains the coding sequence of the protein GFP regulated under the control of the promoter cba to five different litters of SOD$^{G86R}$×SOD1$^{WT}$ parents. This corresponds to AAV-GFP (concentration 1.22*10e$^{12}$ DRP/mL). Non-injected SOD$^{G86R}$ and SOD1$^{WT}$ mice were also monitored.

AAVs of serotype 2 were used as this serotype has a high tropism by motoneurons [55].

The methodology of the ICV injection was followed according to the protocols indicated in the references.

After 21 days post ICV injection, the mice are sexed, weaned and genotyped. After establishing the experimental mice, they are observed three times a week to determine body weight, phenotype changes associated to the beginning of the symptomatic stage of ELA or ALS through visual observations and their locomotive capacity using the Rotarod.

A set visual observation criteria was used to determine the time to sacrifice the SOD$^{G86R}$ symptomatic mice. Additionally, the sacrifice of a SOD$^{WT}$ littermate was included. The onset or the age equivalent to the beginning of the symptomatic stage are determined arbitrarily according to the observation of a drastic change of a parameter measured.

In this case, the onset of body weight is established as the 5% decrease in the weight of the mouse regarding its maximum weight, always in a context of weight loss, that is, to establish the onset, at least three prior measurements of decreasing weight must have been registered.

The onset of Rotarod has been determined as a 50% decrease of the maximum Rotarod time, also in the same decreasing context.

The guidelines established by the care and use of animals committee of the University of Chile (Chile) were used for all the experiments in animals presented in this development.

For the analysis of the aggregation levels of the mutated SOD1 protein, the number of motoneurons and the astrogliosis in the spinal cord of SOD$^{G86R}$ mice injected with AAV-XBP1s in a late symptomatic state, standard biochemical analysis of the researcher's laboratory were used.

The aggregation level of the SOD1 protein, and the expression of the transgenes GFP and XBP1s by were detected by Western blot; the presence of the RNA that encodes XBP1s was also studied as previously described [56].

Behavioral Tests:

All the experiments were executed blindly, and different cohorts of animals were used for each test.

Rotarod

The mice were placed in a bar that rotates at 4 rpm during a minute of acclimatization. The rod was accelerated to 0.1 rpm/s up to 40.0 rpm. The test continued for two minutes. The latency in falling was measured and the rpm at the moment each mouse fell. Three tests were executed with each mouse and averaged.

Criteria of Visual Observations

This criteria for determining the beginning of the disease through visual observations [56] takes place when the evidently arched back, personal slovenliness and paralysis of the hind limbs of the mouse are observed.

Production of Adeno-Associated Virus

The particles of the serotype 2 AAV vector (AAV2) were produced by the transfection of HEK293 cells (Agilent Technologies, Santa Clara, Calif.) and were purified in a gradient of iodixanol followed by affinity column chromatography. The resulting AAV particles, as well as their infectivity in HEK293T cells was determined through TaqMan qPCR tests.

Preparation of the Transgene AAV Plasmid (pAAV) for XBP1s.

The expression cassette of the murine gene of Xbp1s was isolated from the pcDNA3-XBP-1s plasmid as a MfeI/SphI fragment and inserted in the pAAVsp70 pre-viral plasmid that contains the inverted terminal repeats (ITRs). The vector contains the GFP expression cassette that serves as a marker of transduced cells, although others such as Egfp, Flag, Gfp, His and Myc, among others, could be used. In the case of the GFP protein, it was discovered in a species of medusa called *Aequorea Victoria*. To improve the stability of the protein at the temperature of the mammals (37° C.), a mutation was made to the sequence that encodes the GFP protein (F64L), giving it greater stability at body temperature. This new protein is called EGFP (enhanced GFP) and it is a protein used in this development. The recombinant virus AAV2-XBP1s was produced by triple transfection of HEK-293T cells using the rep/cap plasmids and the pHelper (Stratagene, La Jolla, Calif., USA) and purified by affinity column chromatography, as described previously [1]. To obtain pure and concentrated viral particles, the viral lysates of HEK-293T cells were treated with trypsin and nuclease followed by ionic exchange chromatography using ceramic hydroxyapatite and DEAE-Sepharose in combination with chromatography of cellufine sulfate. The viral titles were determined through OCR in real time through TaqMan probe, with splitters that are specific for the poliA sequence of BGH.

Intracerebroventricular Injections

The intracerebroventricular injection is a method widely used to obtain high viral transduction in all the central nervous system (Castillo, K., et al, Measurement of autophagy flux in the nervous system in vivo. Cell death and disease, 2013. 4: p. e917, Glascock, J. J., et al., Delivery of therapeutic agents through intracerebroventricular (ICV) and intravenous (IV) injection in mice. Journal of visualized experiments: JoVE, 2011(56)) and recently commented by our laboratory (Matus, S., V. Valenzuela and C. Hetz, A new method to measure autophagy flux in the nervous system. Autophagy, 2014. 10(4); p. 710-4).

Protocol of the Intracerebroventricular Injection

Materials:

AAV aliquot in the ice
1 ml of PBS in ice
1% FastGreen (staining)
Insulin syringe
Adhesive tape
P200 and micropipette P20, advice
Corkboard covered with aluminum paper, with a bit of pillow made of aluminum paper for the head of the baby animal
Bag of ice
Parafilm
Cold light
Fine point marker This protocol must be executed in a special virus installation.

Preparation AAV:
1. Dilute 2 µL of FastGreen in 28 µL of PBS.
2. Add 2.5 µL of the FastGreen dilution to 10 µL of AAV.
3. Load injection is of 2.5 µL per baby animal.
4. The amount of virus used in each injection corresponds to 2 µL of the viral title of the AAV with the lowest concentration (AAV-GFP), that is, $2.44*10^9$ viral particles. Therefore, beforehand, the AAV-XBP1s must be diluted 2.3 times to thus have a viral title equivalent to the AAV-GFP control.

Preparation of the Injection Counter:
1. Prepare the cold light and the corkboard in front of your place. Put the ice on the corkboard to keep it cold.
2. Place a piece of paraffin stuck on the workplace, next to the corkboard, draw a circle on the parafilm. This circle is going to be the place to put the AAV preparation drop. Place the AAV preparation drop (2.5 µL) on the circle drawn and then load it carefully in the insulin syringe to avoid bubbles.
3. Remove the baby animal from the mother. This step is crucial. To remove the baby animal from its mother, which is very important to avoid the mother's stress (the mother realizes that there is a baby, this is a stressful situation for them).
   First, the researcher's gloves are impregnated with the smell of the bed before and after picking up the baby animal. To pick up the baby animal, knock against the cage on the place opposite the nest to oblige the mother to abandon the nest. When this is achieved, only one baby animal is removed at a time. Then place the baby on the ice to anesthetize. Wait until it no longer moves (between 2 and 4 minutes).
4. When the mouse is completely anesthetized, place the baby on the corkboard (dorsal side up) and hold it softly with two strips of masking tape, one over the back and the other over its nose.
5. Draw a point on the bregma and then a point in the average distance between the bregma and an eyeball (I use the left side, for right-handed people), this is the injection point.
6. Place the loaded syringe at the injection point, bear in mind that the bevel must be pointing to the middle line, then rotate the position of the syringe approximately 10 degrees to the right (outside) and 10 degrees to you (see figure). Then insert the syringe between 3 and 4 mm in the direction of the axis of the syringe and inject the content smoothly, then remove the syringe carefully. You must see the diffusion of the colorant through both lateral ventricles, sometimes it can be seen as it passes through the back part of the brain. The injection has failed when the staining is observed with subcutaneous distribution.

7. Place the baby animal in a hot bowl until it starts to open its mouth (this is after the first movement of the limbs), which takes about 20 seconds. Then place the baby back in the cage, specifically in the place opposite the mother's nest, half buried, then "call" its mother knocking on the cage, the mother starts looking for it. It is a good sign when the mother takes the baby and places it in the nest.

8. All the waste that had contact with the virus must be eliminated in a special container.

Preparation of Tissues for the Biochemical Analysis.

The mice were sacrificed by narcosis of $CO_2$, the brains were removed, then the cortex and the spinal cord, from both hemispheres were dissected quickly in a plastic plate cooled with ice. The tissue is then homogenized (spinal cord or brain cortex) in a phosphate buffer PBS, then the homogenized is divided into two fractions:
1) Homogenizing of proteins; and
2) Homogenized in Trizol for extraction of RNA.

The protein homogenate is divided again to leave one half in the RIPA buffer, buffer used to observe proteins in general; and the other half in a 1% solution of Triton in PBS, smoother detergent to preserve the protein aggregates. The amount of protein of each sample is quantified by the BCA protocol and the gels are loaded with the following samples:
1) Samples in Triton X-100 1% without DTT in a gel of polyacrylamide at 15%. This gel is used to observe protein aggregates, in this case, aggregates of the SOD1 protein.
2) Samples in RIPA buffer with DTT in two gels of polyacrylamide at 8% to observe the GFP reporter proteins and XBP1s separately.

Extraction of RNA and OCR in Real Time

The total RNA was isolated from the spinal cord and total brain cortex. The homogenized left in Trizol is used to extract RNA. A synthesis of cDNA will be executed as of RNA. Then the PCR test will be executed to amplify a fragment corresponding to the cDNA of Xbp1s. Then this product of PCR will be incubated with the PstI restriction enzyme, which digests exclusively the fragment that corresponds to the unprocessed form of Xbp1; therefore, this test permits resolving, in an adequate manner, the forms processed (Xbp1s) and unprocessed (Xbp1u) of Xbp1 in an agarose gel at 2.5% under electrophoretic run [6]. Specifically, the cDNA was synthesized with a kit of high capacity reverse transcription cDNA (Applied Biosystems). SYBR green and a Mx3005P QPCR System (Stratagene) were used for the quantitative RT-PCR. The relative amount of mRNA was calculated by the comparative threshold cycle method with β-actin as control.

Western Blot of Tissue

The extraction of proteins from the tissue of mice was carried out in RIPA buffer (20 mM Tris pH 8.0, NaCl 150 mM, 0.1% of SDS, 0.5% deoxycholate, 0.5% of Triton X-100) that contains a mixture of protease inhibitors and a mixture of phosphatase inhibitors (Sigma, U.S.A.). An example of this quantification was made with the BCA test kit (Pierce, U.S.A.). Total cellular extracts were separated by SDS-PAGE and were transferred to membranes of polyvinylidene difluoride. The following antibodies were used for the analysis of immunoblot: Hsp90 (1:3000, Calbiochem 574597).

Preparation of the Tissue and the Histological Analysis.

The mice were sacrificed by narcosis of $CO_2$ and they were perfused with paraformaldehyde at 4%. The brains were extracted, then fixed during the night at 4° C. in the same solution and subsequently placed at 30% of sucrose (Merck, U.S.A.) at 4° C. for 48 hours. The brains were frozen in an optimum compound for their cutting at an adequate temperature (Tissue Tek, U.S.A.), transversal sections of 25 μm of spinal cord were cut in a cryostat (Leica, Germany) and then mounted on slides and incubations made with the respective antibodies to identify nerve cells or astrocytes. The viral transduction levels will be determined in various tissues of the central nervous system (brain, spinal cord and sciatic nerve) through observation of the fluorescence of the GFP reporter protein in a fluorescence microscope. To determine the cellular changes associated to the treatment, immunofluorescence will be carried out using antibodies to identify different cellular types such as nerve cells (anti-NeuN, MAB377, Millipore Bioscience Research Reagents, Billerica, Mass., USA), astrocytes (N1506, Dako, Glostrup, Denmark) and microglia (MCA74G, Serotec, Morphosys, Oxford, UK).

Protocol of Immunofluorescence of Cuts of Spinal Cord Mounted on Slides

Materials

Incubation boxes (humid chamber)

Incubation coupling

Antibodies

Blocking buffer

Fluoromount

Preparation of Blocking Buffer:
Bovine serum albumin (BSA) at 5% in triton at 0.05%.

Procedure

The slides are washed three times with PBS for ten minutes each.

They are blocked with blocking buffer for an hour in a humid chamber.

The primary Antibody diluted in blocking buffer is placed for 2-3 hours or o.n. in the humid chamber.

Three ten-minute washings with PBS are executed.

The secondary antibody diluted in blocking buffer is placed for two hours in the humid chamber.

Three ten-minute washings with PBS are executed.

The cuts are mounted with fluoromount and the slides are sealed with enamel.

The slides are kept in the dry incubation box at 4° C.

The levels of viral transduction were determined in different tissues of the central nervous system (brain, spinal cord and sciatic nerve) through observation of the fluorescence of the GFP reporter protein in a fluorescence microscope. To determine the cellular changes associated to the treatment, immunofluorescence will be executed using antibodies to identify different cellular types such as nerve cells (anti-NeuN, MAB377, Millipore Bioscience Research Reagents, Billerica, Mass., USA), astrocytes (N1506, Dako, Glostrup, Denmark) and microglia (MCA74G, Serotec, Morphosys, Oxford, UK).

Statistics

The data are expressed as medium and SEM. Depending on the experiments, the results were compared statistically using the Student T test or the Mann-Whitney test, of two-way ANOVA followed by Holm-Sidack or Bonferroni as post-hoc test or Kruskal-Wallis one-way ANOVA in ranges followed by the Dunn Method or Bonferroni as post-hoc test.

REFERENCES

1. Pasinelli, P. and R. H. Brown, Molecular biology of amyotrophic lateral sclerosis: insights from genetics. Nature reviews. Neuroscience, 2006. 7(9): p. 710-23.
2. Leblond, C. S., et al., Dissection of genetic factors associated with amyotrophic lateral sclerosis. Experimental neurology, 2014.
3. Ferraiuolo, L., et al., Molecular pathways of motor neuron injury in amyotrophic lateral sclerosis. Nature reviews. Neurology, 2011. 7(11): p. 616-30.
4. Saxena, S. and P. Caroni, Selective neuronal vulnerability in neurodegenerative diseases: from stressor thresholds to degeneration. Neuron, 2011. 71(1): p. 35-48.
5. Walter, P. and D. Ron, The unfolded protein response: from stress pathway to homeostatic regulation. Science, 2011. 334(6059): p. 1081-6.
6. Hetz, C. and B. Mollereau, Disturbance of endoplasmic reticulum proteostasis in neurodegenerative diseases. Nature reviews. Neuroscience, 2014. 15(4): p. 233-49.
7. Saxena, S., E. Cabuy, and P. Caroni, A role for motoneuron subtype-selective ER stress in disease manifestations of FALS mice. Nature neuroscience, 2009. 12(5): p. 627-36.
8. Hetz, C., E. Chevet, and H. P. Harding, Targeting the unfolded protein response in disease. Nature reviews. Drug discovery, 2013. 12(9): p. 703-19.
9. Matus, S., et al., ER Dysfunction and Protein Folding Stress in ALS. International journal of cell biology, 2013. 2013: p. 674751.
10. Walker, A. K. and J. D. Atkin, Stress signaling from the endoplasmic reticulum: A central player in the pathogenesis of amyotrophic lateral sclerosis. IUBMB life, 2011. 63(9): p. 754-63.
11. Hetz, C., The unfolded protein response: controlling cell fate decisions under ER stress and beyond. Nat Rev Mol Cell Biol, 2012. 13(2): p. 89-102.
12. Acosta-Alvear, D., et al., XBP1 controls diverse cell type- and condition-specific transcriptional regulatory networks. Mol Cell, 2007. 27(1): p. 53-66.
13. Lee, A. H., N. N. Iwakoshi, and L. H. Glimcher, XBP-1 regulates a subset of endoplasmic reticulum resident chaperone genes in the unfolded protein response. Mol Cell Biol, 2003. 23(21): p. 7448-59.
14. Harding, H. P., et al., An integrated stress response regulates amino acid metabolism and resistance to oxidative stress. Mol Cell, 2003. 11(3): p. 619-33.
15. Woehlbier, U. and C. Hetz, Modulating stress responses by the UPRosome: a matter of life and death. Trends Biochem Sci, 2011. 36(6): p. 329-37.
16. Tabas, I. and D. Ron, Integrating the mechanisms of apoptosis induced by endoplasmic reticulum stress. Nature cell biology, 2011. 13(3): p. 184-90.
17. Hetz, C., The unfolded protein response: controlling cell fate decisions under ER stress and beyond. Nature reviews. Molecular cell biology, 2012. 13(2): p. 89-102.
18. Atkin, J. D., et al., Endoplasmic reticulum stress and induction of the unfolded protein response in human sporadic amyotrophic lateral sclerosis. Neurobiol Dis, 2008. 30(3): p. 400-7.
19. Ilieva, E. V., et al., Oxidative and endoplasmic reticulum stress interplay in sporadic amyotrophic lateral sclerosis. Brain, 2007. 130(Pt 12): p. 3111-23.
20. Ito, Y., et al., Involvement of CHOP, an ER-stress apoptotic mediator, in both human sporadic ALS and ALS model mice. Neurobiol Dis, 2009. 36(3): p. 470-6.
21. Sasaki, S., Endoplasmic reticulum stress in motor neurons of the spinal cord in sporadic amyotrophic lateral sclerosis. J Neuropathol Exp Neurol, 2010. 69(4): p. 346-55.
22. Walker, A. K., et al., Protein disulphide isomerase protects against protein aggregation and is S-nitrosylated in amyotrophic lateral sclerosis. Brain, 2010. 133(Pt 1): p. 105-16.
23. Hetz, C., et al., XBP-1 deficiency in the nervous system protects against amyotrophic lateral sclerosis by increasing autophagy. Genes Dev, 2009. 23(19): p. 2294-306.
24. Kieran, D., et al., Deletion of the BH3-only protein puma protects motoneurons from ER stress-induced apoptosis and delays motoneuron loss in ALS mice. Proc Natl Acad Sci USA, 2007. 104(51): p. 20606-11.
25. Kikuchi, H., et al., Spinal cord endoplasmic reticulum stress associated with a microsomal accumulation of mutant superoxide dismutase-1 in an ALS model. Proc Natl Acad Sci USA, 2006. 103(15): p. 6025-30.
26. Mori, A., et al., Derlin-1 overexpression ameliorates mutant SOD1-induced endoplasmic reticulum stress by reducing mutant SOD1 accumulation. Neurochem Int, 2010. 58(3): p. 344-53.
27. Nagata, T., et al., Increased ER stress during motor neuron degeneration in a transgenic mouse model of amyotrophic lateral sclerosis. Neurol Res, 2007. 29(8): p. 767-71.
28. Urushitani, M., et al., Chromogranin-mediated secretion of mutant superoxide dismutase proteins linked to amyotrophic lateral sclerosis. Nature neuroscience, 2006. 9(1): p. 108-18.
29. Vlug, A. S., et al., ATF3 expression precedes death of spinal motoneurons in amyotrophic lateral sclerosis-SOD1 transgenic mice and correlates with c-Jun phosphorylation, CHOP expression, somato-dendritic ubiquitination and Golgi fragmentation. Eur J Neurosci, 2005. 22(8): p. 1881-94.
30. Wang, L., B. Popko, and R. P. Roos, The unfolded protein response in familial amyotrophic lateral sclerosis. Hum Mol Genet, 2011. 20(5): p. 1008-15.
31. Wootz, H., et al., XIAP decreases caspase-12 cleavage and calpain activity in spinal cord of ALS transgenic mice. Exp Cell Res, 2006. 312(10): p. 1890-8.
32. Wootz, H., et al., Caspase-12 cleavage and increased oxidative stress during motoneuron degeneration in transgenic mouse model of ALS. Biochem Biophys Res Commun, 2004. 322(1): p. 281-6.
33. Zhang, Y. J., et al., Aggregation-prone c9FTD/ALS poly(GA) RAN-translated proteins cause neurotoxicity by inducing ER stress. Acta neuropatologica, 2014. 128(4): p. 505-24.
34. Alami, N. H., et al., Axonal transport of TDP-43 mRNA granules is impaired by ALS-causing mutations. Neuron, 2014. 81(3): p. 536-43.
35. Matus, S., D. B. Medinas, and C. Hetz, Common ground: stem cell approaches find shared pathways underlying ALS. Cell stem cell, 2014. 14(6): p. 697-9.
36. Hetz, C., et al., Unfolded protein response transcription factor XBP-1 does not influence prion replication or pathogenesis. Proc Natl Acad Sci USA, 2008. 105(2): p. 757-62.
37. Castillo, K., et al., Trehalose delays the progression of amyotrophic lateral sclerosis by enhancing autophagy in motoneurons. Autophagy, 2013. 9(9): p. 1308-20.
38. Matus, S., et al., Functional contribution of the transcription factor ATF4 to the pathogenesis of amyotrophic lateral sclerosis. PLoS One, 2013. 8(7): p. e66672.

39. Hetz, C., et al., The proapoptotic BCL-2 family member BIM mediates motoneuron loss in a model of amyotrophic lateral sclerosis. Cell death and differentiation, 2007. 14(7): p. 1386-9.
40. Shimazawa, M., et al., An Inducer of VGF Protects Cells against ER Stress-Induced Cell Death and Prolongs Survival in the Mutant SOD1 Animal Models of Familial ALS. PLoS One, 2010. 5(12): p. e15307.
41. Bernard-Marissal, N., et al., Calreticulin levels determine onset of early muscle denervation by fast motoneurons of ALS model mice. Neurobiology of disease, 2014.
42. Wang, L., et al., Guanabenz, which enhances the unfolded protein response, ameliorates mutant SOD1-induced amyotrophic lateral sclerosis. Neurobiology of disease, 2014. 71: p. 317-24.
43. Jiang, H. Q., et al., Guanabenz delays the onset of disease symptoms, extends lifespan, improves motor performance and attenuates motor neuron loss in the SOD1 G93A mouse model of amyotrophic lateral sclerosis. Neuroscience, 2014. 277: p. 132-8.
44. Boyce, M., et al., A selective inhibitor of eIF2alpha dephosphorylation protects cells from ER stress. Science, 2005. 307(5711): p. 935-9.
45. Kraskiewicz, H. and U. FitzGerald, InterfERing with endoplasmic reticulum stress. Trends in pharmacological sciences, 2012. 33(2): p. 53-63.
46. Witt, J. and W. J. Marks, Jr., An update on gene therapy in Parkinson's disease. Current neurology and neuroscience reports, 2011. 11(4): p. 362-70.
47. Valenzuela, V., et al., Activation of the unfolded protein response enhances motor recovery after spinal cord injury. Cell Death Dis, 2012. 3: p. e272.
48. Zuleta, A., et al., AAV-mediated delivery of the transcription factor XBP1s locally into the striatum reduces mutant Huntingtin aggregation in a mouse model of Huntington's disease. Biochem Biophys Res Commun, 2012. 420(3): p. 558-563.
49. Valdes, P., et al., Control of dopaminergic neuron survival by the unfolded protein response transcription factor XBP1. Proceedings of the National Academy of Sciences of the United States of America, 2014. 111(18): p. 6804-9.
50. Castillo, K., et al., Measurement of autophagy flux in the nervous system in vivo. Cell death & disease, 2013. 4: p. e917.
51. Sommer, J. M., et al., Quantification of adeno-associated virus particles and empty capsids by optical density measurement. Molecular therapy: the journal of the American Society of Gene Therapy, 2003. 7(1): p. 122-8.
52. Passini, M. A. and J. H. Wolfe, Widespread gene delivery and structure-specific patterns of expression in the brain after intraventricular injections of neonatal mice with an adeno-associated virus vector. J Virol, 2001. 75(24): p. 12382-92.
53. Glascock, J. J., et al., Delivery of therapeutic agents through intracerebroventricular (ICV) and intravenous (IV) injection in mice. J Vis Exp, 2011(56).
54. Bartlett, J. S., R. J. Samulski, and T. J. McCown, Selective and rapid uptake of adeno-associated virus type 2 in brain. Human gene therapy, 1998. 9(8): p. 1181-6.
55. Zincarelli, C., et al., Analysis of AAV serotypes 1-9 mediated gene expression and tropism in mice after systemic injection. Molecular therapy: the journal of the American Society of Gene Therapy, 2008. 16(6): p. 1073-80.
56. Calfon, M., et al., IRE1 couples endoplasmic reticulum load to secretory capacity by processing the XBP-1 mRNA. Nature, 2002. 415(6867): p. 92-6.

TABLE I

| (SEQ ID NO: 1) | |
|---|---|
| AAVCMVmXBP1-EF1aGFP | |
| 7010-7153 | 5'ITR |
| 1-1100 | Promoter EF1alfa |
| 1139-1858 | eGFP |
| 1937-2134 | signal polyA SV40 |
| Complementary thread | |
| 2165-2369 | signal polyA BGH |
| 2499-3614 | mXBP1s |
| 3686-4302 | Promoter CMV |
| 4449-4585 | 3' ITR |

```
ORIGIN
    1   CCGGTGCCTA GAGAAGGTGG CGCGGGGTAA ACTGGGAAAG TGATGTCGTG TACTGGCTCC
   61   GCCTTTTTCC CGAGGGTGGG GGAGAACCGT ATATAAGTGC AGTAGTCGCC GTGAACGTTC
  121   TTTTTCGCAA CGGGTTTGCC GCCAGAACAC AGGTAAGTGC CGTGTGTGGT TCCCGCGGGC
  181   CTGGCCTCTT TACGGGTTAT GGCCCTTGCG TGCCTTGAAT TACTTCCACC TGGCTGCAGT
  241   ACGTGATTCT TGATCCCGAG CTTCGGGTTG GAAGTGGGTG GGAGAGTTCG AGGCCTTGCG
  301   CTTAAGGAGC CCCTTCGCCT CGTGCTTGAG TTGAGGCCTG GCCTGGGCGC TGGGGCCGCC
  361   GCGTGCGAAT CTGGTGGCAC CTTCGCGCCT GTCTCGCTGC TTTCGATAAG TCTCTAGCCA
```

TABLE I-continued (SEQ ID NO: 1)

| | |
|---|---|
| 421 | TTTAAAATTT TTGATGACCT GCTGCGACGC TTTTTTTCTG GCAAGATAGT CTTGTAAATG |
| 481 | CGGGCCAAGA TCTGCACACT GGTATTTCGG TTTTTGGGGC CGCGGGCGGC GACGGGGCCC |
| 541 | GTGCGTCCCA GCGCACATGT TCGGCGAGGC GGGGCCTGCG AGCGCGGCCA CCGAGAATCG |
| 601 | GACGGGGGTA GTCTCAAGCT GGCCGGCCTG CTCTGGTGCC TGGCCTCGCG CCGCCGTGTA |
| 661 | TCGCCCCGCC CTGGGCGGCA AGGCTGGCCC GGTCGGCACC AGTTGCGTGA GCGGAAAGAT |
| 721 | GGCCGCTTCC CGGCCCTGCT GCAGGGAGCT CAAAATGGAG GACGCGGCGC TCGGGAGAGC |
| 781 | GGGCGGGTGA GTCACCCACA CAAAGGAAAA GGGCCTTTCC GTCCTCAGCC GTCGCTTCAT |
| 841 | GTGACTCCAC GGAGTACCGG GCGCCGTCCA GGCACCTCGA TTAGTTCTCG AGCTTTTGGA |
| 901 | GTACGTCGTC TTTAGGTTGG GGGAGGGGT TTTATGCGAT GGAGTTTCCC CACACTGAGT |
| 961 | GGGTGGAGAC TGAAGTTAGG CCAGCTTGGC ACTTGATGTA ATTCTCCTTG GAATTTGCCC |
| 1021 | TTTTTGAGTT TGGATCTTGG TTCATTCTCA AGCCTCAGAC AGTGGTTCAA AGTTTTTTTC |
| 1081 | TTCCATTTCA GGTGTCGTGA GGAATTAGCT TGGTACTAGA GGATCCCCGG TCGCCACCAT |
| 1141 | GGTGAGCAAG GGCGAGGAGC TGTTCACCGG GGTGGTGCCC ATCCTGGTCG AGCTGGACGG |
| 1201 | CGACGTAAAC GGCCACAAGT TCAGCGTGTC CGGCGAGGGC GAGGGCGATG CCACCTACGG |
| 1261 | CAAGCTGACC CTGAAGTTCA TCTGCACCAC CGGCAAGCTG CCCGTGCCCT GGCCCACCCT |
| 1321 | CGTGACCACC CTGACCTACG GCGTGCAGTG CTTCAGCCGC TACCCCGACC ACATGAAGCA |
| 1381 | GCACGACTTC TTCAAGTCCG CCATGCCCGA AGGCTACGTC CAGGAGCGCA CCATCTTCTT |
| 1441 | CAAGGACGAC GGCAACTACA AGACCCGCGC CGAGGTGAAG TTCGAGGGCG ACACCCTGGT |
| 1501 | GAACCGCATC GAGCTGAAGG GCATCGACTT CAAGGAGGAC GGCAACATCC TGGGGCACAA |
| 1561 | GCTGGAGTAC AACTACAACA GCCACAACGT CTATATCATG GCCGACAAGC AGAAGAACGG |
| 1621 | CATCAAGGTG AACTTCAAGA TCCGCCACAA CATCGAGGAC GGCAGCGTGC AGCTCGCCGA |
| 1681 | CCACTACCAG CAGAACACCC CCATCGGCGA CGGCCCCGTG CTGCTGCCCG ACAACCACTA |
| 1741 | CCTGAGCACC CAGTCCGCCC TGAGCAAAGA CCCCAACGAG AAGCGCGATC ACATGGTCCT |
| 1801 | GCTGGAGTTC GTGACCGCCG CCGGGATCAC TCTCGGCATG GACGAGCTGT ACAAGTAAAG |
| 1861 | CGGCCAAATC GTACGCCTAG GTGATCAAGA TCTGCTAGCT TAATTAACCC GGGACTAGTG |
| 1921 | CGGCCGCCAC CGCGGGGATC CAGACATGAT AAGATACATT GATGAGTTTG GACAAACCAC |
| 1981 | AACTAGAATG CAGTGAAAAA AATGCTTTAT TTGTGAAATT TGTGATGCTA TTGCTTTATT |
| 2041 | TGTAACCATT ATAAGCTGCA ATAAACAAGT TAACAACAAC AATTGCATTC ATTTTATGTT |
| 2101 | TCAGGTTCAG GGGGAGGTGT GGGAGGTTTT TTCGGATCCT CTAGAGTCGA CCGGACCGCT |
| 2161 | GCAGGCATGC CTGCTATTGT CTTCCCAATC CTCCCCCTTG CTGTCCTGCC CACCCCACC |
| 2221 | CCCCAGAATA GAATGACACC TACTCAGACA ATGCGATGCA ATTTCCTCAT TTTATTAGGA |
| 2281 | AAGGACAGTG GGAGTGGCAC CTTCCAGGGT CAAGGAAGGC ACGGGGGAGG GCAAACAAC |
| 2341 | AGATGGCTGG CAACTAGAAG GCACAGTCGA GGTGATCAGC GGGTTTAAAC GGGCCCTCTA |
| 2401 | GTAACGGCCG CCAGTGTGCT GGAATTCGCC CTTCAGGCCT ATGCTATCCT CTAGGCAATG |
| 2461 | TGATGGTCAG GGAAAGGGGC CCAGTGTTAT GTGGCTCTTT AGACACTAAT CAGCTGGGGG |
| 2521 | AAAAGTTCAT TGGCAAAAGT ATCCTCCCAG GAGTGGTCTG TACCAAGTGG AGAAGACATG |
| 2581 | TCACTGAAGG GAGAAGGGGA GCCCTCATAT CCACAGTCAC TGTGAGCGTC CAGCAGGCAA |
| 2641 | GAAGGTGGTC TCAGACAATG GCTGGATGAA AGCAGGTTTG AGATGCCCAG CTCTGGGATG |
| 2701 | AAGTCATCTT CCAAAGGCTC TTTCTTCACT GAGACAATGA ATTCAGGGTG ATCCTCTTCT |

TABLE I-continued (SEQ ID NO: 1)

```
2761  GAAGAGCTTA GAGGTGCTTC CTCAATTTTC ACTACCACGT TAGTTTGACT CTCTGTCTCA
2821  GAGGGGATCT CTAAAACTAG AGGCTTGGTG TATACATGGT CAAAACGAAT GAGTTCATTA
2881  ATGGCTTCCA GCTTGGCTGA TGAGGTCCCC ACTGACAGAG AAAGGGAGGC TGGTAAGGAA
2941  CTAGGTCCTT CTGGGTAGAC CTCTGGGAGT TCCTCCAGAC TAGCAGACTC TGGGGAAGGA
3001  CATTTGAAAA ACATGACAGG GTCCAACTTG TCCAGAATGC CAAAAGGAT ATCAGACTCA
3061  GAATCTGAAG AGGCAACAGT GTCAGAGTCC ATGGGAAGAT GTTCTGGGGA GGTGACAACT
3121  GGGCCTGCAC CTGCTGCGGA CTCAGCAGAC CCGGCCACCA GCCTTACTCC ACTCCCCTTG
3181  GCCTCCACCT CTGGAACCTC GTCAGGATCC AGCGTGTCCA TTCCCAAGCG TGTTCTTAAC
3241  TCCTGGTTCT CAACCACAAG GCCGTGAGTT TTCTCCCGTA AAAGCTGATT TTCTAGCTGG
3301  AGTTTGTGGT TCTCTTCTTC CAAATCCACC ACTTGCTGCT CCAGCTCGCT CATCCGGGCT
3361  TTCTTTCTAT CTCGAGCAGT CTGCGCTGCT ACTCTGTTTT TCAGTTTCCT CCGCAGCGCT
3421  TTCTCCTCCG GGCTCAGGTG CGTGAGCCGC TGCCGCTTGC GAGCCTGCGG TGTCCCGCTC
3481  GCCTCCGACC CTGCTGCCCG CGGACCGGGT ACCATGAGCG GCAGCGCCCG GCCGCCGGAG
3541  GCGGGCTGGC CAGATAAGAG TAGCACTTTG GGGGCCGCCG TGGCCGCGCT CGGCGCCGCT
3601  GCCACCACCA CCATAGCCAG GAAGCTTAAG TTTAAACGCT AGCCAGCTTG GGTCTCCCTA
3661  TAGTGAGTCG TATTAATTTC GATAAGCCAG TAAGCAGTGG GTTCTCTAGT TAGCCAGAGA
3721  GCTCTGCTTA TATAGACCTC CCACCGTACA CGCCTACCGC CCATTTGCGT CAATGGGGCG
3781  GAGTTGTTAC GACATTTTGG AAAGTCCCGT TGATTTTGGT GCCAAAACAA ACTCCCATTG
3841  ACGTCAATGG GGTGGAGACT TGGAAATCCC CGTGAGTCAA ACCGCTATCC ACGCCCATTG
3901  ATGTACTGCC AAAACCGCAT CACCATGGTA ATAGCGATGA CTAATACGTA GATGTACTGC
3961  CAAGTAGGAA AGTCCCATAA GGTCATGTAC TGGGCATAAT GCCAGGCGGG CCATTTACCG
4021  TCATTGACGT CAATAGGGGG CGTACTTGGC ATATGATACA CTTGATGTAC TGCCAAGTGG
4081  GCAGTTTACC GTAAATACTC CACCCATTGA CGTCAATGGA AAGTCCCTAT TGGCGTTACT
4141  ATGGGAACAT ACGTCATTAT TGACGTCAAT GGGCGGGGGT CGTTGGGCGG TCAGCCAGGC
4201  GGGCCATTTA CCGTAAGTTA TGTAACGCGG AACTCCATAT ATGGGCTATG AACTAATGAC
4261  CCCGTAATTG ATTACTATTA ATAACTAGTC AATAATCAAT GTCAACGCGT ATATCTGGCC
4321  CGTACATCGC GAAGCAGCGC AAAACGCCTA ACCCTAAGCA GATTCTTCAT GCAATTGCCT
4381  AGTTCGAAGC CACGCGTCCG AAGGGCGAAT TGTAGATAAG TAGCATGGCG GTTAATCAT
4441  TAACTACAAG GAACCCCTAG TGATGGAGTT GGCCACTCCC TCTCTGCGCG CTCGCTCGCT
4501  CACTGAGGCC GGGCGACCAA AGGTCGCCCG ACGCCCGGGC TTTGCCCGGG CGGCCTCAGT
4561  GAGCGAGCGA GCGCGCAGAG AGGGACAGAT CTGCCGGTCT CCCTATAGTG AGTCGTATTA
4621  ATTTCGATAA GCCAGGTTAA CCTGCATTAA TGAATCGGCC AACGCGCGGG GAGAGGCGGT
4681  TTGCGTATTG GGCGCTCTTC CGCTTCCTCG CTCACTGACT CGCTGCGCTC GGTCGTTCGG
4741  CTGCGGCGAG CGGTATCAGC TCACTCAAAG GCGGTAATAC GGTTATCCAC AGAATCAGGG
4801  GATAACGCAG GAAAGAACAT GTGAGCAAAA GGCCAGCAAA AGGCCAGGAA CCGTAAAAAG
4861  GCCGCGTTGC TGGCGTTTTT CCATAGGCTC CGCCCCCCTG ACGAGCATCA CAAAAATCGA
4921  CGCTCAAGTC AGAGGTGGCG AAACCCGACA GGACTATAAA GATACCAGGC GTTTCCCCCT
4981  GGAAGCTCCC TCGTGCGCTC TCCTGTTCCG ACCCTGCCGC TTACCGGATA CCTGTCCGCC
5041  TTTCTCCCTT CGGGAAGCGT GGCGCTTTCT CAATGCTCAC GCTGTAGGTA TCTCAGTTCG
```

TABLE I-continued (SEQ ID NO: 1)

| | |
|---|---|
| 5101 | GTGTAGGTCG TTCGCTCCAA GCTGGGCTGT GTGCACGAAC CCCCCGTTCA GCCCGACCGC |
| 5161 | TGCGCCTTAT CCGGTAACTA TCGTCTTGAG TCCAACCCGG TAAGACACGA CTTATCGCCA |
| 5221 | CTGGCAGCAG CCACTGGTAA CAGGATTAGC AGAGCGAGGT ATGTAGGCGG TGCTACAGAG |
| 5281 | TTCTTGAAGT GGTGGCCTAA CTACGGCTAC ACTAGAAGGA CAGTATTTGG TATCTGCGCT |
| 5341 | CTGCTGAAGC CAGTTACCTT CGGAAAAAGA GTTGGTAGCT CTTGATCCGG CAAACAAACC |
| 5401 | ACCGCTGGTA GCGGTGGTTT TTTTGTTTGC AAGCAGCAGA TTACGCGCAG AAAAAAAGGA |
| 5461 | TCTCAAGAAG ATCCTTTGAT CTTTTCTACG GGGTCTGACG CTCAGTGGAA CGAAAACTCA |
| 5521 | CGTTAAGGGA TTTTGGTCAT GAGATTATCA AAAAGGATCT TCACCTAGAT CCTTTTAAAT |
| 5581 | TAAAAATGAA GTTTTAAATC AATCTAAAGT ATATATGAGT AAACTTGGTC TGACAGTTAC |
| 5641 | CAATGCTTAA TCAGTGAGGC ACCTATCTCA GCGATCTGTC TATTTCGTTC ATCCATAGTT |
| 5701 | GCCTGACTCC CCGTCGTGTA GATAACTACG ATACGGGAGG GCTTACCATC TGGCCCCAGT |
| 5761 | GCTGCAATGA TACCGCGAGA CCCACGCTCA CCGGCTCCAG ATTTATCAGC AATAAACCAG |
| 5821 | CCAGCCGGAA GGGCCGAGCG CAGAAGTGGT CCTGCAACTT TATCCGCCTC CATCCAGTCT |
| 5881 | ATTAATTGTT GCCGGGAAGC TAGAGTAAGT AGTTCGCCAG TTAATAGTTT GCGCAACGTT |
| 5941 | GTTGCCATTG CTACAGGCAT CGTGGTGTCA CGCTCGTCGT TTGGTATGGC TTCATTCAGC |
| 6001 | TCCGGTTCCC AACGATCAAG GCGAGTTACA TGATCCCCCA TGTTGTGCAA AAAAGCGGTT |
| 6061 | AGCTCCTTCG GTCCTCCGAT CGTTGTCAGA AGTAAGTTGG CCGCAGTGTT ATCACTCATG |
| 6121 | GTTATGGCAG CACTGCATAA TTCTCTTACT GTCATGCCAT CCGTAAGATG CTTTTCTGTG |
| 6181 | ACTGGTGAGT ACTCAACCAA GTCATTCTGA GAATAGTGTA TGCGGCGACC GAGTTGCTCT |
| 6241 | TGCCCGGCGT CAATACGGGA TAATACCGCG CCACATAGCA GAACTTTAAA AGTGCTCATC |
| 6301 | ATTGGAAAAC GTTCTTCGGG GCGAAAACTC TCAAGGATCT TACCGCTGTT GAGATCCAGT |
| 6361 | TCGATGTAAC CCACTCGTGC ACCCAACTGA TCTTCAGCAT CTTTTACTTT CACCAGCGTT |
| 6421 | TCTGGGTGAG CAAAAACAGG AAGGCAAAAT GCCGCAAAAA AGGGAATAAG GGCGACACGG |
| 6481 | AAATGTTGAA TACTCATACT CTTCCTTTTT GAAGCATTTA TCAGGGTTAT CAATATTATT |
| 6541 | TGTCTCATGA GCGGATACAT ATTTGAATGT ATTTAGAAAA ATAAACAAAT AGGGGTTCCG |
| 6601 | CGCACATTTC CCCGAAAAGT GCCACCTGAC GTCTAAGAAA CCATTATTAT CATGACATTA |
| 6661 | ACCTATAAAA ATAGGCGTAT CACGAGGCCC TTTCGTCTCG CGCGTTTCGG TGATGACGGT |
| 6721 | GAAAACCTCT GACACATGCA GCTCCCGGAG ACGGTCACAG CTTGTCTGTA AGCGGATGCC |
| 6781 | GGGAGCAGAC AAGCCCGTCA GGGCGCGTCA GCGGGTGTTG GCGGGTGTCG GGGCTGGCTT |
| 6841 | AACTATGCGG CATCAGAGCA GATTGTACTG AGAGTGCACC ATATGGACAT ATTGTCGTTA |
| 6901 | GAACGCGGCT ACAATTAATA CATAACCTTA TGTATCATAC ACATACGATT TAGGTGACAC |
| 6961 | TATAGAACTC GAGCAGCTGA AGCTTGAATT CATCGATGAT ATCAGATCTG GCCACTCCC |
| 7021 | TCTCTGCGCG CTCGCTCGCT CACTGAGGCC GGGCGACCAA AGGTCGCCCG ACGCCCGGGC |
| 7081 | TTTGCCCGGG CGGCCTCAGT GAGCGAGCGA GCGCGCAGAG AGGGAGTGGC CAACTCCATC |
| 7141 | ACTAGGGGTT CCTGGAGGGG TGGAGTCGTG ACAATTCGCC CTTGGGCCTA GGCAATTGGA |
| 7201 | TCCGCC |

TABLE II

(SEQ ID NO: 2)

Xbp1s (Human)

```
ORIGIN
    1 GGCGCTGGGC GGCTGCGGCG CGCGGTGCGC GGTGCGTAGT CTGGAGCTAT GGTGGTGGTG
   61 GCAGCCGCGC CGAACCCGGC CGACGGGACC CCTAAAGTTC TGCTTCTGTC GGGGCAGCCC
  121 GCCTCCGCCG CCGGAGCCCC GGCCGGCCAG GCCCTGCCGC TCATGGTGCC AGCCCAGAGA
  181 GGGGCCAGCC CGGAGGCAGC GAGCGGGGGG CTGCCCCAGG CGCGCAAGCG ACAGCGCCTC
  241 ACGCACCTGA GCCCCGAGGA GAAGGCGCTG AGGAGGAAAC TGAAAAACAG AGTAGCAGCT
  301 CAGACTGCCA GAGATCGAAA GAAGGCTCGA ATGAGTGAGC TGGAACAGCA AGTGGTAGAT
  361 TTAGAAGAAG AGAACCAAAA ACTTTTGCTA GAAAATCAGC TTTTACGAGA GAAAACTCAT
  421 GGCCTTGTAG TTGAGAACCA GGAGTTAAGA CAGCGCTTGG GGATGGATGC CCTGGTTGCT
  481 GAAGAGGAGG CGGAAGCCAA GGGGAATGAA GTGAGGCCAG TGGCCGGGTC TGCTGAGTCC
  541 GCAGCAGGTG CAGGCCCAGT TGTCACCCCT CCAGAACATC TCCCCATGGA TTCTGGCGGT
  601 ATTGACTCTT CAGATTCAGA GTCTGATATC CTGTTGGGCA TTCTGGACAA CTTGGACCCA
  661 GTCATGTTCT TCAAATGCCC TTCCCCAGAG CCTGCCAGCC TGGAGGAGCT CCCAGAGGTC
  721 TACCCAGAAG GACCCAGTTC CTTACCAGCC TCCCTTTCTC TGTCAGTGGG GACGTCATCA
  781 GCCAAGCTGG AAGCCATTAA TGAACTAATT CGTTTTGACC ACATATATAC CAAGCCCCTA
  841 GTCTTAGAGA TACCCTCTGA GACAGAGAGC CAAGCTAATG TGGTAGTGAA AATCGAGGAA
  901 GCACCTCTCA GCCCCTCAGA GAATGATCAC CCTGAATTCA TTGTCTCAGT GAAGGAAGAA
  961 CCTGTAGAAG ATGACCTCGT TCCGGAGCTG GGTATCTCAA ATCTGCTTTC ATCCAGCCAC
 1021 TGCCCAAAGC CATCTTCCTG CCTACTGGAT GCTTACAGTG ACTGTGGATA CGGGGGTTCC
 1081 CTTTCCCCAT TCAGTGACAT GTCCTCTCTG CTTGGTGTAA ACCATTCTTG GGAGGACACT
 1141 TTTGCCAATG AACTCTTTCC CCAGCTGATT AGTGTCTAAG GAATGATCCA ATACTGTTGC
 1201 CCTTTTCCTT GACTATTACA CTGCCTGGAG GATAGCAGAG AAGCCTGTCT GTACTTCATT
 1261 CAAAAAGCCA AAATAGAGAG TATACAGTCC TAGAGAATTC CTCTATTTGT TCAGATCTCA
 1321 TAGATGACCC CCAGGTATTG TCTTTTGACA TCCAGCAGTC CAAGGTATTG AGACATATTA
 1381 CTGGAAGTAA GAAATATTAC TATAATTGAG AACTACAGCT TTTAAGATTG TACTTTTATC
 1441 TTAAAGGGT GGTAGTTTTC CCTAAAATAC TTATTATGTA AGGGTCATTA GACAAATGTC
 1501 TTGAAGTAGA CATGGAATTT ATGAATGGTT CTTTATCATT TCTCTTCCCC CTTTTTGGCA
 1561 TCCTGGCTTG CCTCCAGTTT TAGGTCCTTT AGTTTGCTTC TGTAAGCAAC GGGAACACCT
 1621 GCTGAGGGGG CTCTTTCCCT CATGTATACT TCAAGTAAGA TCAAGAATCT TTTGTGAAAT
 1681 TATAGAAATT TACTATGTAA ATGCTTGATG GAATTTTTTC CTGCTAGTGT AGCTTCTGAA
 1741 AGGTGCTTTC TCCATTTATT TAAAACTACC CATGCAATTA AAGGTACAA TGCAAAAAAA
 1801 AAAAAAAAA
```

TABLE III (SEQ ID NO: 3)

Adeno-associated virus 2, complete genome
GenBank: AF043303.1

```
ORIGIN
   1 TTGGCCACTC CCTCTCTGCG CGCTCGCTCG CTCACTGAGG CCGGGCGACC AAAGGTCGCC
  61 CGACGCCCGG GCTTTGCCCG GGCGGCCTCA GTGAGCGAGC GAGCGCGCAG AGAGGGAGTG
 121 GCCAACTCCA TCACTAGGGG TTCCTGGAGG GGTGGAGTCG TGACGTGAAT TACGTCATAG
 181 GGTTAGGGAG GTCCTGTATT AGAGGTCACG TGAGTGTTTT GCGACATTTT GCGACACCAT
 241 GTGGTCACGC TGGGTATTTA AGCCCGAGTG AGCACGCAGG GTCTCCATTT TGAAGCGGGA
 301 GGTTTGAACG CGCAGCCGCC ATGCCGGGGT TTTACGAGAT TGTGATTAAG GTCCCCAGCG
 361 ACCTTGACGA GCATCTGCCC GGCATTTCTG ACAGCTTTGT GAACTGGGTG GCCGAGAAGG
 421 AATGGGAGTT GCCGCCAGAT TCTGACATGG ATCTGAATCT GATTGAGCAG GCACCCCTGA
 481 CCGTGGCCGA GAAGCTGCAG CGCGACTTTC TGACGGAATG GCGCCGTGTG AGTAAGGCCC
 541 CGGAGGCCCT TTTCTTTGTG CAATTTGAGA AGGGAGAGAG CTACTTCCAC ATGCACGTGC
 601 TCGTGGAAAC CACCGGGGTG AAATCCATGG TTTTGGGACG TTTCCTGAGT CAGATTCGCG
 661 AAAAACTGAT TCAGAGAATT TACCGCGGGA TCGAGCCGAC TTTGCCAAAC TGGTTCGCGG
 721 TCACAAAGAC CAGAAATGGC GCCGGAGGCG GGAACAAGGT GGTGGATGAG TGCTACATCC
 781 CCAATTACTT GCTCCCCAAA ACCCAGCCTG AGCTCCAGTG GGCGTGGACT AATATGGAAC
 841 AGTATTTAAG CGCCTGTTTG AATCTCACGG AGCGTAAACG GTTGGTGGCC CAGCATCTGA
 901 CGCACGTGTC GCAGACGCAG GAGCAGAACA AAGAGAATCA GAATCCCAAT TCTGATGCGC
 961 CGGTGATCAG ATCAAAAACT TCAGCCAGGT ACATGGAGCT GGTCGGGTGG CTCGTGGACA
1021 AGGGGATTAC CTCGGAGAAG CAGTGGATCC AGGAGGACCA GGCCTCATAC ATCTCCTTCA
1081 ATGCGGCCTC CAACTCGCGG TCCCAAATCA AGGCTGCCTT GGACAATGCG GGAAAGATTA
1141 TGAGCCTGAC TAAAACCGCC CCCGACTACC TGGTGGGCCA GCAGCCCGTG GAGGACATTT
1201 CCAGCAATCG GATTTATAAA ATTTTGGAAC TAAACGGGTA CGATCCCCAA TATGCGGCTT
1261 CCGTCTTTCT GGGATGGGCC ACGAAAAAGT TCGGCAAGAG GAACACCATC TGGCTGTTTG
1321 GGCCTGCAAC TACCGGGAAG ACCAACATCG CGGAGGCCAT AGCCCACACT GTGCCCTTCT
1381 ACGGGTGCGT AAACTGGACC AATGAGAACT TTCCCTTCAA CGACTGTGTC GACAAGATGG
1441 TGATCTGGTG GGAGGAGGGG AAGATGACCG CCAAGGTCGT GGAGTCGGCC AAAGCCATTC
1501 TCGGAGGAAG CAAGGTGCGC GTGGACCAGA AATGCAAGTC CTCGGCCCAG ATAGACCCGA
1561 CTCCCGTGAT CGTCACCTCC AACACCAACA TGTGCGCCGT GATTGACGGG AACTCAACGA
1621 CCTTCGAACA CCAGCAGCCG TTGCAAGACC GGATGTTCAA ATTTGAACTC ACCCGCCGTC
1681 TGGATCATGA CTTTGGGAAG GTCACCAAGC AGGAAGTCAA AGACTTTTTC CGGTGGGCAA
1741 AGGATCACGT GGTTGAGGTG GAGCATGAAT TCTACGTCAA AAAGGGTGGA GCCAAGAAAA
1801 GACCCGCCCC CAGTGACGCA GATATAAGTG AGCCCAAACG GGTGCGCGAG TCAGTTGCGC
1861 AGCCATCGAC GTCAGACGCG GAAGCTTCGA TCAACTACGC AGACAGGTAC CAAAACAAAT
1921 GTTCTCGTCA CGTGGGCATG AATCTGATGC TGTTTCCCTG CAGACAATGC GAGAGAATGA
1981 ATCAGAATTC AAATATCTGC TTCACTCACG GACAGAAAGA CTGTTTAGAG TGCTTTCCCG
2041 TGTCAGAATC TCAACCCGTT CTGTCGTCA AAAAGGCGTA TCAGAAACTG TGCTACATTC
2101 ATCATATCAT GGGAAAGGTG CCAGACGCTT GCACTGCCTG CGATCTGGTC AATGTGGATT
2161 TGGATGACTG CATCTTTGAA CAATAAATGA TTTAAATCAG GTATGGCTGC CGATGGTTAT
```

TABLE III-continued (SEQ ID NO: 3)

| | |
|---|---|
| 2221 | CTTCCAGATT GGCTCGAGGA CACTCTCTCT GAAGGAATAA GACAGTGGTG GAAGCTCAAA |
| 2281 | CCTGGCCCAC CACCACCAAA GCCCGCAGAG CGGCATAAGG ACGACAGCAG GGGTCTTGTG |
| 2341 | CTTCCTGGGT ACAAGTACCT CGGACCCTTC AACGGACTCG ACAAGGGAGA GCCGGTCAAC |
| 2401 | GAGGCAGACG CCGCGGCCCT CGAGCACGAC AAAGCCTACG ACCGGCAGCT CGACAGCGGA |
| 2461 | GACAACCCGT ACCTCAAGTA CAACCACGCC GACGCGGAGT TTCAGGAGCC CCTTAAAGAA |
| 2521 | GATACGTCTT TTGGGGGCAA CCTCGGACGA GCAGTCTTCC AGGCGAAAAA GAGGGTTCTT |
| 2581 | GAACCTCTGG GCCTGGTTGA GGAACCTGTT AAGACGGCTC CGGGAAAAAA GAGGCCGGTA |
| 2641 | GAGCACTCTC CTGTGGAGCC AGACTCCTCC TCGGGAACCG GAAAGGCGGG CCAGCAGCCT |
| 2701 | GCAAGAAAAA GATTGAATTT TGGTCAGACT GGAGACGCAG ACTCAGTACC TGACCCCCAG |
| 2761 | CCTCTCGGAC AGCCACCAGC AGCCCCTCT GGTCTGGGAA CTAATACGAT GGCTACAGGC |
| 2821 | AGTGGCGCAC CAATGGCAGA CAATAACGAG GGCGCCGACG GAGTGGGTAA TTCCTCGGGA |
| 2881 | AATTGGCATT GCGATTCCAC ATGGATGGGC GACAGAGTCA TCACCACCAG CACCCGAACC |
| 2941 | TGGGCCCTGC CCACCTACAA CAACCACCTC TACAAACAAA TTTCCAGCCA ATCAGGAGCC |
| 3001 | TCGAACGACA ATCACTACTT TGGCTACAGC ACCCCTTGGG GGTATTTTGA CTTCAACAGA |
| 3061 | TTCCACTGCC ACTTTTCACC ACGTGACTGG CAAAGACTCA TCAACAACAA CTGGGGATTC |
| 3121 | CGACCCAAGA GACTCAACTT CAAGCTCTTT AACATTCAAG TCAAAGAGGT CACGCAGAAT |
| 3181 | GACGGTACGA CGACGATTGC CAATAACCTT ACCAGCACGG TTCAGGTGTT TACTGACTCG |
| 3241 | GAGTACCAGC TCCCGTACGT CCTCGGCTCG GCGCATCAAG GATGCCTCCC GCCGTTCCCA |
| 3301 | GCAGACGTCT TCATGGTGCC ACAGTATGGA TACCTCACCC TGAACAACGG GAGTCAGGCA |
| 3361 | GTAGGACGCT CTTCATTTTA CTGCCTGGAG TACTTTCCTT CTCAGATGCT GCGTACCGGA |
| 3421 | AACAACTTTA CCTTCAGCTA CACTTTTGAG GACGTTCCTT TCCACAGCAG CTACGCTCAC |
| 3481 | AGCCAGAGTC TGGACCGTCT CATGAATCCT CTCATCGACC AGTACCTGTA TTACTTGAGC |
| 3541 | AGAACAAACA CTCCAAGTGG AACCACCACG CAGTCAAGGC TTCAGTTTTC TCAGGCCGGA |
| 3601 | GCGAGTGACA TTCGGGACCA GTCTAGGAAC TGGCTTCCTG GACCCTGTTA CCGCCAGCAG |
| 3661 | CGAGTATCAA AGACATCTGC GGATAACAAC AACAGTGAAT ACTCGTGGAC TGGAGCTACC |
| 3721 | AAGTACCACC TCAATGGCAG AGACTCTCTG GTGAATCCGG GCCCGGCCAT GGCAAGCCAC |
| 3781 | AAGGACGATG AAGAAAAGTT TTTTCCTCAG AGCGGGGTTC TCATCTTTGG GAAGCAAGGC |
| 3841 | TCAGAGAAAA CAAATGTGGA CATTGAAAAG GTCATGATTA CAGACGAAGA GGAAATCAGG |
| 3901 | ACAACCAATC CCGTGGCTAC GGAGCAGTAT GGTTCTGTAT CTACCAACCT CCAGAGAGGC |
| 3961 | AACAGACAAG CAGCTACCGC AGATGTCAAC ACACAAGGCG TTCTTCCAGG CATGGTCTGG |
| 4021 | CAGGACAGAG ATGTGTACCT TCAGGGGCCC ATCTGGGCAA AGATTCCACA CACGGACGGA |
| 4081 | CATTTTCACC CCTCTCCCCT CATGGGTGGA TTCGGACTTA ACACCCCTCC TCCACAGATT |
| 4141 | CTCATCAAGA ACACCCCGGT ACCTGCGAAT CCTTCGACCA CCTTCAGTGC GGCAAAGTTT |
| 4201 | GCTTCCTTCA TCACACAGTA CTCCACGGGA CAGGTCAGCG TGGAGATCGA GTGGGAGCTG |
| 4261 | CAGAAGGAAA ACAGCAAACG CTGGAATCCC GAAATTCAGT ACACTTCCAA CTACAACAAG |
| 4321 | TCTGTTAATG TGGACTTTAC TGTGGACACT AATGGCGTGT ATTCAGAGCC TCGCCCCATT |
| 4381 | GGCACCAGAT ACCTGACTCG TAATCTGTAA TTGCTTGTTA ATCAATAAAC CGTTTAATTC |
| 4441 | GTTTCAGTTG AACTTTGGTC TCTGCGTATT TCTTTCTTAT CTAGTTTCCA TGGCTACGTA |
| 4501 | GATAAGTAGC ATGGCGGGTT AATCATTAAC TACAAGGAAC CCCTAGTGAT GGAGTTGGCC |

TABLE III-continued (SEQ ID NO: 3)

| 4561 | ACTCCCTCTC TGCGCGCTCG CTCGCTCACT GAGGCCGGGC GACCAAAGGT CGCCCGACGC |
| 4621 | CCGGGCTTTG CCCGGGCGGC CTCAGTGAGC GAGCGAGCGC GCAGAGAGGG AGTGGCCAA |

TABLE IV (SEQ ID NO: 4)

Xbp1s (Mouse)

```
ORIGIN
    1 CTAGGGTAAA ACCGTGAGAC TCGGTCTGGA AATCTGGCCT GAGAGGACAG CCTGGCAATC
   61 CTCAGCCGGG GTGGGGACGT CTGCCGAAGA TCCTTGGACT CCAGCAACCA GTGGTCGCCA
  121 CCGTCCATCC ACCCTAAGGC CCAGTTTGCA CGGCGGAGAA CAGCTGTGCA GCCACGCTGG
  181 ACACTCACCC CGCCCGAGTT GAGCCCGCCC CCGGGACTAC AGGACCAATA AGTGATGAAT
  241 ATACCCGCGC GTCACGGAGC ACCGGCCAAT CGCGGACGGC CACGACCCTA GAAAGGCTGG
  301 GCGCGGCAGG AGGCCACGGG GCGGTGGCGG CGCTGGCGTA GACGTTTCCT GGCTATGGTG
  361 GTGGTGGCAG CGGCGCCGAG CGCGGCCACG GCGGCCCCCA AAGTGCTACT CTTATCTGGC
  421 CAGCCCGCCT CCGGCGGCCG GGCGCTGCCG CTCATGGTAC CCGGTCCGCG GGCAGCAGGG
  481 TCGGAGGCGA GCGGGACACC GCAGGCTCGC AAGCGGCAGC GGCTCACGCA CCTGAGCCCG
  541 GAGGAGAAAG CGCTGCGGAG GAAACTGAAA ACAGAGTAG CAGCGCAGAC TGCTCGAGAT
  601 AGAAAGAAAG CCCGGATGAG CGAGCTGGAG CAGCAAGTGG TGGATTTGGA AGAAGAGAAC
  661 CACAAACTCC AGCTAGAAAA TCAGCTTTTA CGGGAGAAAA CTCACGGCCT TGTGGTTGAG
  721 AACCAGGAGT TAAGAACACG CTTGGGAATG GACACGCTGG ATCCTGACGA GGTTCCAGAG
  781 GTGGAGGCCA AGGGGAGTGG AGTAAGGCTG GTGGCCGGGT CTGCTGAGTC CGCAGCAGGT
  841 GCAGGCCCAG TTGTCACCTC CCCAGAACAT CTTCCCATGG ACTCTGACAC TGTTGCCTCT
  901 TCAGATTCTG AGTCTGATAT CCTTTTGGGC ATTCTGGACA AGTTGGACCC TGTCATGTTT
  961 TTCAAATGTC CTTCCCCAGA GTCTGCTAGT CTGGAGGAAC TCCCAGAGGT CTACCCAGAA
 1021 GGACCTAGTT CCTTACCAGC CTCCCTTTCT CTGTCAGTGG GGACCTCATC AGCCAAGCTG
 1081 GAAGCCATTA ATGAACTCAT TCGTTTTGAC CATGTATACA CCAAGCCTCT AGTTTTAGAG
 1141 ATCCCCTCTG AGACAGAGAG TCAAACTAAC GTGGTAGTGA AAATTGAGGA AGCACCTCTA
 1201 AGCTCTTCAG AAGAGGATCA CCCTGAATTC ATTGTCTCAG TGAAGAAAGA GCCTTTGGAA
 1261 GATGACTTCA TCCCAGAGCT GGGCATCTCA AACCTGCTTT CATCCAGCCA TTGTCTGAGA
 1321 CCACCTTCTT GCCTGCTGGA CGCTCACAGT GACTGTGGAT ATGAGGGCTC CCCTTCTCCC
 1381 TTCAGTGACA TGTCTTCTCC ACTTGGTACA GACCACTCCT GGGAGGATAC TTTTGCCAAT
 1441 GAACTTTTCC CCCAGCTGAT TAGTGTCTAA AGAGCCACAT AACACTGGGC CCCTTTCCCT
 1501 GACCATCACA TTGCCTAGAG GATAGCATAG GCCTGTCTCT TTCGTTAAAA GCCAAAGTAG
 1561 AGGCTGTCTG GCCTTAGAAG AATTCCTCTA AAGTATTTCA AATCTCATAG ATGACTTCCA
 1621 AGTATTGTCG TTTGACACTC AGCTGTCTAA GGTATTCAAA GGTATTCCAG TACTACAGCT
 1681 TTTGAGATTC TAGTTTATCT TAAAGGTGGT AGTATACTCT AAATCGCAGG GAGGGTCATT
 1741 TGACAGTTTT TTCCCAGCCT GGCTTCAAAC TATGTAGCCG AGGCTAGGCA GAAACTTCTG
 1801 ACCCTCTTGA CCCCACCTCC CAAGTGCTGG GCTTCACCAG GTGTGCACCT CCACACCTGC
 1861 CCCCCCGACA TGTCAGGTGG ACATGGGATT CATGAATGGC CCTTAGCATT TCTTTCTCCA
```

TABLE IV-continued (SEQ ID NO: 4)

| | | | | | |
|---|---|---|---|---|---|
| 1921 | CTCTCTGCTT | CCCAGGTTTC | GTAACCTGAG | GGGGCTTGTT | TTCCCTTATG TGCATTTTAA |
| 1981 | ATGAAGATCA | AGAATCTTTG | TAAAATGATG | AAAATTTACT | ATGTAAATGC TTGATGGATC |
| 2041 | TTCTTGCTAG | TGTAGCTTCT | AGAAGGTGCT | TTCTCCATTT | ATTTAAAACT ACCCTTGCAA |
| 2101 | TTAAAAAAAA | AGCAACACAG | CGTCCTGTTC | TGTGATTTCT | AGGGCTGTTG TAATTTCTCT |
| 2161 | TTATTGTTGG | CTAAAGGAGT | AATTTATCCA | ACTAAAGTGA | GCATACCACT TTTTAAAGTC |
| 2221 | AAAAAAAAAA | AAAAAAA | | | |

The invention claimed is:

1. A method of treating and/or delaying amyotrophic lateral sclerosis (ALS) in a mammal suffering therefrom, the method comprising administering to the mammal a therapeutically effective amount of a vector that induces neuronal overexpression of X-Box protein 1 (XBP1) in the central nervous system (CNS) of the mammal, wherein the vector is an adeno-associated virus (AAV) vector.

2. The method of claim 1, wherein said AAV vector comprises a recombinant adeno-associated viral sequence comprising an expression cassette that comprises a transcriptional regulatory element for expression in neuronal tissues operatively linked to a polynucleotide encoding XBP1.

3. The method of claim 2, wherein said transcriptional regulatory element comprises a promoter.

4. The method of claim 3, wherein said promoter is selected from the group consisting of EF-1α, cmv, cba, Pgk1, Cam2, CamIIK, ChAT and Thy1.

5. The method of claim 2, wherein said recombinant adeno-associated viral sequence further comprises AAV inverted terminal repeats (ITRs).

6. The method of claim 5, wherein said ITRs are from an AAV serotype selected from the group consisting of AAV1, AAV2, AAV3, AAV4, AAV5, AAV6, AAV7, AAV8, AAV9, AAV10, AAV11 and pseudo-typed AAVs.

7. The method of claim 6, wherein said ITRs are from the serotype AAV2.

8. The method of claim 2, wherein said polynucleotide encoding XBP1 acts systemically, close to, or within neuronal cells.

9. The method of claim 8, wherein said polynucleotide encoding XBP1 is specific for cells in the cortex and spinal cord, motor neurons and/or Purkinje cells in the cerebellum.

10. The method of claim 1, wherein said method generates a reduction of astrogliosis in the mammal.

11. The method of claim 1, wherein said method delays the symptomatic phase of amyotrophic lateral sclerosis phenotype in the mammal.

12. The method of claim 1, wherein said mammal is a human.

13. The method of claim 2, wherein the polynucleotide comprises a sequence as defined in SEQ ID NO:2.

14. The method of claim 1, wherein the vector is administered to the mammal in a pharmaceutical composition further comprising a pharmaceutically acceptable excipient.

15. The method of claim 1, wherein said vector is administered to the mammal by nasal route, by direct cerebral-intraventricular injection and/or by intrathecal injection.

* * * * *